United States Patent
Qvit-Raz et al.

(10) Patent No.: US 9,868,957 B2
(45) Date of Patent: *Jan. 16, 2018

(54) TOPICAL COMPOSITION COMPRISING TRANSFORMED BACTERIA EXPRESSING A COMPOUND OF INTEREST

(71) Applicant: TopGeniX, Inc., Menlo Park, CA (US)

(72) Inventors: Noga Qvit-Raz, Menlo Park, CA (US); Tahel Altman, Menlo Park, CA (US)

(73) Assignee: TOPGENIX, INC., Menlo Park, CA (US)

( * ) Notice: Subject to any disclaimer, the term of this patent is extended or adjusted under 35 U.S.C. 154(b) by 732 days.

This patent is subject to a terminal disclaimer.

(21) Appl. No.: 13/961,826

(22) Filed: Aug. 7, 2013

(65) Prior Publication Data

US 2014/0044677 A1 Feb. 13, 2014

Related U.S. Application Data

(60) Provisional application No. 61/836,594, filed on Jun. 18, 2013, provisional application No. 61/680,620, filed on Aug. 7, 2012.

(51) Int. Cl.

| | | |
|---|---|---|
| *A61K 8/99* | (2017.01) | |
| *C12N 15/74* | (2006.01) | |
| *A61Q 17/04* | (2006.01) | |
| *A61Q 17/00* | (2006.01) | |
| *A61K 35/744* | (2015.01) | |
| *A61K 8/27* | (2006.01) | |
| *A61K 8/40* | (2006.01) | |
| *A61Q 19/00* | (2006.01) | |
| *A61Q 19/08* | (2006.01) | |

(52) U.S. Cl.
CPC ............. *C12N 15/746* (2013.01); *A61K 8/27* (2013.01); *A61K 8/40* (2013.01); *A61K 8/99* (2013.01); *A61K 35/744* (2013.01); *A61Q 17/00* (2013.01); *A61Q 17/04* (2013.01); *A61K 2800/592* (2013.01); *A61Q 19/007* (2013.01); *A61Q 19/08* (2013.01)

(58) Field of Classification Search
CPC .......... C12N 15/746; A61K 8/99; A61K 8/18; A61Q 19/007; A61Q 17/00
See application file for complete search history.

(56) References Cited

U.S. PATENT DOCUMENTS

| | | |
|---|---|---|
| 4,259,444 A | 3/1981 | Chakraharty |
| 5,207,998 A | 5/1993 | Robinson et al. |
| 5,576,354 A | 11/1996 | DeFlandre et al. |
| 5,620,682 A | 4/1997 | Fogel |
| 6,221,648 B1 | 4/2001 | Le Page et al. |
| 6,605,286 B2 | 8/2003 | Steldler et al. |
| 6,787,147 B1 | 9/2004 | Huner et al. |
| 7,081,442 B2 | 7/2006 | Seiberg et al. |
| 2009/0130073 A1 | 5/2009 | Reindi et al. |
| 2009/0232751 A1 | 9/2009 | Lott et al. |
| 2012/0263661 A1 | 10/2012 | Grune |
| 2012/0301452 A1 | 11/2012 | Gueniche et al. |
| 2012/0308525 A1* | 12/2012 | Greenberg et al. .......... 424/93.4 |
| 2014/0044653 A1 | 2/2014 | Qvit-Raz et al. |

FOREIGN PATENT DOCUMENTS

| | | |
|---|---|---|
| EP | 0975227 B1 | 2/2000 |
| EP | 1322313 B1 | 7/2003 |
| EP | 1473028 A1 | 11/2004 |
| EP | 1789529 A1 | 5/2007 |
| EP | 2364712 B1 | 9/2011 |
| EP | 2561853 A1 | 2/2013 |
| FR | 2803201 A1 | 7/2001 |
| WO | WO86/02350 A1 | 4/1986 |
| WO | WO 1989/001970 A2 | 3/1989 |
| WO | WO 1996/011277 A1 | 4/1996 |
| WO | WO 2002/028402 A1 | 4/2002 |
| WO | WO 2002/039974 A1 | 5/2002 |
| WO | WO 2003/020236 A2 | 3/2003 |
| WO | WO 2006/013441 A2 | 2/2006 |
| WO | WO 2007/039086 A1 | 4/2007 |
| WO | WO 2011/150127 A2 | 12/2011 |
| WO | WO 2011/151426 A2 | 12/2011 |
| WO | WO 2012/150269 A1 | 11/2012 |
| WO | WO 2013/044059 A2 | 3/2013 |
| WO | WO2013/181741 A1 | 12/2013 |

OTHER PUBLICATIONS

Rodrigues et al (Industrial Crops and Products, 49: 634-644, 2013).*
De la Coba (Journal of Dermatological Science, 55(3): 161-169, 2009).*
Workshop overview (Forum on Microbial Health; Workshop Summary. Washington (DC): National Academies Press (US); 2014, p. 1-89).*
Ebanks et al (Int. J. Mol. Sci, 10: 4066-4087, 2009).*
"Aethic, King's College London to develop first sunscreen based on mycosporine-like amino acids", King's College London; Online article downloaded from http://www.news-medical.net/news/20120912/Aethic-Kings-College-London-to-develop-first-sunscreen-based-on-mycosporine-like-amino-acids.aspx, article published on Sep. 12, 2012.
Balskus et al., "The genetic and molecular basis for sunscreen biosynthesis in cyanobacteria", Science, vol. 329, No. 5999, pp. 1653-1656 (2010).
"Helionori® for a natural bioprotection against UVA, Ecocert Approved, Patent FR9916785", Gelyma, Parc D' Affaires Marseille Sud, Online Article; Retreived from the internet from http://www.biosiltech.com/sites/default/files/Helionori.pdf, 4 pages, pdf created on Apr. 3, 2009.

(Continued)

*Primary Examiner* — Anoop Singh
*Assistant Examiner* — Magdalene Sgagias
(74) *Attorney, Agent, or Firm* — Shay Glenn LLP

(57) ABSTRACT

Compositions comprised of a population of transformed bacteria formulated for topical application to a subject are described. The population of transformed bacteria are created from a non-pathogenic bacteria and transformed to express a compound of interest for a therapeutic or a cosmetic purpose. In one embodiment, the composition is for protection of the skin from ultraviolet rays.

4 Claims, 3 Drawing Sheets

(56) References Cited

OTHER PUBLICATIONS

Ouwehand et al., "Probiotics for the skin: a new area of potential application?", Letters in Applied Microbiology, vol. 36, pp. 327-331 (2003).
"Synthesizing UV-protective compounds in bacteria", iGEM 2012 Team Minnesota Project, Online Article, Retreived from the internet from http://2012.igem.org/Team:Minnesota/Protective/US_Absorption , 5 pages (2012).
Torres et al., "A new UV-B absorbing mycosporine with photo protective activity from the lichenized ascomycete Collema cristatum"; Eur. J. Biochem., vol. 271, No. 4, pp. 780-784 (2004).
Gueniche et al., "Bifidobacterium longum lysate, a new ingredient for reactive skin", Exp. Dermatol., vol. 19, No. 8, pp. 31-38 (2010).
Joo et al., "Therapeutic advantages of medicinal herbs fermented with Lactobacillus plantarum, in topical application and its activities on atopic dermatitis", Phytother. Res., vol. 23, No. 7, (2009).
Kleerebezem et al., "Controlled gene expression systems for lactic acid bacteria: transferavle nisin-inducible expression cassettes for Lactococcus, Leuconostoc, and *Lactobacillus* spp", Appl. Environ. Microbiol., vol. 63, No. 11, pp. 4581-4584 (1997).
Perez-Arellano et al., "Construction of compatible wide-host-range shuttle vectors for lactic acid bacteria and *Escherichia coli*", Plasmid., vol. 46, No. 2, pp. 106-116 (2001).
Pouwels et al., "Genetics of lactobacilli: plasmids and gene expression", Antonie Van Leeuwenhoek, vol. 64, No. 2, pp. 85-107 (1993).
Reid et al., "Potential uses of probiotics in clinical practice", Clin. Microbiol. Rev., vol. 16, No. 4, pp. 658-672 (2003).
Sanchez and Mayo, "General and specialized vactors derived from pBM02, a new rolling circle replicating plasmid of Lactococcus lactis", Plasmid., vol. 51, No. 3, pp. 265-271 (2004).
Gao et al., "Microbial ultraviolet sunscreens", Nature Reviews Microbiology, vol. 9, pp. 791-802 (2011).
Hentges, "The anaerobic microflora of the human body", Clinical Inectious Disease, vol. 16, No. 4, pp. S175-S180 (1993).
Rastogi et al., "Photoprotective compounds from marine organisms", J. Ind. Microbiol. Biotechnol., vol. 37, pp. 537-558 (2010).
Shick et al., "Mycosporine-like amino acids and related gadusols:Biosynthesis, accumulation, and UV-protective functions in aquatic organisms", Ann. Rev. Physiol., vol. 64, pp. 223-262 (2002).
Boyle, "Bacteria could be engineered to produce natural biosunscreen", Popular Science, retrieved from the internet: URL:http://www.popsci.com/science/article/2010-09/algaes-natural-bio-sunscreen-could-lead-better-skin-protection, (Sep. 9, 2010).
International Search Report from related PCT Patent Application No. PCT/US2013/054026 dated Oct. 28, 2013, 5 pgs.
Steidler et al., "Therapeutic drug delivery by genetically modified Lactococcus lactis", Annals of the New York Academy of Sciences, pp. 176-186, (Sep. 3, 2005).
Steidler, "Delivery of therapeutic proteins to the mucosa using genetically modified microflora", Expert Opin. Drug Del., vol. 2, No. 4, pp. 737-746 (2005).
Vangelista et al., "Engineering of Lactobacillus jensenii to secrete RANTES and a CCR5 antagonist analogue as live HIV-1 Blockers", Antimicrobial Agents and Chemotherapy, vol. 54, No. 7, pp. 2994-3001 (2010).
Wells et al., "Mucosal delivery of therapeutic and prophylactic molecules using lactic acid bacteria", Nat. Rev. Microbiol., vol. 6, No. 5, pp. 349-362 (2008).
Zhu et al., "Genetically enaineered bacteria expressing alphaMelanocyte stimulating hormone alphaMSH as an inhibitor of traumatic ocular inflammatory reaction in rats", Invest. Opthalmol. Vis. Sci., E-Abstract 4005, 2 pgs. (2004), retrieved from the internet: URL:http://abstracts.iovs.org/cgi/content/abstract/45/5/4005 on Nov. 26, 2013.
Qvit-Raz et al.; U.S. Appl. No. 14/863,236 entitled "Topical composition comprising transformed bacteria expressing a compound of interest," filed Sep. 23, 2015.
Balskus et al.; The genetic and molecular basis for sunscreen biosynthesis in cyanobacteria; Science; 329(5999); pp. 1653-1656; Sep. 24, 2010 (with Supporting Online Material).
Costello et al.; Bacterial community variation in human body habitats across space and time; Science; 326(5960); pp. 1694-1697; Dec. 18, 2009 (Author Manuscript).
Davison; Risk mitigation of genetically modified bacteria and plants designed for bioremediation; J. Ind. Microbiol. Biotechnol.; 32(11-12); pp. 639-650; Dec. 2005.
Eichenbaum et al.; Use of the lactococcal nisA promoter to regulate gene expression in gram-positive bacteria: comparison of induction level and promoter strenght; Appl. Environ. Microbiol.; 64(8); pp. 2763-2769; Aug. 1998.
Elliot et al.; Defining a bacteriophage T4 late promoter: absence of a "-35" region; Cell; 36(1); pp. 211-219; Jan. 1984.
Fuller; Probiotics in human medicine; Gut; 32(4); pp. 439-442; Apr. 1991.
Gaudu et al.; Respiration capacity and consequences in lactococcus lactis; Antonie Van Leeuwenhoek; 82(1-4); pp. 263-269; Aug. 2002.
Gonzalez et al.; Photostability of commercial sunscreens upon sun exposure and irradiation by ultraviolet lamps; BMC Dermatol.; 7:1; 9 pages; Feb. 26, 2007.
Green; Microbial biogeography: from taxonomy to traits; Science; 320(5879); pp. 1039-1043; May 23, 2008.
Grice et al.; Topographical and temporal diversity of the human skin microbiome; Science; 324(5931); pp. 1190-1192; May 29, 2009 (Author Manuscript).
Grice et al.; The skin microbiome; Nat. Rev. Microbiol.; 9(4); pp. 244-253; Apr. 2011 (Author Manuscript).
Huang et al.; Industrial production of recombinant therapeutics in *Escherichia coli* and its recent advancements; J. Ind. Microbiol. Biotechnol.; 39(3); pp. 383-399; Mar. 2012.
Kiatpapan et al.; Genetic manipulation system in propionibacterium; J. Biosci. Bioeng.; 93(1); pp. 1-8; 2002 (year of pub. sufficiently earlier than effective US filing date and any foreign priority date).
Kim et al.; A xylose-inducible bacillus subtilis integration vector and its application; Gene; 181(1-2); pp. 71-76; Nov. 28, 1996.
Kim et al.; Improvement of a nisin-inducible expression vector for use in lactic acid bacteria; Plasmid; 58(3); pp. 275-283; Nov. 2007.
Klann et al.; Estrogen-like effects of ultraviolet screen 3-(4-methylbenzlidene)-camphor (Eusolex 6300) on cell proliferation and gene induction in mammalian and amphibian cells; Environ. Res.; 97(3); pp. 274-281; Mar. 2005.
Knowland et al.; Sunlight-induced mutagenicity of a common sunscreen ingredient; FEBS Lett.; 324(3); pp. 309-313; Jun. 21, 1993.
Kok et al.; Construction of plasmid cloning vectors for lactic streptococci which also replicate in bacillus subtilis and *Escherichia coli*; Appl. Environ. Microbiol.; 48(4); pp. 726-731; Oct. 1984.
Li et al.; Glutathione protects lactococcus lactis against oxidative stress; Appl. Environ. Microbiol.; 69(10); pp. 5739-5745; Oct. 2003.
Luchansky et al.; Molecular cloning and deoxyribonucleic acid polymorphisms in lactobacillus acidophilus and lactobacillus gasseri; J. Dairy Sci..; 74(10); pp. 3293-3302; Oct. 1991.
Mierau et al.; 10 years of the nisin-controlled gene expression system (NICE) in lactococcus lactis; Appl. Microbiol. Biotechnol.; 68(6); pp. 705-717; Oct. 2005.
Nguyen et al.; A food-grade system for inducible gene expression in lactobacillus plantarum using an alanine racemase-encoding selection marker; J. Agric. Food Chem.; 59(10); pp. 5617-5624; May 25, 2011.
Nouaille et al.; Heterologous protein production and delivery systems for lactococcus lactis; Genet. Mol. Res.; 2(1); pp. 102-111; Mar. 31, 2003.
Packaged Facts; The U.S. market for suncare and lipcare products: market report; © 2015; 7 pages; retrieved Jul. 23, 2015 from the internet: http://www.packagedfacts.com/sitemap/product.asp?productid=222308.
Rolfe; The role of probiotic cultures in the control of gastrointestinal health; J. Nutr.; 130(2S Suppl); pp. 396S-402S; Feb. 2000.

(56) References Cited

OTHER PUBLICATIONS

Rud et al.; A synthetic promoter library for constitutive gene expression in lactobacillus plantarum; Microbiology; 152(Pt 4); pp. 1011-1019; Apr. 2006.
Russo et al.; Learning how to manipulate dna's double helix has fuelled job growth in biotechnology during the past 50 years; 421(6921); pp. 456-457; Jan. 23, 2003.
Sambandan et al.; Sunscreens: an overview and update; J. Am. Acad. Dermatol.; 64(4); pp. 748-758; Apr. 2011.
Shareck et al.; Cloning vectors based on cryptic plasmids isolated from lactic acid bacteria: their characteristics and potential applications in biotechnology; Crit. Rev. Biotechnol.; 24(4); pp. 155-208; 2004 (year of pub. sufficiently earlier than effective US filing date and any foreign priority date).
Sorensen; Towards universal systems for recombinant gene expression; Microbial Cell Factories; 9:27; 4 pages; Apr. 2010.
Steidler et al.; Biological containment of genetically modified lactococcus lactis for intestinal delivery of human interleukin 10; Nat. Biotechnol.; 21(7); pp. 785-789; Jul. 2003.
Stern; Clinical practice. Treatment of photoaging; N. Engl. J. Med.; 350 (15); pp. 1526-1534; Apr. 2004.
Storm et al.; On in 3 prescriptions are never redeemed: primary nonadherence in an outpatient clinic; J. Am. Acad. Dermatol.; 59(1); pp. 27-33; Jul. 2008.
Tarras-Wahlberg et al.; Changes in ultraviolet absorption of sunscreens after ultraviolet irradiation; J. Invest. Dermatol.; 113(4); pp. 547-553; Oct. 1999.
Telemet Inc.; Make snow; © 2015; 6 pages; retrieved from the internet http://www.telemet.com/snow/snomax.asp.
Van De Guchte et al.; Heterologous gene expression in *Lactococcus lactis* subsp. Lactis: synthesis, secretion, and processing of the bacillus subtilis neutral protease; Appl. Environ. Microbiol.; 56(9); pp. 2606-2611; Sep. 1990.
Van Der Vossen et al.; Characterization of transcription initiation and termination signals of the proteinase genes of lactococcus lactis Wg2 and enhancement of proteolysis in *L. lactis*; Appl. Environ. Microbiol.; 58(9); pp. 3142-3149; Sep. 1992.
Wallace et al.; A set of synthetic oligodeoxyribonucleotide primers for DNA sequencing in the plasmid vector pBR322; Gene; 16(1-3); pp. 21-26; Dec. 1981.
Wang et al.; Plasmids in lactobacillus; Crit. Rev. Biotechnol.; 17(3); pp. 227-272; 1997 (year of pub. sufficiently earlier than effective US filing date and any foreign priority date).
Weickert et al.; Genetic analysis of the promoter region of the bacillus subtilis alpha-amylase gene; J. Bacteril.; 171(7); pp. 3656-3666; Jul. 1989.
Wells et al.; Lactococcus lactis: high-level expression of tetanus toxin fragment c and protection against lethal challenge; Mol. Microbiol.; 8(6); pp. 1155-1162; Jun. 1993.
Yagur-Kroll et al.; Strategies for enhancing bioluminescent bacterial sensor performance by promoter region manipulation; Bioeng. Bugs; 1(2); pp. 151-153; Mar.-Apr. 2010.
Llewellyn et al.; Distribution and abundance of MAAs in 33 species of microalgae across 13 classes; Mar. Drugs; 8(4); pp. 1273-1291; Apr. 2010.
Padwa; Cyano-o-silyhydroxylamines as nitrone blocking groups. J. Chem. Soc., Chem. Commun.; 10; pp. 789-790; May 1986.
White et al.; Transformations of quinic acid. Asymmetric synthesis and absolute configurations of mycosporin I and mycosporin-gly. The Journal of Organic Chemistry; 60(12); pp. 3600-3611; Jun. 1995.
White et al.; the synthesis and absolute configuration of micosporins. A novel application of the staudinger reaction. J. Am. Chem. Soc.; 111(24); pp. 8970-8972; Nov. 1989.

\* cited by examiner

TOPICAL COMPOSITION COMPRISING TRANSFORMED BACTERIA EXPRESSING A COMPOUND OF INTEREST

CROSS-REFERENCE TO RELATED APPLICATIONS

This application claims the benefit of U.S. Provisional Application No. 61/680,620, filed Aug. 7, 2012, and of U.S. Provisional Application No. 61/836,594, filed Jun. 18, 2013, each of which is incorporated herein by reference in its entirety.

REFERENCE TO SEQUENCE LISTING, TABLE OR COMPUTER PROGRAM

A Sequence Listing is being submitted electronically via EFS in the form of a text file, created Aug. 7, 2013, and named "093242-0012-seqlist_ST25.txt" (68,614 bytes), the contents of which are incorporated herein by reference in their entirety.

TECHNICAL FIELD

The subject matter described herein relates to the field of dermatology, and more particularly, to compositions and methods of treatment that comprise transformed bacteria that express a molecule or compound for a topical therapeutic, cosmetic or dermatological purpose.

BACKGROUND

There are a spectrum of dermatological disorders and conditions that are commonly treated with a topically applied agent. In some treatments, the agent offers a therapeutic purpose, for example for treating or ameliorating psoriasis, eczema or dermatitis. In other treatments, the agent offers a cosmetic or protective effect, such as a skin lightening agent or depigmenting agent or a sun protective agent. Topical application of agents for cosmetics and medical purposes has certain limitations. For example, the applied agent can be swept off easily from the skin or the formulation in which the agent is applied can include chemicals that may interfere with the balance of the natural skin microbiota. Creams and ointments can be messy, greasy, cumbersome, and patients can only treat a limited number of lesions on a limited area, and only on certain anatomic sites. As a result, nearly 35% of prescriptions for topical preparations remained behind the pharmacy counter, the patient opting to not pick up the topical prescription. In contrast, prescriptions for systemic agents fared much better, with reports that only 14% went unredeemed (Storm, A. et al., *J. Am. Acad. Dermatol.*, 59:27-33 (2008)).

There are also disadvantages with topical treatments in terms of the patient understanding of how often and how much to apply. In the case of sunscreens, as just one example, people typically apply sunscreens less than half as thickly as and less often than recommended, thus compromising their protection substantially (Stern, R. S., *N Engl J. Med*, 350:1526-1534 (2004)).

There remains a need for more effective topical treatment compositions, for medical, cosmetic and preventative purposes. By way of example, the need for more effective UV protection is recognized around the world, as it is the main cause for the increasing incidence of skin cancers and photoaging. By way of another example, topical treatment of psoriasis and eczema, and other skin disorders, with an effective, long-term therapy is needed.

Healthy human epidermis is colonized by thousands of bacterial species, including bacterial members from mainly five orders harboring about 60% of the total skin microbiome in all people. A healthy human epidermis is colonized with trillions of bacterial cells, creating, on average, approximately $10^8$ bacteria per square centimeter. The skin microflora has evolved into commensal relationship with the host, as they exploit the unique attributes of the skin and keep the skin ecosystem in a healthy balance (Grice A. E., *Science*, 324: 1190-1192 (2009). A therapy that uses skin bacteria for different dermatological needs would be able to maintain the natural ecosystem of the skin, and also enhance those natural skin bacteria to address specific dermatological needs.

The use of probiotic micro-organisms for improving the skin's immune function under stress conditions, leading to immune suppression, specifically for normalizing the skin's immune activity and reducing the tendency to develop hyper-reactions under such conditions is described in the art, for example in EP Patent No. 1322318. Cosmetic use of probiotic microorganisms as an active agent useful for treating and/or preventing impairing radiance of the skin complexion has also been described (US2012/0301452). Use of solely probiotics, is one approach for topical skin treatments, yet there remains a need for a longer term and/or more potent approach.

Transformed bacteria are being used intensively in modern biotechnology for the production of recombinant proteins and various molecules for food, pharmaceutical, and biocatalysis applications. Bacteria able to produce and secrete proteins encoded by heterologous genes are used extensively for the industrial production of pharmaceutical proteins such as human and animal growth hormones, insulin, interferons, cytokines etc. Organisms other than *E. coli* thus far used or proposed for industrial production include cultured mammalian and insect cells, yeasts and fungi, and various bacteria species, including a number of *Bacillus* spp. Among the bacteria already widely used for industrial purposes are the lactic acid bacteria, which are employed as starter cultures for fermented foodstuffs, and as flavor enhancers, and preservatives. These properties depend on the ability of these organisms to produce certain enzymes, lactic acid and harmless antimicrobial polypeptides, such as nisin (see, for example. U.S. Pat. No. 6,221,648).

The foregoing examples of the related art and limitations related therewith are intended to be illustrative and not exclusive. Other limitations of the related art will become apparent to those of skill in the art upon a reading of the specification and a study of the drawings.

BRIEF SUMMARY

Figure 1A:
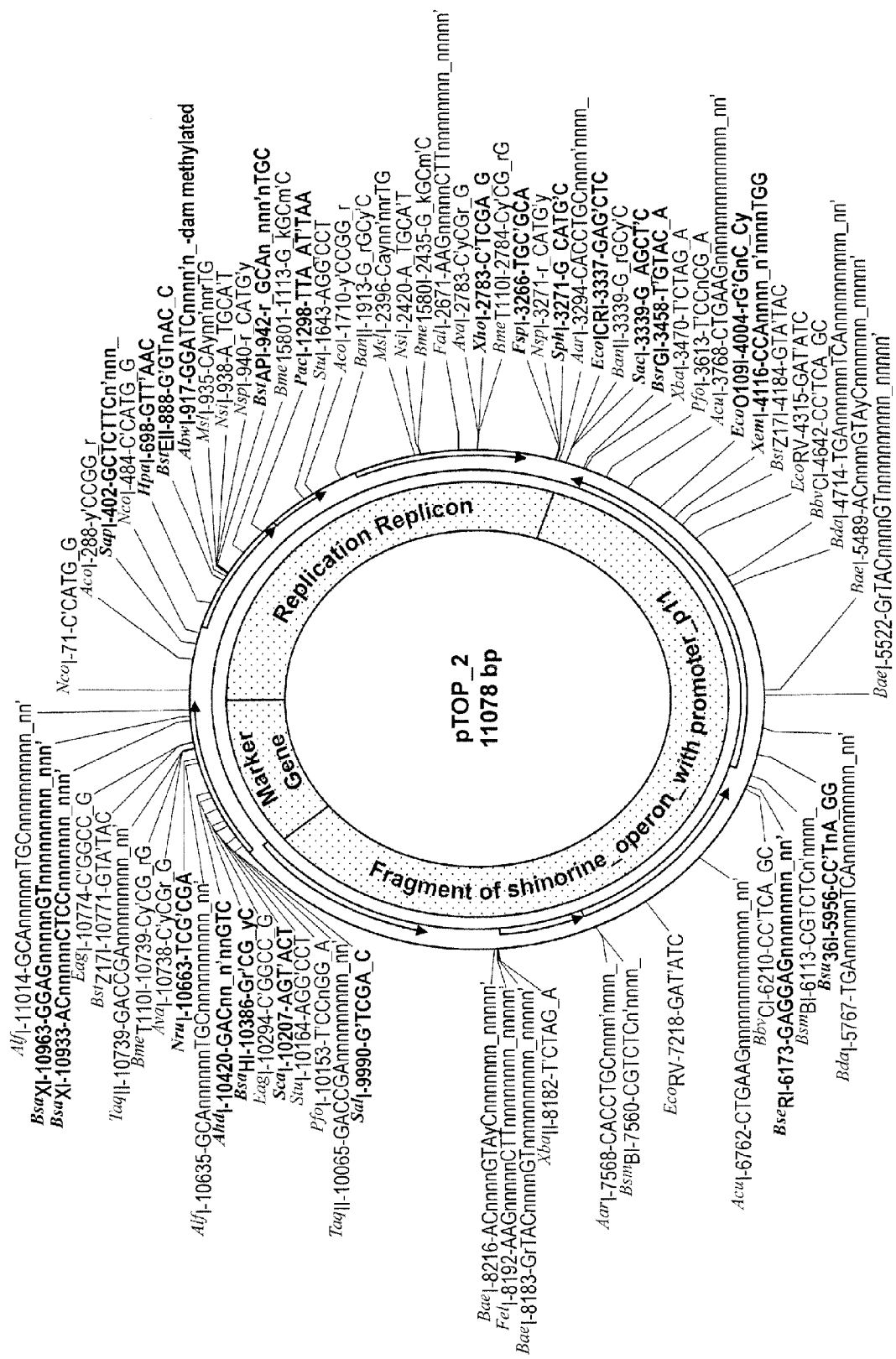
FIGS. 1A-1C are maps of an exemplary plasmid or vector for transforming a bacterium for expression of a compound of interest.

The following aspects and embodiments thereof described and illustrated below are meant to be exemplary and illustrative, not limiting in scope.

In one aspect, a composition comprising a population of transformed bacteria formulated for topical application to a subject is provided, where the population of transformed bacteria is created from a non-pathogenic bacteria transformed to express a compound of interest.

In one embodiment, the population of non-pathogenic bacteria comprises a bacteria that occurs naturally on the human skin; that is, the bacteria in the population are from the human skin microbiome. In another embodiment, the population of non-pathogenic bacteria is a population of live bacteria that express the compound of interest, and in one embodiment, that chronically express the compound of interest. In another embodiment, the population of non-pathogenic bacteria is a population of attenuated bacteria or killed (dead) bacteria, intact or fragments thereof, where the bacteria prior to attenuation or killing expressed the compound of interest.

In one embodiment, the compound of interest is one that can absorb or reflect ultraviolet light. In another embodiment, the compound can absorb or reflect ultraviolet A (320-400 nm), ultraviolet B (315-280 nm), or both.

In yet another embodiment, the compound of interest expressed by the transformed bacteria is selected from the group consisting of: mycosporine, gadusols, oxo-mycosporines, imino-mycosporines and mycosporine-like amino acids (MAAs), scytonemin, melanines, UV-screening/observing amino acids-like molecules, flavonoids, beta-lanines, UV-screening/observing pigments (e.g. carotenoids/cartenoproteins, xanthopylls and porphyrin-based/heme-porphyrin based), UV-screening/observing co-factors (e.g. tetrahydrobiopterin), phenylpropanoids, polyphenol (e.g. tannins), pycnogenol, tyrosinases (and its substrates and products), alpha hydroxy acids (AHAs), polysaccharides (e.g. glycosaminoglycans, (GAGs) or mucopolysaccharides), skin related cofactors, vitamin E, polymers, and additional skin related natural compounds, such as: collagen, keratin, elastin, linoleic acid, laminin, tretinoin, tazarotene, sargaquinoic acid, sargachromenol, fucoxanthin, retinoid, anti-inflammatory cytokines (as II-2), cortisone, tacrolimus, ciclosporin, resveratrol, gallocatechol, gallocatechin, epigallocatechin gallate, retinoid, vitamin A, vitamin A derivatives, beta-carotene, vitamin D, vitamin A derivatives, moisture compounds; cortisone, tacrolimus and ciclosporin, DNA repair enzymes; photolyase, endonuclease and glycosylase.

In yet another embodiment, the population of transformed bacteria is formulated into the composition to provide at least about $10^2$ bacteria per $cm^2$, or at least about $10^3$, $10^4$, $10^5$ or $10^6$ bacteria per $cm^2$.

In another embodiment, the composition comprises a second population of transformed bacteria formulated for topical application to a subject, wherein the second population of transformed bacteria is either or both (i) created from a non-pathogenic bacteria that is different from the first population of transformed bacteria in the composition or (ii) transformed to express a compound of interest that is different from the first compound of interest expressed by the first population of transformed bacteria in the composition. In other embodiments, the composition comprises at least one population of transformed bacteria, at least two populations of transformed bacteria, or two or more populations of transformed bacteria.

In one embodiment, the second population of non-pathogenic bacteria is from the human skin microbiome. In another embodiment, the second population of non-pathogenic bacteria is a population of live bacteria that express the compound of interest, and in one embodiment, chronically express the compound of interest. In another embodiment, the second population of non-pathogenic bacteria is a population of attenuated bacteria or killed (dead) bacteria, intact or fragments thereof, where the bacteria prior to attenuation or killing expressed the compound of interest.

In still another embodiment, the compound of interest is one for treating psoriasis. Exemplary compounds include, but are not limited to, a compound selected from the group consisting of retinoid, vitamin A, beta-carotene, vitamin D, anti-inflammatory cytokines.

In one embodiment, the compound of interest is an anti-oxidant.

In yet another embodiment, the compound is selected from the group consisting of resveratrol, vitamin E, vitamin C, -epigallocatechin-3-gallate, and retinyl palmitate (retinoids), lutein, tamarind, flavonoids, pycnogenol, lycopene.

In another embodiment, the compound of interest provides a cosmetic effect. For example, the compound may be selected from the group consisting of coenzyme Q10, tyrosinases, collagen, laminin, ceramids, linoleic acid, tretinoin, tazarotene and collagen. In still another embodiment, the cosmetic effect is anti-aging.

In still another embodiment, the compound of interest is one that treats eczema. Exemplary compounds of interest include a compound is selected from the group consisting of cortisone, tacrolimus and ciclosporin.

In other embodiments, the composition comprising the population of transformed bacterial is formulated for topical application to the face. In another embodiment, the composition is formulation for topical application to the skin, excluding mucosal surfaces of the human body.

In another embodiment, the population of transformed bacteria is created from a population of non-pathogenic bacteria resident on the skin in humans. That is, the population of non-pathogenic bacteria comprise a bacteria typically resident on skin in healthy, non-diseased human beings.

The population of transformed bacteria is created, in some embodiments, from nonpathogenic bacterial members selected from those in the group consisting of Actinomycetales, *Anaerococcus*, Bacillales, *Bifidobacterium, Enhydrobacter, Finegoldia, Carnobacterium, Coryneobacterium, Lactobacillus, Lactococcus*, Leunconostoc, Macrooccus, *Micrococcineae, Oenococcus, Pediococcus, Peptoniphilus, Propionibacterium, Salinicoccus, Sphingomonas, Strepococcus, Tetragenoccus*, and *Weissella*.

In other embodiments, the transformed bacteria in the population of transformed bacterial are not *Propionibacterium* acnes, a pathogenic strain of *Coryneobacterium, S. aureus*, or *S. epidermidis*.

In still another embodiment, the population of transformed bacteria is created from a bacteria selected from those in the group consisting of *Lactobacillus casei, Lactobacillus reuteri, Lactobacillus acidophilus, Lactobacillus jensenii, Bifidobacterium lognum, Bifidobacterium reuteri, Bifidobacterium lactis, Bifidobacterium breve, Bifidobacterium animalis, Propionibacterium acidipropionici, Propionibacterium freudenreichii, Propionibacterium thoenii*, and *Propionibacterium jensenii*.

In yet another embodiment, the population of transformed bacteria is created from a bacteria selected from those in a phylum selected from the group consisting of gamma-proteobacteria, alpha-proteobacteria, and bacteriodetes.

The topical composition that comprises the population of transformed bacteria can be, in various embodiments, a cream, lotion, emulsion, gel, ointment, liquid or spray. In one embodiment, the topical composition is formulated to provide at least about $10^2$ bacteria per $cm^2$.

In another aspect, a method of treatment is provided, wherein a composition as described herein is topically applied to the skin of a subject, preferably a human subject, for disease preventative, or for a therapeutic or cosmetic purpose. In embodiment, topically applying excludes topically applying to a mucosal surface (nasal, vaginal, rectal, oral surfaces) of a human body.

In addition to the exemplary aspects and embodiments described above, further aspects and embodiments will become apparent by reference to the drawings and by study of the following descriptions.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

I. Definitions

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

As used in this specification, the singular forms "a," "an," and "the" include plural referents unless the context clearly dictates otherwise. Thus, for example, reference to an "excipient" includes a single excipient as well as two or more of the same or different excipients.

"Amphiphilic" refers to a molecule combining hydrophilic and lipophilic (hydrophobic) properties.

"Diluents" may be included in the formulations to dissolve, disperse or otherwise incorporate another component in the formulation. Examples of diluents include, but are not limited to, water, buffered aqueous solutions, organic hydrophilic diluents, such as monovalent alcohols, and low molecular weight glycols and polyols (e.g. propylene glycol, polypropylene glycol, glycerol, butylene glycol).

A "gel" is a colloid in which the dispersed phase has combined with the continuous phase to produce a semisolid material, such as jelly.

"Hydrophilic" as used herein refers to substances that have strongly polar groups that readily interact with water.

"Hydrophobic" as used herein refers to substances that lack an affinity for water; tending to repel and not absorb water as well as not dissolve in or mix with water.

"Lipid soluble" as used herein refers to substances that have a solubility of greater than or equal to 5 g/100 mL in a hydrophobic liquid, such as castor oil.

"Lipophilic" refers to compounds having an affinity for lipids. Examples of lipophilic substances include but are not limited to naturally occurring and synthetic oils, fats, fatty acids, lecithins, triglycerides and combinations thereof.

An "oil" is a composition containing at least 95% wt of a lipophilic substance.

"Skin" intends to denote all of the epidermis of an individual, in particular a human being, and in some embodiments to intend, where specified, particular regions of the skin, such as the face, neck, arms, legs, abdomen, hands, back, buttocks, or feet.

"Water soluble" as used herein refers to substances that have a solubility of greater than or equal to 5 g/100 mL water.

II. Topical Composition

The composition described herein is comprised of a population of transformed bacteria formulated for topical application to a subject. Described in section A below are exemplary non-pathogenic bacteria suitable for creating the population of transformed bacteria. In section B, compounds of interest to be expressed by the population of transformed bacteria are described, and in section C techniques for creating the transformed bacterial population are set forth. In section D, topical compositions comprising the population of transformed bacteria are disclosed.

A. Exemplary Bacteria

The population of bacteria in the compositions described herein and for use in the described methods is created from a non-pathogenic bacterium that has been genetically modified to express, produce and/or secrete a compound of interest. In this section, exemplary non-pathogenic bacteria are described. In one embodiment, the bacteria in the population are non-pathogenic and non-invasive microorganisms, and can be in certain embodiments a gram-positive food grade bacterial strain. In another embodiment, the populations of transformed bacteria are prepared from a bacterium that occurs naturally in the skin microbiome.

Human skin is populated with microorganisms that reside on the skin, referred to as the skin microbiome. The bacterial microorganisms resident on the skin (in a healthy (non-diseased) human) are usually non-pathogenic and commensal (not harmful to the host) and/or mutualistic (offer a benefit). The bacteria commonly resident on the human skin are set forth in below, and are indicated by phylogenetic levels, described with their phylogenetic lineage, down to the genus level (Grice, E. A. et al., Science, 324(5931):1190-1192 (2009); Costello, E. K., et al. Science, 326(5960):1694-1697 (2009), Grice E. A. and J. A. Segre, Nature Reviews Microbiology, 9:244-253 (2011)).

The bacteria forming the population of bacteria in the composition, and that are transformed to express one or more compounds of interest, can be a collection of the same bacteria or a mixture of different bacteria, at different phylogenetic levels. In one embodiment, the populations of bacteria for transformation are a group of individuals of one bacterial species in an area that is separate from other groups of bacteria, apart from rare migration events. In practice, the size and nature of the area (e.g., size and location of area on skin, such as chin, forehead) is defined, often arbitrarily, for a desired purpose. In another embodiment, the bacteria for transformation to prepare the composition are a community of bacteria, intending a collection of populations of different bacteria species that occur together in space and time. In one embodiment, the community of bacteria includes all species (that is, across all trophic levels and/or phylogenetic levels), or, alternatively, includes all trophically similar species (for example, all the plants in a rainforest). In another embodiment, the bacteria for transformation to prepare the composition are a metapopulation, intending a group of populations that are perceived to exist as a series of local populations that are linked by migration between them. In another embodiment, the bacteria for transformation to prepare the composition are a metacommunity, intending an assemblage of trophically similar individuals and species, each of which is perceived to exist as a series of local communities, linked by the dispersal of potentially interacting species (Green, J. L. et al., *Science*, 320(5879):1039-43 (2008)).

Bacteria resident on the skin of healthy humans include bacterial species typically resident on the face of humans, such as Actinobacteria, including bacterial in the genus *corynebacterium* and in the genus *propionibacterium*. In other embodiments, bacteria resident on the skin of healthy human subjects include bacterial species typically resident on skin other than the face, including for example bacteria in the genus bacteroidetes and proteobacteria. Other bacteria in the skin microbiome include those listed herein below.

In one embodiment, the bacteria are from the genus *Propionibacterium*, including but not limited to, *Propionibacterium acidifaciens, Propionibacterium acidipropionici, Propionibacterium acidipropionici* strain 4900, *Propionibacterium acnes, Propionibacterium australiense, Propionibacterium avidum, Propionibacterium cyclohexanicum, Propionibacterium freudenreichii* subsp. *Freudenreichii, P. freudenreichii* ssp. *freudenreichii* strain 20271, *Propionibacterium freudenreichii* subsp. *Shermanii, P. freudenreichii* ssp. *shermanii* strain 4902, *P. freudenreichii* ssp. *shermanii* strain 4902, *Propionibacterium granulosum, Propionibacterium innocuum, jensenii, P. jensenii* strain 20278, *Propionibacterium lymphophilum, Propionibacterium microaerophilum, Propionibacterium propionicum, Propionibacterium thoenii*, and *P. thoenii* strain 20277.

In another embodiment, the bacteria are a population of bacteria classified as "generally regarded as safe" (GRAS) in the *Propionibacterium* genus, including but not limited to *Propionibacterium acidipropionici, Propionibacterium freudenreichii* subsp. *Freudenreichii, Propionibacterium freudenreichii* subsp. *shermanii, Propionibacterium jensenii*, and *Propionibacterium thoenii*. In one embodiment, the bacteria is not *Propionibacterium acnes*.

In one embodiment, the bacteria are from the genus *Corynebacterium*, including but not limited to, *C. accolens, C. afermentan, C. amycolatum, C. argentoratense, C. aquaticum, C. auris, C. bovis, C. diphtheria, C. equi* (now *Rhodococcus equi*), *C. flavescens, C. glucuronolyticum, C. glutamicum, C. granulosum, C. haemolyticum, C. halofytica, C. jeikeium* (group JK), *C. macginleyi, C. matruchotii, C. minutissimum, C. parvum* (*Propionibacterium acnes*), *C. propinquum, C. pseudodiphtheriticum* (*C. hofmannii*), *C. pseudotuberculosis,* (*C. ovis*), *C. pyogenes, C. urealyticum* (group D2), *C. renale, C. spec, C. striatum, C. tenuis, C. ulcerans, C. urealyticum*, and *C. xerosis*. Bacterial with lipophilic and nonlipophilic groups are contemplated, and the nonlipophilic bacteria may include fermentative corynebacteria and nonfermentative corynebacteria.

In another embodiment, the bacteria are a population of bacteria classified as "generally regarded as safe" (GRAS) in the *Corynebacterium* genus, including but not limited to *Corynebacterium ammoniagenes, Corynebacterium casei, Corynebacterium flavescens*, and *Corynebacterium variabile*.

In one embodiment, the bacteria is not *C. diphtheria C. amicolatum, C. striatum, C. jeikeium, C. urealyticum*, and *C. xerosis, C. pseudotuberculosis, C. tenuis, C. striatum*, or *C. minutissimum*, as these may be pathogenic.

In one embodiment, the bacteria are from the suborder Micrococcineae, including but not limited to the GRAS bacteria species *Arthrobacter arilaitensis, Arthrobacter bergerei, Arthrobacter globiformis, Arthrobacter nicotianae, Kocuria rhizophila, Kocuria varians, Micrococcus luteus, Micrococcus lylae, Microbacterium gubbeenense, Brevibacterium aurantiacum, Brevibacterium casei, Brevibacterium linens, Brachybacterium alimentarium*, and *Brachybacterium tyrofermentans*.

In one embodiment, the bacteria are from the order Actinomycetales, including but not limited to the GRAS bacteria species *Streptomyces griseus* subsp. *Griseus*. In one embodiment, the bacteria *Streptomyces griseus* will not express tyrosinase.

In another embodiment, the bacteria are from the genus *Staphylococcus*, including but not limited to, *Staphylococcus agnetis, S. arlettae, S. auricularis, S. capitis, S. caprae, S. carnosus, Staphylococcus caseolyticus, S. chromogenes, S. cohnii, S. condiment, S. delphini, S. devriesei, S. equorum, S. felis, S. fleurettii, S. gallinarum, S. haemolyticus, S. hominis, S. hyicus, S. intermedius, S. kloosii, S. leei, S. lentus, S. lugdunensis, S. lutrae, S. massiliensis, S. microti, S. muscae, S. nepalensis, S. pasteuri, S. pettenkoferi, S. piscifermentans, S. pseudintermedius, S. pseudolugdunensis, S. pulvereri, S. rostra, S. saccharolyticus, S. saprophyticus, S. schleiferi, S. sciuri, S. simiae, S. simulans, S. stepanovicii, S. succinus, S. vitulinus, S. warneri*, and *S. xylosus*.

In another embodiment, the bacteria are a population of bacteria classified as "generally regarded as safe" (GRAS) in the order of *Staphylococcus*, including but not limited to, *Staphylococcus carnosus* subsp. *Carnosus, Staphylococcus carnosus* subsp. *Utilis, Staphylococcus cohnii, Staphylococcus condimenti, Staphylococcus equorum* subsp. *Equorum, Staphylococcus equorum* subsp. *Linens, Staphylococcus fleurettii, Staphylococcus piscifermentans, Staphylococcus saprophyticus, Staphylococcus sduri* subsp. *Sduri, Staphylococcus succinus* subsp *succinus, Staphylococcus succinus* subsp. *Casei, Staphylococcus vitulinus, Staphylococcus warneri*, and *Staphylococrus xylosus*.

In one embodiment, the bacteria is not *S. aureus* or *S. epidermidis*.

In another embodiment, the bacteria are from the genus *Streptococcus*, including but not limited to, *Streptococcus acidominimus, Streptococcus adjacens, Streptococcus agalactiae, Streptococcus alactolyticus, Streptococcus anginosus, Streptococcus australis, Streptococcus bovis, Streptococcus caballi, Streptococcus canis, Streptococcus caprinus, Streptococcus castoreus, Streptococcus cecorum, Streptococcus constellatus, Streptococcus constellatus* subsp. *Constellatus, Streptococcus constellatus* subsp. *Pharyngis, Streptococcus cremoris, Streptococcus criceti, Streptococcus cristatus, Streptococcus danieliae, Streptococcus defectives, Streptococcus dentapri, Streptococcus dentirousetti, Streptococcus didelphis, Streptococcus difficilis, Streptococcus durans, Streptococcus dysgalactiae, Streptococcus dysgalactiae* subsp. *Dysgalactiae, Streptococcus dysgalactiae* subsp. *Equisimilis, Streptococcus entericus, Streptococcus equi, Streptococcus equi* subsp. *Equi, Streptococcus equi* subsp. *Ruminatorum, Streptococcus equi* subsp. *Zooepi-* demicus, Streptococcus equines, Streptococcus faecalis, Streptococcus faecium, Streptococcus ferus, Streptococcus gallinaceus, Streptococcus gallolyticus, Streptococcus gallolyticus subsp. Gallolyticus, Streptococcus gallolyticus subsp. Macedonicus, Streptococcus gallolyticus subsp. Pasteurianus, Streptococcus garvieae, Streptococcus gordonii, Streptococcus halichoeri, Streptococcus hansenii, Streptococcus henryi, Streptococcus hyointestinalis, Streptococcus hyovaginalis, Streptococcus ictaluri, Streptococcus infantarius, Streptococcus infantarius subsp. Coli, Streptococcus infantarius subsp. Infantarius, Streptococcus infantis, Streptococcus iniae, Streptococcus intermedius, Streptococcus intestinalis, Streptococcus lactarius, Streptococcus lactis, Streptococcus lactis subsp. Cremoris, Streptococcus lactis subsp. Diacetilactis, Streptococcus lactis subsp. Lactis, Streptococcus lutetiensis, Streptococcus macacae, Streptococcus macedonicus, Streptococcus marimammalium, Streptococcus massiliensis, Streptococcus merionis, Streptococcus minor, Streptococcus mitis, Streptococcus morbillorum, Streptococcus mutans, Streptococcus oligofermentans, Streptococcus oralis, Streptococcus orisratti, Streptococcus ovis, Streptococcus parasanguinis, Streptococcus parauberis, Streptococcus parvulus, Streptococcus pasteurianus, Streptococcus peroris, Streptococcus phocae, Streptococcus plantarum, Streptococcus pleomorphus, Streptococcus pluranimalium, Streptococcus plurextorum, Streptococcus pneumonia, Streptococcus porci, Streptococcus porcinus, Streptococcus porcorum, Streptococcus pseudopneumoniae, Streptococcus pseudoporcinus, Streptococcus pyogenes, Streptococcus raffinolactis, Streptococcus ratti, Streptococcus rupicaprae, Streptococcus saccharolyticus, Streptococcus salivarius, Streptococcus salivarius subsp. Salivarius, Streptococcus salivarius subsp. Thermophilus, Streptococcus sanguinis, Streptococcus shiloi, Streptococcus sinensis, Streptococcus sobrinus, Streptococcus suis, Streptococcus thermophilus, Streptococcus thoraltensis, Streptococcus tigurinus, Streptococcus troglodytae, Streptococcus troglodytidis, Streptococcus uberis, Streptococcus urinalis, Streptococcus vestibularis, and Streptococcus waius.

In another embodiment, the bacteria are a population of bacteria classified as "generally regarded as safe" (GRAS) in the genus Streptococcus, including but not limited to, Streptococcus thermophilus strain Th4, Streptococcus gallolyticus subsp. Macedonicus, Streptococcus salivarius subsp. Salivarius, and Streptococcus salivarius subsp. Thermophilus.

In another embodiment, the bacteria are from the genus Lactobacillus, including but not limited to, Lactococcus garvieae, Lactococcus lactis, Lactococcus lactis subsp. cremoris, Lactococcus lactis subsp. hordniae, Lactococcus lactis, Lactococcus lactis subsp. Lactis, Lactococcus piscium, Lactococcus plantarum, Lactococcus raffinolactis, Lactobacillus acetotolerans, Lactobacillus acidophilus, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus aviarius, Lactobacillus aviarius subsp. araffinosus, Lactobacillus aviarius subsp. aviarius, Lactobacillus bavaricus, Lactobacillus bifermentans, Lactobacillus brevis, Lactobacillus buchneri, Lactobacillus bulgaricus, Lactobacillus carnis, Lactobacillus casei, Lactobacillus casei subsp. alactosus, Lactobacillus casei subsp. casei, Lactobacillus casei subsp. pseudoplantarum, Lactobacillus casei subsp. rhamnosus, Lactobacillus casei subsp. tolerans, Lactobacillus catenaformis, Lactobacillus cellobiosus, Lactobacillus collinoides, Lactobacillus confusus, Lactobacillus coryniformis, Lactobacillus coryniformis subsp. coryniformis, Lactobacillus coryniformis subsp. torquens, Lactobacillus crispatus, Lactobacillus curvatus, Lactobacillus curvatus subsp. curvatus, Lactobacillus curvatus subsp. melibiosus, Lactobacillus delbrueckii, Lactobacillus delbrueckii subsp. bulgaricus, Lactobacillus delbrueckii subsp. delbrueckii, Lactobacillus delbrueckii subsp. lactis, Lactobacillus divergens, Lactobacillus farciminis, Lactobacillus fermentum, Lactobacillus formicalis, Lactobacillus fructivorans, Lactobacillus fructosus, Lactobacillus gallinarum, Lactobacillus gasseri, Lactobacillus graminis, Lactobacillus halotolerans, Lactobacillus hamsteri, Lactobacillus helveticus, Lactobacillus heterohiochii, Lactobacillus hilgardii, Lactobacillus homohiochii, Lactobacillus iners, Lactobacillus intestinalis, Lactobacillus jensenii, Lactobacillus johnsonii, Lactobacillus kandleri, Lactobacillus kefiri, Lactobacillus kefuranofaciens, Lactobacillus kefirgranum, Lactobacillus kunkeei, Lactobacillus lactis, Lactobacillus leichmannii, Lactobacillus lindneri, Lactobacillus malefermentans, Lactobacillus mali, Lactobacillus maltaromicus, Lactobacillus manihotivorans, Lactobacillus minor, Lactobacillus minutus, Lactobacillus mucosae, Lactobacillus murinus, Lactobacillus nagelii, Lactobacillus oris, Lactobacillus panis, Lactobacillus parabuchneri, Lactobacillus paracasei, Lactobacillus paracasei subsp. paracasei, Lactobacillus paracasei subsp. tolerans, Lactobacillus parakefiri, Lactobacillus paralimentarius, Lactobacillus paraplantarum, Lactobacillus pentosus, Lactobacillus perolens, Lactobacillus piscicola, Lactobacillus plantarum, Lactobacillus pontis, Lactobacillus reuteri, Lactobacillus rhamnosus, Lactobacillus rhamnosus strain 5Æ5a, Lactobacillus rimae, Lactobacillus rogosae, Lactobacillus ruminis, Lactobacillus sakei, Lactobacillus sakei subsp. carnosus, Lactobacillus sakei subsp. sakei, Lactobacillus salivarius, Lactobacillus salivarius subsp. salicinius, Lactobacillus salivarius subsp. salivarius, Lactobacillus sanfranciscensis, Lactobacillus sharpeae, Lactobacillus suebicus, Lactobacillus trichodes, Lactobacillus uli, Lactobacillus vaccinostercus, Lactobacillus vaginalis, Lactobacillus viridescens, Lactobacillus vitulinus, Lactobacillus xylosus, Lactobacillus yamanashiensis, Lactobacillus yamanashiensis subsp. mali, Lactobacillus yamanashiensis subsp. Yamanashiensis and Lactobacillus zeae.

In another embodiment, the bacteria are a population of bacteria classified as "generally regarded as safe" (GRAS) in the genus Lactobacillus, including but not limited to, Lactobacillus acidophilus strain NP 28, Lactobacillus acidophilus strain NP51, Lactobacillus subsp. lactis strain NP7, Lactobacillus reuteri strain NCIMB 30242, Lactobacillus casei strain Shirota, Lactobacillus reuteri strain DSM 17938, Lactobacillus reuteri strain NCIMB 30242, Lactobacillus acidophilus NCFM, Lactobacillus rhamnosus strain HN001, Lactobacillus rhamnosus strain HN001 produced in a milk-based medium, Lactobacillus reuteri strain DSM 17938, Lactobacillus casei subsp. rhamnosus strain GG, Lactobacillus acidophilus, Lactobacillus lactis, Lactobacillus acetotolerans, Lactobacillus acidifarinae, Lactobacillus acidipisds, Lactobacillus acidophilus, Lactobacillus alimenmrius, Lactobacillus amylolyticus, Lactobacillus amylovorus, Lactobacillus brevis, Lactobacillus buchneri, Lactobacillus cacaonum, Lactobacillus casei subsp. Casei, Lactobacillus collinoides, Lactobacillus composti, Lactobacillus co-ryniformis subsp. Coryniformis, Lactobacillus crispatus, Lactobacillus crustorum, Lactobacillus curvatus subps. Curvatus, Lactobacillus delbrueckii subsp. Bulgaricus, Lactobacillus delbrueckii subsp. Delbrueckii, Lactobacillus delbrueckii subsp. Lactis, Lactobacillus dextrinicus,

*Lactobacillus diolivorans, Lactobacillus fabifermentans, Lactobacillus farciminis, Lactobacillus fermentum, Lactobacillus fructivorans, Lactobacillus frumenti, Lactobacillus gasseri, Lactobacillus ghanensis, Lactobacillus hammesii, Lactobacillus harbinensis, Lactobacillus helveticus, Lactobacillus hilgardii, Lactobacillus homohiochii, Lactobacillus hordei, Lactobacillus jensenii, Lactobacillus johnsonii, Lactobacillus kefiri, Lactobacillus kefuranofadens* subsp. *Kefuranofaciens, Lactobacillus kefuranofadens* subsp. *Kefirgranum, Lactobacillus kimchii, Lactobacillus kisonensis, Lactobacillus mali, Lactobacillus manihotivorans, Lactobacillus mindensis, Lactobacillus mucosae, Lactobacillus nagelii, Lactobacillus namurensis, Lactobacillus nantensis, Lactobacillus nodensis, Lactobacillus oeni, Lactobacillus otakiensis, Lactobacillus panis, Lactobacillus parabrevis, Lactobacillus parabuchneri, Lactobacillus paracasei* subsp. *Paracasei, Lactobacillus parakefiri, Lactobacillus paralimentarius, Lactobacillus paraplantarum, Lactobacillus pentosus, Lactobacillus perolens, Lactobacillus plantarum* subsp. *Plantarum, Lactobacillus pobuzihii, Lactobacillus ponds, Lactobacillus rapi, Lactobacillus reuteri, Lactobacillus rhamnosus, Lactobacillus rossiae, Lactobacillus sakei* subsp *carnosus, Lactobacillus sakei* subsp. *Sakei, Lactobacillus sali varius* subsp. *Salivarius, Lactobacillus sanfranciscensis, Lactobacillus satsumensis, Lactobacillus secaliphilus, Lactobacillus senmaizukei, Lactobacillus siliginis, Lactobacillus spicheri, Lactobacillus suebicus, Lactobacillus sunkii, Lactobacillus tucceti, Lactobacillus vacdnosterrus, Lactobacillus versmnoldensis*, and *Lactobacillus yamanashiensis*.

In another embodiment, the bacteria are from the genus *Lactococcus*, including but not limited to, *Lactococcus Schleifer, Lactococcus chungangensis, Lactococcus fujiensis, Lactococcus garvieae, Lactococcus lactis, Lactococcus lactis* subsp. *Cremoris, Lactococcus lactis* subsp. *Hordniae, Lactococcus lactis* subsp. *Lactis, Lactococcus lactis* subsp. *Tructae, Lactococcus piscium, Lactococcus plantarum*, and *Lactococcus raffinolacti*.

In another embodiment, the bacteria are a population of bacteria classified as "generally regarded as safe" (GRAS) in the genus *Lactococcus*, including but not limited to, *Lactococcus lactis* subsp. *Cremoris, Lactococcus lactis* subsp. *lactis*, and *Lactococcus raffinolactis*.

In another embodiment, the bacteria are from the genus *Enterococcus*, including but not limited to, the GRAS bacteria species *Enterococcus durans, Enterococcus faecalis*, and *Enterococcus faecium*.

In another embodiment, the bacteria are from the genus *Tetragenococcus*, including but not limited to, *Tetragenococcus halophilus* and *Tetragenococcus koreensis*.

In another embodiment, the bacteria are from the genus *Weissella*, including but not limited to, the GRAS bacteria species *Weissella koreensis, Weissella paramesenteroides, Weissella thailandensis, Weissella confusa, Weissella beninensis, Weissella cibaria, Weissella fabaria, Weissella ghanensis*, and *Weissella hellenica*.

In another embodiment, the bacteria are from the genus *Leuconostoc*, including but not limited to, the GRAS bacteria species *Leuconostoc carnosum, Leuconostoc citreum, Leuconostoc fallax, Leuconostoc holzapfelii, Leuconostoc inhae, Leuconostoc kimchii, Leuconostoc lactis, Leuconostoc mesenteroides* subsp. *Cremoris, Leuconostoc mesenteroides* subsp. *Dextranicum, Leuconostoc mesenteroides* subsp. *Mesenteroides, Leuconostoc palmae*, and *Leuconostoc pseudomesenteroides*.

In another embodiment, the bacteria are from the genus *Oenococcus*, including but not limited to, *Oenococcus oeni*.

In another embodiment, the bacteria are from the genus *Salinicoccus*, including but not limited to, *Salinicoccus Ventosa, Salinicoccus albus, Salinicoccus alkaliphilus, Salinicoccus carnicancri, Salinicoccus halodurans, Salinicoccus hispanicus, Salinicoccus iranensis, Salinicoccus jeotgali, Salinicoccus kunmingensis, Salinicoccus luteus, Salinicoccus qingdaonensis, Salinicoccus roseus, Salinicoccus salsiraiae, Salinicoccus sesuvii*, and *Salinicoccus siamensis*.

In another embodiment, the bacteria are from the genus of *Macrococcus*, including but not limited to, *Macrococcus caseolyticus*.

In another embodiment, the bacteria are from the order Bacillales, including but not limited to, the GRAS bacteria species *Bacillus amyloliquefaciens, Bacillus coagulans*, and *Bacillus subbtilis*.

In another embodiment, the bacteria in the population are not *Finegoldia magna*.

In another embodiment, the bacteria are from the genus of *Anaerococcus*, including but not limited to, the species *Anaerococcus hydrogenalis, Anaerococcus lactolyticus, Anaerococcus murdochii, Anaerococcus octavius, Anaerococcus prevotii, Anaerococcus tetradius*, and *Anaerococcus vaginalis*.

In another embodiment, the bacteria are from the genus of *Peptoniphilus*, including but not limited to, the species *Peptoniphilus asaccharolyticus, Peptoniphilus coxii, Peptoniphilus duerdenii, Peptoniphilus gorbachii, Peptoniphilus harei, Peptoniphilus indolicus, Peptoniphilus ivorii, Peptoniphilus koenoeneniae, Peptoniphilus lacrimalis, Peptoniphilus methioninivorax, Peptoniphilus olsenii*, and *Peptoniphilus tyrrelliae*.

In another embodiment, the bacteria are from the genus of *Enhydrobacter*, including but not limited to, the species *Enhydrobacter aerosaccus*.

In another embodiment, the bacteria are from the genus of *Sphingomonas*, including but not limited to, the species *Sphingomonas abaci, Sphingomonas adhaesiva, Sphingomonas aerolata, Sphingomonas aestuarii, Sphingomonas alaskensis, Sphingomonas alpine, Sphingomonas aquatilis, Sphingomonas aromaticivorans, Sphingomonas asaccharolytica, Sphingomonas astaxanthinifaciens, Sphingomonas aurantiaca, Sphingomonas azotifigens, Sphingomonas capsulate, Sphingomonas changbaiensis, Sphingomonas chlorophenolica, Sphingomonas chungbukensis, Sphingomonas cloacae, Sphingomonas cynarae, Sphingomonas desiccabilis, Sphingomonas dokdonensis, Sphingomonas echinoides, Sphingomonas endophytica, Sphingomonas faeni, Sphingomonas fennica, Sphingomonas formosensis, Sphingomonas ginsengisoli, Sphingomonas ginsenosidimutans, Sphingomonas glacialis, Sphingomonas haloaromaticamans, Sphingomonas hankookensis, Sphingomonas herbicidovorans, Sphingomonas histidinilytica, Sphingomonas indica, Sphingomonas insulae, Sphingomonas japonica, Sphingomonas jaspsi, Sphingomonas jejuensis, Sphingomonas jinjuensis, Sphingomonas kaistensis, Sphingomonas koreensis, Sphingomonas laterariae, Sphingomonas leidyi, Sphingomonas macrogolitabida, Sphingomonas macrogoltabidus, Sphingomonas mali, Sphingomonas melonis, Sphingomonas molluscorum, Sphingomonas mucosissima, Sphingomonas natatoria, Sphingomonas oligophenolica, Sphingomonas oryziterrae, Sphingomonas panni, Sphingomonas parapaucimobilis, Sphingomonas paucimobilis, Sphingomonas phyllosphaerae, Sphingomonas pituitosa, Sphingomonas polyaromaticivorans, Sphingomonas pruni, Sphingomonas pseudosanguinis, Sphingomonas rosa, Sphingomonas roseiflava, Sphingomonas rubra, Sphin-* gomonas sanguinis, Sphingomonas sanxanigenens, Sphingomonas sediminicola, Sphingomonas soli, Sphingomonas starnbergensis, Sphingomonas stygia, Sphingomonas subarctica, Sphingomonas suberifaciens, Sphingomonas subterranean, Sphingomonas taejonensis, Sphingomonas terrae, Sphingomonas trueperi, Sphingomonas ursincola, Sphingomonas wittichii, Sphingomonas xenophaga, Sphingomonas xinjiangensis, Sphingomonas yabuuchiae, Sphingomonas yanoikuyae, and Sphingomonas yunnanensis.

In another embodiment, the bacteria are GRAS species in the gamma-proteobacteria phylum, such as Halomonas elongata, Hafnia alvei, excluding Hafnia alvei.

In another embodiment, the bacteria are from the genus of Alpha-proteobacteria phylum, including but not limited to, the GRAS species Acetobacter aceti subsp. Aceti, Acetobacter fabarum, Acetobacter lovaniensis, Acetobacter malorum, Acetobacter orientalis, Acetobacter pasteurianus subsp. Pasteurianus, Acetobacter pomorum, Acetobacter syzygii, Acetobacter tropicalis Gluconacetobacter azotocaptans, Gluconacetobacter diazotrophicus, Gluconacetobacter entanii, Gluconacetobacter europaeus, Gluconacetobacter hansenii, Gluconacetobacter johannae, Gluconacetobacter oboediens, Gluconobacter oxydans, and Gluconacetobacter xylinus.

In another embodiment, the bacteria are Zymomonas mobilis subsp. Mobilis.

In another embodiment, the bacteria are from the Bacteriodetes phylum, including but not limited to, Bacteriodes xylanisolvens strain DSM 23964.

In another embodiment, the bacteria are from the genus of Bifidobacterium, including but not limited to, Bifidobacterium adolescentis, Bifidobacterium adolescentis ATCC 15703, Bifidobacterium adolescentis L2-32, Bifidobacterium angulatum, Bifidobacterium, angulatum DSM 20098=JCM 7096, Bifidobacterium animalis, Bifidobacterium animalis subsp. Animalis, Bifidobacterium animalis subsp. animalis ATCC 25527, Bifidobacterium animalis subsp. Lactis, Bifidobacterium animalis subsp. lactis AD011, Bifidobacterium animalis subsp. lactis ATCC 27673, Bifidobacterium animalis subsp. lactis B420, Bifidobacterium animalis subsp. lactis BB-12, Bifidobacterium animalis subsp. lactis Bi-07, Bifidobacterium animalis subsp. lactis BI-04, Bifidobacterium animalis subsp. lactis BLC1, Bifidobacterium animalis subsp. lactis BS 01, Bifidobacterium animalis subsp. lactis CNCM I-2494, Bifidobacterium animalis subsp. lactis DSM 10140, Bifidobacterium animalis subsp. lactis HN019, Bifidobacterium animalis subsp. lactis V9, Bifidobacterium asteroids, Bifidob acterium asteroides PRL2011, Bifidobacterium biavatfii, Bifidobacterium bifidum, Bifidobacterium bifidum ATCC 29521=JCM 1255, Bifidobacterium bifidum BGN4, Bifidobacterium bifidum CECT 7366, Bifidobacterium bifidum DSM 20215, Bifidobacterium bifidum IPLA 20015, Bifidobacterium bifidum JCM 1254, Bifidobacterium bifidum L MG 13195, Bifidobacterium bifidum NCIMB 41171, Bifidobacterium bifidum PRL2010, Bifidobacterium bifidum S17, Bifidobacterium bombi, Bifidobacterium boum, Bifidobacterium breve, Bifidobacterium breve ACS-071-V-Sch8b, Bifidobacterium breve CECT 7263, Bifidobacterium breve DPC 6330, Bifidobacterium breve DSM 20213=JCM 1192, Bifidobacterium breve EX336960VC18, Bifidobacterium breve EX336960VC19, Bifidobacterium breve EX336960VC21, Bifidobacterium breve EX533959VC21, Bifidobacterium breve HPH0326, Bifidobacterium breve JCP7499, Bifidobacterium breve S27, Bifidobacterium breve UCC2003, Bifidobacterium callitrichos, Bifidobacterium catenulatum, Bifidobacterium catenulatum DSM 16992=JCM 1194, Bifidobacterium choerinum, Bifidobacterium choerinum DSM 20434, Bifidobacterium coagulans, Bifidobacterium indicum, Bifidobacterium kashiwanohense, Bifidobacterium kashiwanohense JCM 15439, Bifidobacterium longum, Bifidobacterium longum 3_1_37DFAAB, Bifidobacterium longum AGR2137, Bifidobacterium longum BORI, Bifidobacterium longum D2957, Bifidobacterium longum DJO10A, Bifidobacterium longum NCC2705, Bifidobacterium longum subsp. Infantis, Bifidobacterium longum subsp. infantis 157F, Bifidobacterium longum subsp. infantis ATCC 15697=JCM 1222, Bifidobacterium longum subsp. infantis CCUG 52486, Bifidobacterium longum subsp. Longum, Bifidobacterium longum subsp. longum 1-6B, Bifidobacterium longum subsp. longum 2-2B, Bifidobacterium longum subsp. longum 35B, Bifidobacterium longum subsp. longum 44B, Bifidobacterium longum subsp. longum ATCC 55813, Bifidobacterium longum subsp. longum BBMN68, Bifidobacterium longum subsp. longum CECT 7347, Bifidobacterium longum subsp. longum CMCC P0001, Bifidobacterium longum subsp. longum F8, Bifidobacterium longum subsp. longum JCM 1217, Bifidobacterium longum subsp. longum JDM301, Bifidobacterium longum subsp. longum KACC 91563, Bifidobacterium longum subsp. Suis, Bifidobacterium magnum, Bifidobacterium magnum DSM 20222, Bifidobacterium coryneforme, Bifidobacterium crudilactis, Bifidobacterium cuniculi, Bifidobacterium dentium, Bifidobacterium dentium ATCC 27678, Bifidobacterium dentium ATCC 27679, Bifidobacterium dentium Bd1, Bifidobacterium dentium JCM 1195, Bifidobacterium dentium JCVIHMP022, Bifidobacterium gallicum, Bifidobacterium gallicum DSM 20093, Bifidobacterium gallinarum, Bifidobacterium simiae, Bifidobacterium stellenboschense, Bifidobacterium stercoris, Bifidobacterium subtile, Bifidobacterium subtile DSM 20096. Bifidobacterium merycicum, Bifidobacterium minimum, Bifidobacterium minimum DSM 20102, Bifidobacterium mongoliense, Bifidobacterium pseudocatenulatum, Bifidobacterium pseudocatenulatum D2CA, Bifidobacterium pseudocatenulatum DSM 20438=JCM 1200, Bifidobacterium pseudolongum, Bifidobacterium pseudolongum AGR2145, Bifidobacterium pseudolongum subsp. Globosum, Bifidobacterium pseudolongum subsp. Pseudolongum, Bifidobacterium psychraerophilum, Bifidobacterium pullorum, Bifidobacterium pullorum ATCC 49618, Bifidobacterium reuteri, Bifidobacterium ruminantium, Bifidobacterium saeculare, Bifidobacterium saguini, Bifidobacterium scardovii, Bifidobacterium scardovii JC M 12489, Bifidobacterium thermacidophilum, Bifidobacterium thermacidophilum subsp. Porcinum, Bifidobacterium thermacidophilum subsp. Thermacidophilum, Bifidobacterium thermophilum, Bifidobacterium thermophilum RBL67, Bifidobacterium tsurumiense, Bifidobacterium tsurumiense DSM 17777, Bifidobacterium sp. Bifidobacterium breve M-16V, Bifidobacterium animalis subsp. lactis strains HN019, Bi-07, BI-04 and B420, Bifidobacterium animalis subsp. lactis strain Bf-6, Bifidobacterium longum strain BB536, and Bifidobacterium lactis strain Bb12.

In another embodiment, the bacteria are from the genus of Carnobacterium, including but not limited to, Carnobacterium alterfunditum, Carnobacterium divergens, Carnobacterium funditum, Carnobacterium gallinarum, Carnobacterium inhibens, Carnobacterium jeotgali, Carnobacterium maltaromaticum, Carnobacterium maltaromaticum 38b, Carnobacterium maltaromaticum ATCC 35586, Carnobacterium maltaromaticum LMA28, Carnobacterium mobile, Carnobacterium pleistocenium, Carnobacterium viridians, Carnobacterium sp., Carnobacterium sp. 'eilaticum 021211', *Carnobacterium* sp. 11-1, *Carnobacterium* sp. 12266/2009, *Carnobacterium* sp. 13-3, *Carnobacterium* sp. 17-4, *Carnobacterium* sp. 22-6, *Carnobacterium* sp. 2673, *Carnobacterium* sp. 27L, *Carnobacterium* sp. 35L, *Carnobacterium* sp. 37-3-1, *Carnobacterium* sp. 38ANAV, *Carnobacterium* sp. 40L, *Carnobacterium* sp. 7196, *Carnobacterium* sp. A, *Carnobacterium* sp. A2S10L14, *Carnobacterium* sp. A4, *Carnobacterium* sp. A726, *Carnobacterium* sp. cG53, *Carnobacterium* sp. ARCTIC-P2, *Carnobacterium* sp. ARCTIC-P26, *Carnobacterium* sp. ARCTIC-P35, *Carnobacterium* sp. AT12, *Carnobacterium* sp. AT7, *Carnobacterium* sp. B, *Carnobacterium* sp. B5, *Carnobacterium* sp. BA-81, *Carnobacterium* sp. BBDP54, *Carnobacterium* sp. BBDP71, *Carnobacterium* sp. BM-8, *Carnobacterium* sp. BM-81, *Carnobacterium* sp. C-13, *Carnobacterium* sp. c58, *Carnobacterium* sp. cG53, *Carnobacterium* sp. CM1, *Carnobacterium* sp. D35, *Carnobacterium* sp. D4, *Carnobacterium* sp. D5, *Carnobacterium* sp. EK-153, *Carnobacterium* sp. ES-11, *Carnobacterium* sp. FBT1-19, *Carnobacterium* sp. FBT1-22, *Carnobacterium* sp. FBT3-14, *Carnobacterium* sp. FBT3-9, *Carnobacterium* sp. FBT4-1, *Carnobacterium* sp. FBT4-18, *Carnobacterium* sp. G1516J1L, *Carnobacterium* sp. G4a-1, *Carnobacterium* sp. G5a-1, *Carnobacterium* sp. GCM1, *Carnobacterium* sp. H126a, *Carnobacterium* sp. Hg-4-03, *Carnobacterium* sp. I-Bh20-14, *Carnobacterium* sp. I-Bh-4-26, *Carnobacterium* sp. KA-2, *Carnobacterium* sp. KA-8, *Carnobacterium* sp. KH1, *Carnobacterium* sp. KOPR180142, *Carnobacterium* sp. KOPR180153, *Carnobacterium* sp. KOPR180155, *Carnobacterium* sp. L02-6127, *Carnobacterium* sp. LIV10, *Carnobacterium* sp. LMG 26642, *Carnobacterium* sp. LV62:W1, *Carnobacterium* sp. LV66, *Carnobacterium* sp. M7-C10, *Carnobacterium* sp. MARL15, *Carnobacterium* sp. MKJ37, *Carnobacterium* sp. NFU35-25, *Carnobacterium* sp. NJ-46, *Carnobacterium* sp. R-36982, *Carnobacterium* sp. R1234, *Carnobacterium* sp. S171, *Carnobacterium* sp. S181, *Carnobacterium* sp. Sd5t18, *Carnobacterium* sp. Sd5t5, *Carnobacterium* sp. Sd6t1, *Carnobacterium* sp. Sd6t15, *Carnobacterium* sp. Sd6t17, *Carnobacterium* sp. Sd6t18, *Carnobacterium* sp. SR2-31-l, *Carnobacterium* sp. St2, *Carnobacterium* sp. T301, *Carnobacterium* sp. U149, *Carnobacterium* sp. UPAA77, *Carnobacterium* sp. UST050418-652, *Carnobacterium* sp. WFPIS001, *Carnobacterium* sp. WN1359, *Carnobacterium* sp. WN1370, *Carnobacterium* sp. WN1371, *Carnobacterium* sp. WN1372, *Carnobacterium* sp. WN1373, *Carnobacterium* sp. WN1374, *Carnobacterium* sp. Y6, *Carnobacterium divergens*, *Carnobacterium maltaromaticum*, *Carnobacterium piscicola*, *Carnobacterium maltaromaticum* strain CB1 (viable and heat-treated), and *Carnobacterium maltaromaticum* strain CB1.

In another embodiment, the bacteria are from the genus of *Pediococcus*, including but not limited to, *Pediococcus acidilactici*, *Pediococcus acidilactici* 7_4, *Pediococcus acidilactici* D3, *Pediococcus acidilactici* DSM 20284, *Pediococcus acidilactici* MA18/5M, *Pediococcus argentinicus*, *Pediococcus cellicola*, *Pediococcus claussenii*, *Pediococcus claussenii* ATCC BAA-344, *Pediococcus damnosus*, *Pediococcus damnosus* 9-6b, *Pediococcus ethanolidurans*, *Pediococcus inopinatus*, *Pediococcus lolii*, *Pediococcus lolii* NGRI 0510Q, *Pediococcus parvulus*, *Pediococcus parvulus* CIRM 750, *Pediococcus pentosaceus*, *Pediococcus pentosaceus* ATCC 25745, *Pediococcus pentosaceus* IE-3, *Pediococcus siamensis*, *Pediococcus stilesii*, *Pediococcus* sp. 14.8.17, *Pediococcus* sp. BGM59, *Pediococcus* sp. BZ-2005, *Pediococcus* sp. CAT-100BC, *Pediococcus* sp. CR-6S, *Pediococcus* sp. CRA51, *Pediococcus* sp. EDB-L14, *Pediococcus* sp. epsi2-MSE-E3-2, *Pediococcus* sp. epsi31-MSE-E3-2, *Pediococcus* sp. FUA 3137, *Pediococcus* sp. FUA 3140, *Pediococcus* sp. FUA 3226, *Pediococcus* sp. GS4, *Pediococcus* sp. IBUN 186, *Pediococcus* sp. IE3, *Pediococcus* sp. IJ-K1, *Pediococcus* sp. J-11, *Pediococcus* sp. KDLLL3-1, *Pediococcus* sp. L04, *Pediococcus* sp. LAB4012, *Pediococcus* sp. Lact10, *Pediococcus* sp. LQC 1953, *Pediococcus* sp. LQC 1957, *Pediococcus* sp. LQC 1963, *Pediococcus* sp. LQC 1966, *Pediococcus* sp. LQC 1972, *Pediococcus* sp. MB2C, *Pediococcus* sp. MB2D, *Pediococcus* sp. MFC1, *Pediococcus* sp. MMZ60A, *Pediococcus* sp. MUU10, *Pediococcus* sp. MUU13, *Pediococcus* sp. MUU2, *Pediococcus* sp. MUU3, *Pediococcus* sp. MUU4, *Pediococcus* sp. NBRC 106004, *Pediococcus* sp. NBRC 106014, *Pediococcus* sp. NBRC 106015, *Pediococcus* sp. NBRC 106028, *Pediococcus* sp. NBRC 106032, *Pediococcus* sp. NBRC 107178, *Pediococcus* sp. NBRC 107186, *Pediococcus* sp. NBRC 107193, *Pediococcus* sp. NBRC 107213, *Pediococcus* sp. NBRC 107218, *Pediococcus* sp. NBRC 107221, *Pediococcus* sp. NBRC 107222, *Pediococcus* sp. NBRC 107244, *Pediococcus* sp. NBRC 107250, *Pediococcus* sp. NBRC 107256, *Pediococcus* sp. NBRC 107260, *Pediococcus* sp. NBRC 107264, *Pediococcus* sp. NBRC 107299, *Pediococcus* sp. NBRC 107306, *Pediococcus* sp. NBRC 107309, *Pediococcus* sp. NBRC 107310, *Pediococcus* sp. NBRC 107331, *Pediococcus* sp. NBRC 107343, *Pediococcus* sp. NBRC 107346, *Pediococcus* sp. NBRC 107350, *Pediococcus* sp. NIR1, *Pediococcus* sp. NIR3, *Pediococcus* sp. omega41-FH-E3-2, *Pediococcus* sp. P14, *Pediococcus* sp. Pom3, *Pediococcus* sp. Pom4, *Pediococcus* sp. Pom7, *Pediococcus* sp. Pov5, *Pediococcus* sp. Pov7, *Pediococcus* sp. Pov8, *Pediococcus* sp. QCH-42, *Pediococcus* sp. QCH-66, *Pediococcus* sp. QCH-67, *Pediococcus* sp. QMA-03G, *Pediococcus* sp. QMA-06CH, *Pediococcus* sp. QMA-07G, *Pediococcus* sp. QMA-11, *Pediococcus* sp. QMA-21BC, *Pediococcus* sp. QMA-23BC, *Pediococcus* sp. QMA-24BC, *Pediococcus* sp. QMA-27BC, *Pediococcus* sp. Rrt8, *Pediococcus* sp. Rrt9, *Pediococcus* sp. Rrv1, *Pediococcus* sp. Rrv3, *Pediococcus* sp. S17, *Pediococcus* sp. S18, *Pediococcus* sp. SD2, *Pediococcus* sp. Shahsavar, *Pediococcus* sp. siga1, *Pediococcus* sp. T1R1C23, *Pediococcus* sp. T1R4C24, *Pediococcus* sp. Te6, *Pediococcus* sp. YCO-02, *Pediococcus* sp. YCO-04, *Pediococcus* sp. YCO-09, *Pediococcus* sp. YCO-10, *Pediococcus* sp. YCO-11, *Pediococcus* sp. YCO-12, *Pediococcus* sp. YCO-13, *Pediococcus* sp. YCO-16, *Pediococcus* sp. YCO-17, *Pediococcus* sp. YCO-18, *Pediococcus* sp. YCO-23, *Pediococcus* sp. YCO-25, *Pediococcus* sp. YCO-26, *Pediococcus* sp. YCO-28, *Pediococcus* sp. YXC-17, *Pediococcus* sp. Z-17, *Pediococcus acidilactici* strain NP3, *Pediococcus acidilactici*, *Pediococcus acidilactici*, *Pediococcus parvulus*, and *Pediococcus pentosaceus*.

In one embodiment, any bacteria, listed herein or otherwise known that is pathogenic and/or is an opportunistic pathogenic species is excluded. In another embodiment, the bacteria selected for transformation and to be included in the composition is any one of the bacterial genus listed herein or any one of the specific bacterial species listed herein, or any collection of first and second bacteria listed herein.

In one embodiment, the bacterial for use in the composition is any bacteria capable of existing on skin, in particular human skin, and more particularly bacteria that reside on human skin and are GRAS bacteria, excluding pathogenic and/or opportunistic bacteria.

In one embodiment, the composition comprises a population of transformed bacteria and a population of bacteria not transformed to express a compound of interest, e.g., the composition is comprised of a transformed bacteria population and a naturally occurring or probiotic bacteria. Compositions comprising more than one population of bacteria, wherein each population is a collection of individual transformed bacteria for expression of different compounds of interest, as each individual cell able to express more than one compound of interest or each individual cell express one compound, and the collection of different individuals expressing different molecules of interest express different compounds of interest, or wherein one population is transformed and one population is not transformed, are also contemplated. In one embodiment, the composition comprises first and second populations of transformed bacteria formulated for topical application to a subject. In one embodiment, the second population of transformed bacteria is either or both (i) created from a non-pathogenic bacteria that is different from the first population of transformed bacteria in the composition or (ii) transformed to express a compound of interest that is different from the first compound of interest expressed by the first population of transformed bacteria in the composition.

The bacteria may be included in a composition in a live, attenuated, semi-active or inactivated, or dead form. According to one particular embodiment, these bacteria are used in a live form, and are capable of chronically expressing the compound of interest upon topical application of the composition in which they are formulated. They may also be included in the form of cell component fractions or in the form of metabolites. The bacterial species(s), molecule(s) of interest or fraction(s) may also be introduced in the form of a lyophilized powder, of a culture supernatant, of harvested compound, and/or where appropriate, in a concentrated form.

According to one variation, the compositions may also contain a divalent inorganic cation. The compositions may be in any of the galenical forms usually available for the method of administration selected. The active molecule synthesized by the bacteria (which in one embodiment are skin bacteria) could be could either stay in the bacteria or secreted outside to the skin.

Limiting factors can control the bacterial growth. Such limiting factors can exist naturally on the skin and in one embodiment may be included in the composition that is to be applied topically to a subject to be treated. One or more limiting factors may be included in the formulation. In another embodiment the limiting factors are added to complementary products such as soaps, body wash, shampoo, lotion to enrich and nourish the composition, and to keep it active or alive. Examples for limiting factors include amino acids, biotin, nicotinamide and thiamine, pantothenate, riboflavin, folic acid, keratin, lipids, lactate, and melanins. A preferred limiting factor may be the amino acid L-alanin. Bacterial growth can be controlled by the mechanism of origin of replication to limit bacterial cycles. Bacterial cycles can be limited to 50 cycles, or bacterial cycles can be limited to 2-40 cycles. Limitation of bacterial growth can also be achieved by physical environmental factors as pH and temperature.

B. Exemplary Compounds of Interest

As described above, the bacteria species selected for the composition is transformed using known recombinant techniques to express a compound of interest. Exemplary compounds of interest are listed in the table below, along with an indication of the skin disorder or condition or purpose for which the compound is used.

| Purpose of Compound | Active compound |
| --- | --- |
| UV protection (sunscreen; UVA, UVB) | Mycosporine, gadusols, oxo-mycosporines, imino-mycosporines and mycosporine-like amino acids (MAA; glycosylated or covalently bound to oligosaccharides, oligosaccharide-linked MAAs). Intracellular or extracellular. Examples include: gadusol, deoxygadusol, 4-Deoxygadusol (S2), shinorine, porphyra-334, palythine, palythene, asterina-330, palythinol, mycosporine-glycine, mycosporine serinol, mycosporine-taurine, mycosporine-glycine-valine, mycosporine-2-glycine, mycosporine-glycine-glutamic acid, mycosporine-glutamic acid-glycine, mycosporine-methylamine-serine, mycosporine-methylamine-threonine, usujirene, dehydroxylusujirene, playthenic acid-337, playthenic acid-335, palythine-serine, palythine-threonine, palythine-threonine-sulphate, playthine-serine-sulphate, euhalothece, mycosporine-alanine (2-(e)-2,3-dihydroxipro-1-enylimino-mycosporine-alanine), scytonemin<br>Molecules with sequence similarity to MAAs, such as dehydroquinate synthase homolog (DHQS homolog) and ATP-grasp<br>Melamines, including eumelanin-(or dihydroxyphenylalanine (DOPA) melanins), pheomelanin allomelanins, pyomelanine, dopamelanin, neuromelanin<br>UV-screening/observing amino acids-like molecules, such as urocanic acid<br>Flavonoids, Anthocyanines and anthoxantins, and Anthocyanidins<br>Betalanines, such as betacyanin and betaxanthins<br>UV-screening/observing Pigments, such as Carotenoids/cartenoproteins, carotens, lycopene, xanthopylls, lutins, zeaxanthin, porphyrin-based/heme-porphyrin based, chlorophyll-II<br>UV-screening/observing co-factors, such as tetrahydrobiopterin and phenylpropanoids<br>Polyphenol, Tannins, Phlorotannins, dieckol, eckol, Flavan-3-ols or flavanols, pycnogenol<br>sargaquinoic acid, sargachromenol, sphaerophorin (depside) pannarin (depsidone)<br>DNA repair enzymes, that repair damage caused by exposure to UV, like photolyase, endonuclease and DNA glycosylases |
| Psoriasis | Retinoid, Vitamin A, beta-caroten, Vit D and it's derivatives, Anti-inflammatory cytokines such as Interleukin-2 (IL-2) |

-continued

| Purpose of Compound | Active compound |
|---|---|
| Dry Skin | Polymers, such as polyol and glycerol; skin related natural compounds, such as collagen, keratin, elastin, linoleic acid, laminin, tretinoin, tazarotene, sargaquinoic acid, sargachromenol, fucoxanthin, retinoid |
| Relief of oxidative stress caused by UV; Anti-Oxidants, Anti-reactive oxygen species (Anti-ROS)/ Anti-Aging, moisturizing and cosmetics | Tyrosinases (and its substrates and products) alpha hydroxy acids (AHAs), such as glycolic acid, lactic acid and citric acid Polysaccharides; Glycosaminoglycans, (GAGs) or mucopolysaccharides; Hyaluronan (also called hyaluronic acid or hyaluronate or HA) Skin related cofactors, such as Vitamin A, Vitamin C or L-ascorbic acid, or simply ascorbate; Biopterin; Coenzyme A (CoA, CoASH, or HSCoA); Coenzyme Q10, ubiquinone, ubidecarenone, coenzyme Q; CoQ10; Molybdopterin Vitamin E; alpha, beta, gamma, delta-tocopherols and alpha, beta, gamma, delta-tocotrienols Polymers, such as Polyol and Glycerol, Skin related natural compounds, such as collagen, keratin, elastin, linoleic acid, laminin, tretinoin, tazarotene, sargaquinoic acid, sargachromenol, fucoxanthin, retinoid, anti-inflammatory cytokines (such as IL-2), cortisone, tacrolimus, cyclosporine, resveratrol, gallocatechol, gallocatechin, epigallocatechin gallate |
| Eczema | cortisone, tacrolimus, cyclosporine |
| Wound healing/Diabetic wounds/Ulcers | anaerobic bacteria delivering oxygen |
| Intertrigo/diaper rash | talcum, starch |

In one embodiment, a composition for use in protection of skin from ultraviolet radiation is contemplated. That is, the composition is for use as a sunscreen, to absorb or reflect ultraviolet A radiation, typically at a wavelength of between 320-400 nm, ultraviolet B radiation, typically at a wavelength of between 315-280 nm, or both UVA and UVB absorbing and/or reflecting. The transformed bacteria in the composition express one or more of the following exemplary compounds of interest in Group 1, Group 2, Group 3, Group 4, Group 5, Group 6, Group 7, Group 8, Group 9, Group 10, Group 11 and Group 12:

Group 1—mycosporine, gadusols, oxo-mycosporines, imino-mycosporines and mycosporine-like Amino Acids (MAA; glycosylated or covalently bound to oligosaccharides, oligosaccharide-linked MAAs); and/or intracellular or extracellular gadusol, deoxygadusol, 4-Deoxygadusol (S2), shinorine, *porphyra*-334, palythine, palythene, asterina-330, palythinol, mycosporine-glycine, mycosporine serinol, mycosporine-taurine, mycosporine-glycine-valine, mycosporine-2-glycine, mycosporine-glycine-glutamic acid, mycosporine-glutamic acid-glycine, mycosporine-methylamine-serine, mycosporine-methylamine-threonine, usujirene, dehydroxylusujirene, playthenic acid-337, playthenic acid-335, palythine-serine, palythine-threonine, palythine-threonine-sulphate, playthine-serine-sulphate, euhalothece, mycosporine-alanine (2-(e)-2,3-dihydroxipro-1-enylimino-mycosporine-alanine);

Group 2—Scytonemin;

Group 3—Melanines: eumelanin- (or dihydroxyphenyl-alanine (DOPA) melanins), pheomelanin allomelanins, pyomelanine, dopamelanin, neuromelanin;

Group 4—UV-screening/observing amino acids-like molecules: urocanic acid;

Group 5—Flavonoids: Anthocyanines and anthoxantins, Anthocyanidins;

Group 6—Betalanines: betacyanin, betaxanthins;

Group 7—Molecules with sequence similarity to MAAs: dehydroquinate synthase homolog (DHQS homolog), ATP-grasp;

Group 8—UV-screening/observing pigments: Carotenoids/cartenoproteins, carotens, lycopene, Xanthopylls, lutins, zeaxanthin, porphyrin-based/heme-porphyrin based, chlorophyll-II;

Group 9—UV-screening/observing co-factors, such as tetrahydrobiopterin and biopterin;

Group 10—Phenylpropanoids;

Group 11—Tannins: Phlorotannins, dieckol, eckol; and

Group 12—Sargaquinoic acid, sargachromenol, sphaerophorin (depside), pannarin (depsidone);

Group 13—DNA repair enzymes that repair damage caused by exposure to UV, such as photolyase, endonuclease, and DNA glycosylase.

In one embodiment, the compound of interest is any one of the compounds listed in any one of Groups 1-13 alone.

In another embodiment, a composition for use in providing relief of oxidative stress is contemplated, for use as a cosmetic or anti-aging composition. The composition may provide relief form UV exposure, as an anti-oxidant composition. The transformed bacteria in the composition express one or more of the following exemplary compounds of interest in Group 1, Group 2, Group 3, Group 4, Group 5, Group 6 and Group 7:

Group 1—Tyrosinases (and its substrates and products);

Group 2—Alpha hydroxy acids (AHAs): Glycolic acid, lactic acid, and citric acid;

Group 3—Polysaccharides: glycosaminoglycans, (GAGs), mucopolysaccharides, hyaluronan (also called hyaluronic acid or hyaluronate or HA);

Group 4—Skin related cofactors: Vitamin C or L-ascorbic acid, or simply ascorbate, Vitamin A, Biopterin, Coenzyme A (CoA, CoASH, or HSCoA), Coenzyme Q10 (ubiquinone, ubidecarenone, coenzyme Q, CoQ10), Molybdopterin;

Group 5—Vitamin E: alpha, beta, gamma, delta-tocopherols, alpha, beta, gamma, delta-tocotrienols;

Group 6—Polymers: Polyol, Glycerol;

Group 7—Additional skin related natural compounds, such as collagen, keratin, elastin, linoleic acid, laminin, tretinoin, tazarotene, sargaquinoic acid, sargachromenol, fucoxanthin, retinoid, anti-inflammatory cytokines (such as IL-2), cortisone, tacrolimus, ciclosporin, resveratrol, gallocatechol, gallocatechin, and epigallocatechin gallate.

In other embodiments, a composition for use in treating active dermatitis, acne, burns, insect bites, hives, dandruff and body odor is contemplated. A person of skill in the art can identify compounds of interest to be expressed in the transformed bacteria for treatment of these conditions.

Compounds having sequence similarity to the sequences of the compounds listed in the table above are also contemplated and may be regarded as identical compounds. Two sequences are said to be "substantially identical and identical" if the sequence of nucleotides or amino acid residues, respectively, in the two sequences has similarity of at least 40%, when aligned for maximum correspondence as described below. Alternatively, percent identity can be any integer from 20% to 100%. More preferred embodiments include at least: 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98 or 99% compared to a reference sequence (e.g., SEQ ID NO:1, 2, 3, 4, 5, 6, 7, 8, 9, 10, 11, 12, 13, 14, 18) using the programs described herein, such as BLAST using standard parameters, as described below. This definition also refers to the complement of a test sequence, when the test sequence has substantial identity to a reference sequence.

Compounds having a conserved protein domain with sequence similarity to the sequences of the domains of the proteins of the compounds listed in the table above, are also contemplated and may be regarded as identical compounds.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Methods of alignment of sequences for comparison are well-known in the art. As the use of the following programs (provided by the National Center for Biotechnology Information) may be used to determine homologies/identities: BLAST, gapped BLAST, BLASTN and PSI-BLAST, which may be used with default parameters. Optimal alignment of sequences for comparison can be conducted by different methods known in the art, such as, but not limited to, the algorithms of Waterman, Needleman, Pearson, or by manual alignment and visual inspection.

Because of the degeneracy of the genetic code, a large number of functionally identical nucleic acids encode any given protein. One of skill will recognize the individual codon usage to a nucleic acid, peptide, polypeptide, or protein sequence that alters, adds or deletes a single amino acid or a small percentage of amino acids in the encoded sequence to allow the coding of the compound of interest.

It will be appreciated that the composition can be used in combination with existing topical compositions intended for treatment of the same or another disorder or condition. For example, the composition described herein for use as a sunscreen may be used in combination with a known sunscreen product, including: titanium dioxide ($TiO_2$), zinc oxide (ZnO), para-aminobenzoic acid, avobenzone, butyl methoxydibenzoylmethane, ensulizole, 2-phenylbenzimidazole-5-sulfonic acid, homosalate, homomethylsalicylat, meradimate, menthyl 2-minobenzoate, menthylanthranilate, octinoxate, menthyl 2-minobenzoate menthylanthranilate, octisalate, 2-ethylhexyl salicylate, octyl salicylate, octocrylene, 2-ethylhexyl-2-cyano-3,3 diphenylacrylate, oxybenzone, benzophenone-3,2-hydroxy-4-methoxybenzophenone, sulisobenzone, benzophenone-4, drometrizoletrisiloxane, mexoryl XL, enzacamene, 4-Methylbenzylidene camphor, padimate-O, octyl dimethyl PABA, σ-PABA, terephthalylidene dicamphor sulfonic acid, mexoryl SX, 3,3'-(1,4-phenylenedimethylidene) bis[7,7-dimethyl-2-oxobicylclo[2.2.1]hept-1-yl methanesulfonic acid), cinoxate, 2-ethoxyethyl 3-(4-methoxyphenyl)propenoate, diethanolamine-methoxycinnamate, dioxybenzone, benzophenone-8, (2-hydroxy-4-methoxyphenyl)-(2-hydroxyphenyl)methanone, triethanolamine salicylate, and trolamine salicylate.

Nucleic acid sequences coding for the compound of interest can be identified by those of skill in the art, and several examples are set forth herein as:

SEQ ID NO:1 DNA sequence for shinorine operon;
SEQ ID NO:2 DNA sequence for shinorine *nostoc;*
SEQ ID NO:3 AA sequence for Amino acid adenylation_Ava_3855;
SEQ ID NO:4 AA sequence for ATP-grasp enzyme-like protein_Ava_3856;
SEQ ID NO:5 AA sequence for O-methyltransferase, family 3_Ava_3857;
SEQ ID NO:6 AA sequence for 3-dehydroquinate synthase_Ava_3858;
SEQ ID NO:7 DNA Ava_3858_3_dehydroquinate synthase;
SEQ ID NO:8 DNA spacer1_4804128_4803953;
SEQ ID NO:9 DNA Ava_3857_O-methyltransferase;
SEQ ID NO:10 DNA spacer2_4803114_4803099;
SEQ ID NO:11 DNA Ava_3856_ATP-grasp enzyme-like protein;
SEQ ID NO:12 DNA Spacer3_4804128_4803953;
SEQ ID NO:13 DNA Ava_3855_Amino acid adenylation;
SEQ ID NO:16 DNA forward_primer_for shinorine_operon;
SEQ ID NO:17 DNA reverse_primer_for shinorine_operon; and
SEQ ID NO:18 DNA sequence for tyrosynase.

C. Recombinant Molecular Techniques

Techniques for transformation of any of the bacterial species listed herein or otherwise known in the art are understood by skilled artisans. Several techniques are briefly described herein, and factors to consider in such techniques are now discussed, including 1. Modular organization; 2. Vector types; 3. Expression and improving impression techniques; 4. Expression of insert and validation; and 5. Transformation.

1. Modular Organization

The transformed bacterial strains can be regarded as cell factory, or vehicles, producing by any method known in the art recombinant proteins (U.S. Pat. No. 4,259,444, incorporated by reference herein), and would typically include cloning of the isolated nucleic acid molecule that encodes for the compound of interest into an appropriate vector. The expression vector is built in a modular organization, allowing independent design of each component in separate conditions and an easy exchange of all essential elements. In such a modular vector the essential elements typically include: replicon, promoter (constitutive or inducible with regulation system), gene of interest, marker or reporter, resistance or limiting factor, Multiple cloning site (MCS), shine-delgarno (ribosomal binding site), and terminators, as shown in several systems, as the NICE system (Mierau I and Kleerebezem M., *Appl Microbiol Biotechnol.* 68:705-17 (2005), or based on cryptic plasmids (Shareck J. et al., *Crit. Rev Biotechnol.* 24:155-208 (2004).

Suitable vectors can be chosen or constructed, containing appropriate regulatory sequences, including promoter sequences, terminator fragments, polyadenylation sequences, enhancer sequences, and other sequences as appropriate. Additional sequences may be added as described above which sequences include a ribosome binding site and a translation start codon.

Appropriate bacterial expression vectors are known to the person skilled in the art as described in Molecular Cloning: a Laboratory Manual: 2nd edition, Sambrook et al., 1989, Cold Spring Harbor Laboratory Press, and there are several studies shown expression vectors for LAB strains, as by Wang T. T. and Lee B. H., *Plasmids in Lactobacillus. Crit. Rev Biotechnol.* 17:227-72 (1997), and specifically in the food industry by Nguyen T. T. et al., *J Agric Food Chem.* 59:5617-24 (2011).

Exemplary essential building blocks of a vector are listed in the table below, allowing modular configuration of a backbone plasmid, with different combinations, for a suitable expression of the molecule of interest:

| Replicon | Promoter-inducible (inducer) | Promoter-constitutive | Marker or reporter | Terminator |
|---|---|---|---|---|
| Ori + repA, p15A, p353-1, p353-2, p8014-2, pA1-derived, pAI, pAM-beta-1, pBG10, pBM02, pC194, pCI305, pCI528, pD125, pFX1/3, pG+, pGK12, pGT633, pLA106, pLAB1000, pLB10, pLC2, pLF1311, pLJ1, pLP1, pLP825, pLPE323, pLUL631, pND302, pND324, pOri+, pPM4, pPSC, pPSC20/22, pSH71, pSK11L, pVS40, pWC1, pWS97, pWV01, pWV02, rep256, repD + E | Bacteriocin, dnaJ (from usp45; High Temp), FOS, gadC-GdR (low pH), grac-lac (IPTG), lacA/lacC/lacR (Lactose), lacA/T7 (Lactose), lacF, (Lactose), lacG, lacS-GalR (Lactose), lacZ, NICE system, nisA/F/R/K/P (Nisin), orfX of sakacin Pregulon, PA170 (low pH, low temp.), pgm, phi31 (and ori; phi infection), Porf1, Porf330, PorfX, PpfkA, prtP or ptrM (absence of peptides), PsapA, PsapA (sakacin A), PsapiP, PslpA, PspplP (Sakacin P), PsspA, PsspQ, Ptuf (CDM), Pusp45, rep/op phi rlt (Mitomycin C), repressor/operator phirlt (Mytomycin C), sodA (Aeration), tec-Rro12 (high temp), hyA, tre, trpE (absence of tryptophan), xylA (Xylose) | PermB, PldhL, P1 (SPL), P10 (SPL), P11 (SPL), P13 (SPL), P14 (SPL), P15 (SPL), P16 (SPL), P17 (SPL), P20 (SPL), P21, P21 (SPL), P22 (SPL), P23, P23 (SPL), P25 (SPL), P27 (SPL), P29 (SPL), P3 (SPL), P30 (SPL), P31 (SPL), P32 (weak), P33 (SPL), P34 (SPL), P35 (SPL), P38 (SPL), P4 (SPL), P40 (SPL), P41 (SPL), P42 (SPL), P43 (SPL), P44 (SPL), P44 (weak), P46 (SPL), P47 (SPL), P48(SPL), P5 (SPL), P59, P6 (SPL), P8 (SPL), P9 (SPL), Pami, Ppgm, Pspac, Pveg, PrRNA1-a, PrRNA1-b, PrRNA2-b, PrRNA3-a, PrRNA3-b, PrRNA4-a, PrRNA4-b, PrRNA5-a, PrRNA5-b, Pslp | cml-chloramphenicol, (alr) alanin racemase gene, Abr, amp (Ap)-ampicillin, amyS, ccpA, cloxacillin, Cmr, ermL, ery/em-erythromycin resistance marker, estA, genes for TTFC, gentamycin, GusA (beta-glucuronidas), Kanamycin, LacZ, luxAB, msmR, neomycin, nisI, nsr, penicillin, PepN (aminopeptidase N), pepO, ptsH, streptomycin, tetracycline | LacZ terminator, lollypop structure, T1T2, Tcat194, term667, term908, TpepA, TpepN, TsaiA |

The modular organization is a construct that is capable of expression of the coding sequence by the bacterial host cell. In particular such a vector is either an expression vector or a chromosomal integration vector, such as for example described in Steidler L. et al., Nature Biotechnology, 21(7): 785-789 (2003), or by Pérez-Arellano I. et al., *Plasmid* 46:106-16 (2001).

Figure 1B:
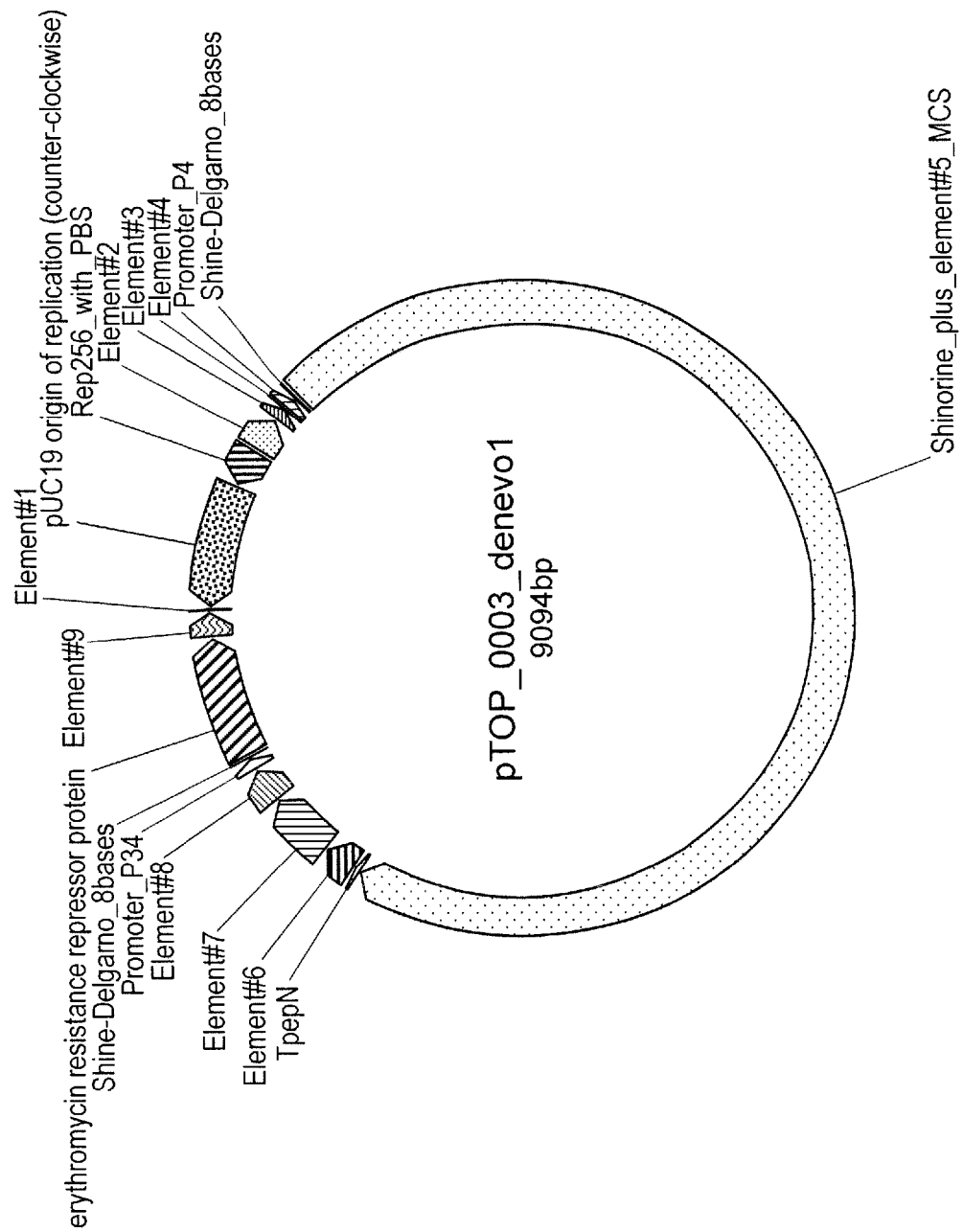
Figure 1C:
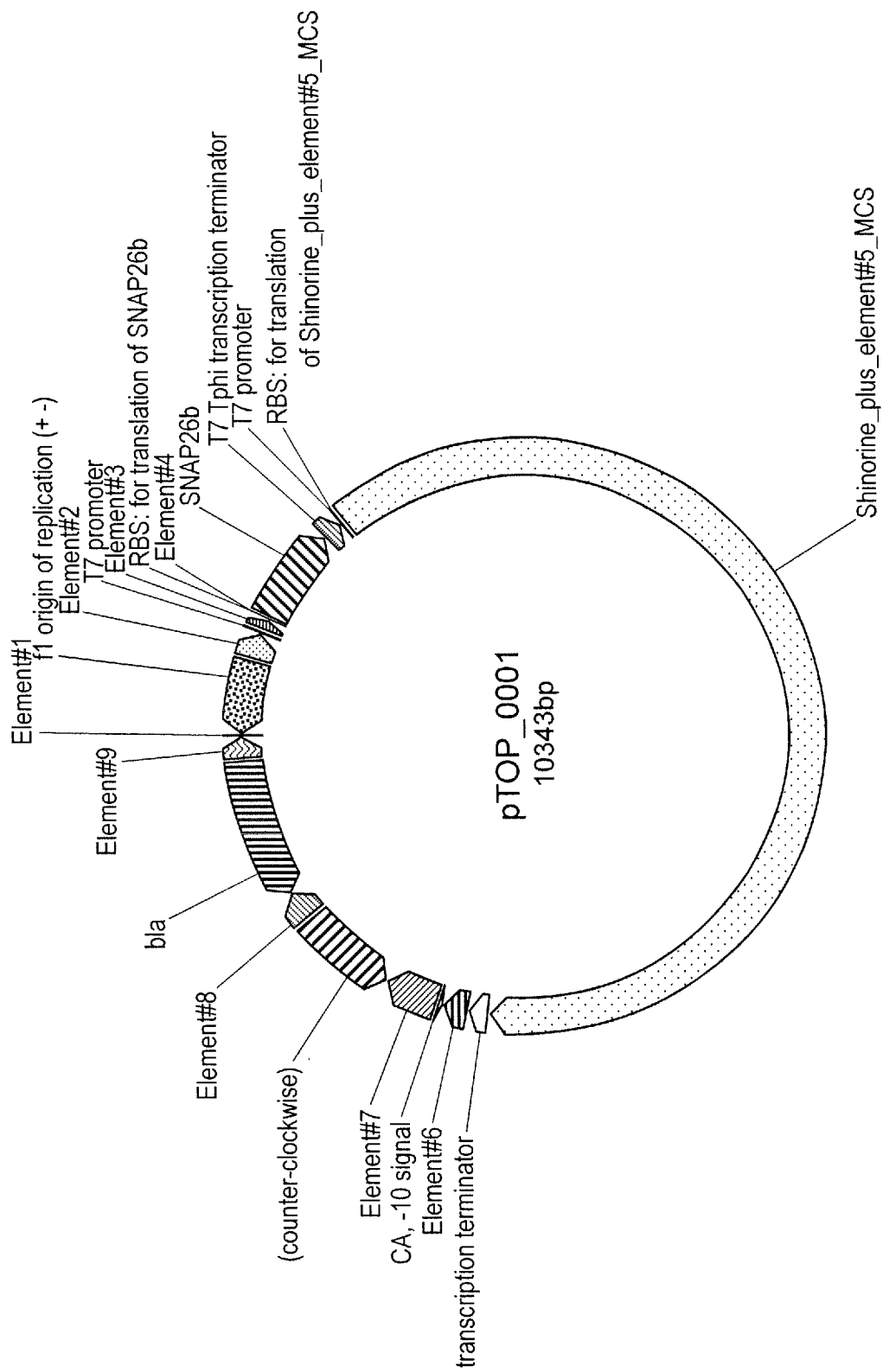

Vectors for transformation of the bacteria can be designed by skilled artisans. An example is set forth in FIG. 1, and as a sequence in SEQ ID NO:15 and with restriction enzyme as in SEQ ID NO:14. In one embodiment, the vector contains a compatible backbone origin of replication to the bacteria strain in use, a compatible promoter for the expression of molecule of interest, and a compatible resistance gene. The plasmid can contain sequences of restriction enzymes.

2. Vector Types

The four major types of vectors are plasmids, viral vectors, cosmids, and artificial chromosomes. Common to all engineered vectors are an origin of replication, a multi-cloning site, and a selectable marker. Any of these are suitable for use herein.

The sequence codes for the molecule of interest can be inserted into a clone, vector, shuttle, plasmid, BAC, or can also be integrated into the bacterial genome.

The copy number of the plasmid can be between 5-500 copy numbers per cell.

Exemplary plasmids and expression vectors include but are not limited to:

p252, p256, p353-2 (Leer et al. 1992), p8014-2, pA1, pACYC, pAJ01, pAl-derived (Vujcic & Topisirovic 1993), pall, pAM-beta-1,2,3,5,8 (simon and chopin 1988), pAR1411, pBG10, pBK, pBM02, pBR322, pBR328, pBS-slpGFP, pC194 (McKenzie et al. 1986, 1987; Horinouchi & Weisblum 1982b), PC194/PUB110, pC30i1, pC30il (Skaugen 1989), pCD034-1, pCD034-2, pCD256, pC12000, pC1305, pC1528, pCIS3, pCL2.1, pCT1138, pD125, pE194, pE194/PLS1, pEGFP-C1, pEH, pF8801, pFG2, pFK-series, pGK-series, pGK12, pGK13, pIA, pIAV1,5,6,7,9, pIL.CatT, pIL252/3, pIL253, pIL7, pISA (low for $e.$ $coli$), pJW563, pKRV3, pLAB1000 (Josson et al. 1990), pLB4 (Bates & Gilbert 1989, pLBS, pLE16, pLEB124, pLEB590, pLEB591, pLEB600, pLEB604, pLEP24Mcop, pLJ1 (Takiguchi et al. 1989), pLKS, pLTK2, pWCFS101 and pMD5057 (Bates & Gilbert, 1989; Skaugen, 1989; Leer et al., 1992; Vujcic & Topisirovic, 1993; Eguchi et al., 2000; Kaneko et al., 2000; Danielsen, 2002; Daming et al., 2003; de las Rivas et al., 2004; van Kranenburg et al., 2005), pLP1/18/30, pLP18, pLP317, pLP317cop, pLP3537, pLP3537xyl, pLP402, pLP825, pLP825 and pLPE323, pLP82H, pLPC37, pLPE23M, pLPE323, pLPE350, pLPI (Bouia et al. 1989), pLS1, pLS1 and pE194 (Lacks et al. 1986; Horinouchi & Weisblum 1982a), plul631, pLUL631 from $L.$ $reuteri$ carrying an erythromycin-resistance gene, pM3, pM4, pMD5057, pMG36e, pND324, pNZ-series, pPSC series, pSH71 (de vos, 1987), pSIP-series, pSK11L, pSL2, PSN2, pSN2 (Khan & Novick 1982), pT181 (Koepsel et al. 1987), (Khan & Novick 1983), pT181, pC194 and pE194 are not functional in $B.$ $subtilis$ (Gruss et al. 1987), pT181, pE194/pLS1, pC194/pUB110 and pSN2 (Khan, 2005), pTL, pTRK family, pTRT family, pTUAT35, pUBII0 and pC194 (McKenzie et al. 1986, 1987; Horinouchi & Weisblum 1982b), pUCL22, pULP8/9, pVS40, pWC1, pWCFS101, pWV02, pWV04, pWV05, RepA, system BetL.

In one embodiment, the lactose phosphotransferase system, optionally linked to the $E.$ $coli$ bacteriophage T7 promoter; the $L.$ $lactis$ nisA promoter system; vectors comprising promoters regulated by environmental conditions, such as for example the P170 promoter that is only active at low pH. Another exemplary vector is a cosmid, a hybrid plasmid (often used as a cloning vector) that contains a Lambda phage cos sequence. (cos sites+plasmid=cosmid). DNA sequences are originally from the lambda phage, and cosmids can be used to build genomic libraries. Another example is a bacterial artificial chromosome (BAC), which is a DNA construct, based on a functional fertility plasmid (or F-plasmid), used for transforming and cloning in bacteria, usually $E.$ $coli$. Suitable vectors can be chosen or constructed, containing appropriate regulatory sequences, including promoter sequences, terminator fragments, polyadenylation sequences, enhancer sequences, marker genes and other sequences as appropriate. Appropriate bacterial expression vectors are known to the person skilled in the art as described in Nouaille S. et al., $Genetics$ $and$ $Molecular$ $Research,$ 2:102-111 (2003), and in Maniatis, Sambrook and Fritsch. 1982. Molecular Cloning: A Laboratory Manual.

3. Expression and Improving Expression Techniques

The term heterologous expression means that a protein, or gene of interest, is experimentally put into a cell that does not normally make (i.e., express) that protein e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all. Also, the nucleic acid is typically recombinantly produced, can have two or more sequences from unrelated genes arranged to make a new functional nucleic acid, e.g., a promoter from one source and a coding region to a molecule of interest, from another source.

The nucleic acid, generated recombinantly or synthetically, with a series of specified nucleic acid elements that permit transcription of a particular nucleic acid in a host cell is called an "expression cassette". The expression cassette can be part of a plasmid, virus, or nucleic acid fragment. Typically, the expression vector includes a nucleic acid to be transcribed operably linked to a promoter.

Moreover, expression cassettes can include a variety of components to regulate expression and localization of the compound of interest of the invention. For example, expression cassettes can include promoter elements, sequences encoding signal sequences, a coding sequence for the compounds of interest, terminators and anchor sequences.

Promoters—Expression of the heterologous compound of interest can be constitutive or inducible. The promoter to be used can be, for example, inducible $lactobacillus$ lac promoter, LdhL, Sip, ernB, orfX, or artificially constitutive (Rud I. et al., $Microbiology,$ 152:1011-92 (2006).

Examples of promoters are listed in the table of the modular construction, and for example can be, but not limited to: $P_{59}$ (van der Vossen et al., $Appl.$ $Environ.$ $Microbiol.$ 58:3142-3149 (1992)), $P_{23}$ (Elliot et al., $Cell$ 36:211-219 (1984)) promoters), $Lactobacillus$ $casei$ L(+)-lactate dehydrogenase promoter (Pouwels et al., 1993, Genetics of lactobacilli: plasmids and gene expression, Antonie van Leeuwenhoek 64:85-107), Promoter of $Bacillus$ amylase (Weickert et al., $J.$ $Bacteriol.$ 171:3656-66 (1989)) or xylose (Kim et al. $Gene$ 181:71-76 (1996)) promoters as well as the $Lactococcus$ $nisin$ promoter (Eichenbaum et al., $Appl.$ $Environ.$ $Microbiol.$ 64:2763-2769 (1998)) can be used to drive inducible expression. Additional promoters can be: p32 promoter which controls expression of $Lactococcus$ $lactis$ fructose-1,6-diphosphate aldolase (Van de Guchte et al., 1990, Appl. Environ. Microbiol. 56:2606-2611), T7 gene 10 promoter (Wells et al, 1993, Mol. Microbiol. 8:1155-1162), alpha amylase promoter sequence of $Lactobacillus$ amylovirus (Pouwels et al., 1993, Genetics of lactobacilli; plasmids and gene expression, Antonie van Leeuwenhoek 64:85-107), and promoters which control expression of: LdhL, Sip, ermB, orfX, p6 (pLA6), pLT71, T7, p11, lacTp, dltp, ccpAp, pip, and inducible $lactobacillus$ as lac promoter, LdhL, Sip, ernB, orfX, as shown by Kim J H, and Mills D A. $Plasmid.$ 58:275-83 (2007).

Several recombinant techniques to improve expression, or cloning and expression of elements are known, including molecular biology methods, nucleic acid and clone construction, mutagenesis, sequencing, introduction of DNA into cells, and analysis of proteins, are described in detail in Current Protocols in Molecular Biology, Ausubel et al. eds., John Wiley & Sons, 1992, and in Molecular Cloning: a Laboratory Manual: 2nd edition, Sambrook et al., 1989, Cold Spring Harbor Laboratory Press Also, it is possible to configure the number of promoters and their length, for better expression (Yagur-Kroll S. et al., *Bioeng Bugs*, 2010 1:151-3 (2010).

The mechanism of replication of the replicon can be of RCR mechanism or by theta-replicating plasmids. The resistance gene can be based on, but not limited to: antibiotics, bacterium marker, heat-shock, or sugar utilization abilities, such as: thymidylate synthase (thyA), lactose phosphotransferase (lacF), phosph-beta-galactosidase (lac G), or alanine recemase (air). Terminator can be added at different positions to provide more efficient expression. A variety of signal and anchor sequences are known to direct expression of polypeptides to the membrane, extracellular space or the cell wall (e.g., by covalent attachment to peptidoglycan).

In addition to comprising the desired gene, the microorganism may also be manipulated to encode other sequence elements which facilitate production of the desired expression of the molecule of interest by the bacterium. Such sequence elements include, but are not limited to, promoter/regulatory sequences which facilitate constitutive or inducible expression of the protein or which facilitate overexpression of the protein in the bacterium. Additional sequence elements may also include those that facilitate secretion of the protein from the bacterium, accumulation of the protein within the bacterium, and/or programmed lysis of the bacterium in order to release the protein from the same. Many of the sequence elements referred to above are known to those skilled in the art (Maniatis, Sambrook and Fritsch. 1982. Molecular Cloning: A Laboratory Manual).

4. Expression of Insert and Validation

Expression of heterologous genes is widely used in biotechnology, especially in industrial food fermentation, contributing to flavor, texture and preservation.

Sequences can be inserted in the vector by de-novo sequencing or by PCR amplification. de-novo synthesized is done by the Capillary Electrophoresis method, or based on Sanger sequencing techniques (Sanger et al. (1974)), when the DNA sequence is copied with high fidelity because at each base on the DNA template, DNA polymerase incorporates only the nucleotide that is complementary to that base. Thymine (T) is complementary to adenine (A) and guanine (G) is complementary to cytosine (C) because they can form hydrogen bonds with each other.

The sequence of the cloned genes and synthetic sequences can be verified after cloning using, e.g., the chain termination method for sequencing double-stranded templates of Wallace et al., *Gene* 16:21-26 (1981).

Appropriate primers and probes for identifying the genes encoding for the compounds of interest of the invention can be derived from the sequences described in the art. For a general overview of PCR, see, Innis et al., *PCR Protocols: A Guide to Methods and Applications*, Academic Press, San Diego (1990).

The concentration of molecule of interest expressed in the host bacteria can be varied from 0.1 mM to 100 mM. This concentration can be controlled by various parameters, such as: the concentration of bacteria, the copy number of the plasmid, the activity of the promoter, and the kinetics of the molecule of interest.

Known sequences of compounds of interest can be identified in commercially available databases, as described in more detail herein.

Exemplary sequences of molecules of interest within the vector are those with genes coding for molecules screening UV. In particular, genes coding for molecules screening UV in the range of 100-500 nm are contemplated. Sequences for molecules of interest within the vector are those with genes coding for molecules reducing oxidative stress, such as genes coding for molecules reducing oxidative stress caused by UV; anti-Oxidants, anti-reactive oxygen species (Anti-ROS). Sequences coding for the genes of interest may be scyA-F, from *Cyanobacteria* sp. Sun screen compounds, such as shinorine, can be obtained from corals (*Stylophora pistallata*), fish (*Scarus schlegeli* and *Chlorurus sordidus*), algea (*Porphyra umbilicalis*), microalgae and, bacteria, as from cyanobacterium *Nostoc* spp., (like as *Nostoc flagelliforme* or *Nostoc* sp. PCC 7524) *Lyngbya* spp., *Anabaena* spp., and *Nodularia* spp. *Nostoc punctiforme* PCC 73102 *Anabaena* sp., *Anabaena variabilis*, *Anabaena cylindrica* PCC 7122, *Cyanothece* sp. PCC 7424, *Cyanothece* sp. PCC 8802, *Rivularia* sp. PCC 7116, *Chroococcidiopsis thermalis* PCC 7203, *Cylindrospermum stagnale* PCC 7417, *Stanieria cyanosphaera* PCC 7437, *Crinalium epipsammum* PCC 9333, *Crinalium epipsammum* PCC 9333, *Anabaena* sp. 90 chromosome chANA01, *Gloeocapsa* sp. PCC 7428, *Chlorogloeopsis fritschii*, *Trichodesmium erythraeum* IMS101, *Microcystis aeruginosa* PCC 7806, *Microcystis aeruginosa* strain *UV*027, *Planktothrix rubescens* NIVA-CYA 98, *Microcystis* sp. NIVA-CYA 172/5, *Nostoc* sp. GSV224, or *Oscillatoria nigro-viridis* PCC 7112.

In one embodiment, the sequence for expression of the compound of interest incorporates into the genome of the bacteria.

The copy number of the plasmid can be between 5-500 copy numbers per cell. The promoters can be constitutive or inducible.

In one embodiment, it is possible to add to the vector DNA and amino acid elements like His-tag to allow purification of the molecule of interest. It is also possible to add an element like usp45, which allows exerting the molecule of interest out of the membrane.

In one embodiment, codon usage can be improved to better express the molecule of interest. Also GC % of the expression vector can be changed and/or reduced.

In one embodiment, the vector includes a limiting factor, or in another embodiment, a limiting factor is incorporated into the bacterial genome via homologous recombination.

5. Transformation

With regard to transformation techniques, appropriate bacterial host strains are selected for, e.g. their transformation ability, ability for heterologous protein expression. The bacterial host will be rendered competent for transformation using standard techniques, such as the rubidium chloride method or electroporation (Maniatis, Sambrook and Fritsch. 1982. Molecular Cloning: A Laboratory Manual).

Particular methods for the transformation of LAB strains are provided in the experimental part hereinafter, but are illustrative of techniques known in the art, and are not intended to be limiting.

Transformation of *Lactococcus lactis* by electroporation can be performed by modifying standard methods as described in, e.g., Luchansky et al. (*J. Dairy Sci.* 74: 3293-3302 (1991). Briefly, freshly inoculated *Lactobacillus* spp. are cultured in MRS broth (e.g., to 0.4-0.8 at $OD_{600}$ at 37° C. and 5% $CO_2$). The bacterial cells are harvested, washed and re-suspended in a cold (e.g., 4° C.) solution of sucrose and $MgCl_2$. Competent cells are then mixed with DNA and placed in a chilled gap cuvette and electroporated. Afterward, cells are allowed to recover in pre-warmed broth (e.g., for about two hours at 37° C.), prior to being plated on selective agar plate containing an antibiotic other selective agent.

Optimization of electroporation in *lactobacillus*: To support cloning and heterologous protein expression in these vaginal *lactobacillus* strains, electroporation methods were developed for application to skin bacteria. Various parameters, including culture media, cell growth stages, DNA concentration, wash or electroporation buffer composition, cuvette gap size, and voltage were evaluated to determine conditions that improved transformation frequencies for the WT *lactobacillus* strains in our collection. *E. coli*-derived plasmids were transformed into *Lactobacillus* strains by electroporation according to Luchansky et al. (*J. Dairy Sci.* 74:3293-302 (1991)) with modifications. Briefly, freshly inoculated *Lactobacillus* strain were cultured in MRS broth to 0.6-0.7 at $OD_{600}$ at 37° C. and 5% $CO_2$. The bacterial cells were harvested, washed and re-suspended in 952 mM sucrose and 3.5 mM $MgCl_2$ at 4° C. Using a pre-chilled 0.2 cm gap cuvette, competent cells were added with 1~2 µg of plasmid DNA) and electroporated immediately at 2.5 kV/cm and 200 ohms. Afterward, cells were allowed to recover in pre-warmed MRS broth for two hours at 37° C., prior to being plated on selective MRS agar plate containing antibiotic, as 20 µg/ml erythromycin.

6. Harvesting

Genetic manipulations allows over production, in different cell lines, of various expressed heterologous desired protein. Over expression, recovering the biological recombinant molecule from the skin bacteria, and harvesting a desired molecule, is the essence of the biotechnology industry, and is known to the person skill in the art (Eugene Russo, Nature, 421 456-457 (2003).

The extracted molecule from the bacteria will be used for dermatological benefits, as for UV protection.

The harvesting procedure may include mechanical, as bead-beating the bacterial cells, or chemically breaking them, by using lysozyme.

Isolation of the expressed molecule can be at various cleaning levels, as from 5%-90%, and can be used by molecular and chemical techniques, e.g. HPLC, HIS-tag, and known to the person skill in the art.

The concentration of the harvested compound can be 1-50% of the biomass before extraction.

Various compounds including bacterial cells and/or particles of the bacterial cells may be dissolved or suspended in the extracts. The final extract may include lipoproteins, lipopeptides, peptidoglycans, lipooligosaccharides, lipoteichoic acids, and teichoic acids. During the lysis process, molecules in the bacterial cells, may become chemically modified. Variose parameters, as pH, starting volume and temperature, may be range to increase yield of harvesting.

D. Exemplary Topical Compositions

The transformed, non-pathogenic populations of bacteria are formulated for topical application to the skin of a subject. Without intending to be limiting, but for purposes of exemplary embodiments, it is contemplated that the formulation may be a gel, ointment, lotion, emulsion, cream, foam, mousse, liquid, spray, suspension, dispersion or aerosol. The formulation includes one or more excipients to provide the desired form and a desired viscosity, flow or other physical or chemical characteristics for effective application, coverage and adhesion to the skin.

Excipients in the formulation are selected based on the type of formulation intended. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecyl sulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars, and starches.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

"Emollients" are an externally applied agent that softens or soothes skin and are generally known in the art and listed in compendia, such as the "Handbook of Pharmaceutical Excipients", $4^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

The basic difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, C12-C15 alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal. In one embodiment, a concentration of a preservative that is effective to prevent fungal growth is selected, without affecting the effectiveness of the composition for its intended purposed upon topical application.

Penetration enhancers are frequently used to promote transdermal delivery of drugs across the skin, in particular across the stratum corneum. Some penetration enhancers cause dermal irritation, dermal toxicity and dermal allergies. However, the more commonly used ones include urea, (carbonyldiamide), imidurea, N,N-diethylformamide, N-methyl-2-pyrrolidine, 1-dodecal-azacycloheptane-2-one, calcium thioglycate, 2-pyyrolidine, N,N-diethyl-m-toluamide, oleic acid and its ester derivatives, such as methyl, ethyl, propyl, isopropyl, butyl, vinyl and glyceryl-monooleate, sorbitan esters, such as sorbitan monolaurate and sorbitan monooleate, other fatty acid esters such as isopropyl laurate, isopropyl myristate, isopropyl palmitate, diisopropyl adipate, propylene glycol monolaurate, propylene glycol monooleatea and non-ionic detergents such as BRIJ® 76 (stearyl poly(10 oxyethylene ether), BRIJ® 78 (stearyl poly(20)oxyethylene ether), BRIJ® 96 (oleyl poly (10)oxyethylene ether), and BRIJ® 721 (stearyl poly (21) oxyethylene ether) (ICI Americas Inc. Corp.).

The microorganisms may be delivered in effective amounts per unit dose, (or per cm$^2$), of at least $10^2$ colony forming units (cfu) to $10^{20}$ cfu per cm$^2$, in particular between $10^5$ cfu to $10^{12}$ cfu per cm$^2$. In accordance with the method as described in Balskus, et al. (Science 2010) UV elements are produced to at least 0.5 mM to 1 mM for $10^6$ cfu. Based thereon, the skilled person in the art can calculate the range of produced element at any other dose of cfu.

The biological compositions may further include one or more beneficial compounds in the formulation, for example, UV protection and chemically (or biologically produced) may include added vitamin A.

The compositions can be prepared by any known or otherwise effective method for formulating or manufacturing the selected product form. In one embodiment, the composition is formulated for application to a skin epidermal surface of a subject, intending to exclude mucosal surfaces, such as nasal, vaginal, rectal, oral surfaces. In one embodiment, topical application excludes the oral cavity, as well as other mucosal surfaces of the body.

The composition can be formulated to comprise the transformed bacterial at a particular concentration to yield a desired concentration of the compound of interest. For example, the composition can comprise an amount of transformed bacterial such that the microorganisms may be delivered in effective amounts per unit dose, (or per $cm^2$), of at least about $10^2$ colony forming units (cfu) to about $10^{20}$ cfu per $cm^2$, in particular between about $10^2$ cfu to about $10^{20}$ cfu per $cm^2$. The composition may be formulated with the transformed bacteria in a proportion of at least about 0.0001% (expressed by dry weight), in particular in a proportion of from about 0.0001% to about 99%, and more particularly in a proportion of from about 0.001% to about 90% by weight, in particular from about 0.01% to about 80% by weight, and especially from about 0.1% to about 70% by weight, relative to the total weight of the composition. In general, a composition intended to be administered topically, may comprise, for living microorganisms, from about 10 to about $10^{15}$ cfu/g, in particular from about $10^5$ to about $10^{15}$ cfu/g, and more particularly from about $10^7$ to about $10^{12}$ cfu/g of microorganisms per gram of carrier, or at equivalent doses calculated for inactive or dead microorganisms or for bacterial fractions or for metabolites produced. In one embodiment, the compositions that have to be administered topically, the concentration of each bacterial strain and/or corresponding fraction and/or metabolite can be adjusted so as to correspond to doses (expressed as bacterial equivalent) ranging from about $5\times10^5$ to about $10^{15}$ cfu/d, and in particular from about $10^7$ to about $10^{12}$ cfu/d. A composition for topical application may generally comprise from about $10^2$ to about $10^{15}$ cfu/g, in particular from about $10^5$ to about $10^{12}$ cfu/g, and more particularly from about $10^6$ to about $10^{12}$ cfu/g of bacteria. When a composition comprises compounds of interest, the contents of compounds of interest in the compositions correspond substantially to the contents capable of being produced by about $10^3$ to about $10^{15}$ cfu, in particular about $10^5$ to about $10^{12}$ cfu, and more particularly about $10^6$ to about $10^{12}$ cfu of compounds of interest per gram of carrier.

In one embodiment, a composition for topical application to the skin for UV protection is contemplated. Photoaging is the alteration in the structure, function and appearance of the skin as a result of prolonged or repeated exposure to ultraviolet radiation from the sun. It accounts for 90% of age associated cosmetic skin problems in both men and women, and moderate to severe photoaging signs were observed in 72% of men and 47% of women under 30 years of age. Ultraviolet radiation is light in the non-visible area of the spectrum that is of shorter wavelength and higher energy; it ranges roughly from 150 nm to 400 nm. Most of the highest energy UV radiation (UVC radiation at wavelengths less than 280 nm) is absorbed by ozone and stratospheric oxygen. UVB radiation comprised of wavelengths from 280-320 nm and UVA radiation made up of wavelengths from 320-400 nm is the two significant causes of damage in organisms. UVB is particularly harmful to organisms because its absorption by DNA creates cyclobutane pyrimidine dimers, which do damage to other DNA, lipids and proteins within the body. It is a common cause of skin cancer. UVA is particularly harmful to organisms because it penetrates deeper into the skin layers. The composition contemplated herein in one embodiment comprises one or more transformed bacteria to express one or more compounds of interest to protect from one or both of UVA and UVB. The composition can be applied to the skin in combination with existing sunscreens of either a chemical (e.g., aminobenzoic acid (PABA), avobenzone, cinoxate, dioxybenzone, ensulizole, homosalate, menthyl anthranilate, meradimate, octocrylene, octyl methoxycinnamate, octisalate, octyl salicylate, octocrylene, oxybenzone, padimate-O, phenylbenzimidazole sulfonic acid, sulisobenzone, and minerals: titanium dioxide, trolamine salicylate, zinc oxide) or physical nature.

The composition of transformed bacteria preferably expresses a compound that protects from UV absorption by the skin, and can be shinorine which a natural mycosporine-like amino acid (MAA) small molecule, absorbing UV radiation, which being synthesized by various organisms as *cyanobacteria*, fungi and algae. In one embodiment, the composition comprising the population of transformed bacteria is a soap or a body wash composition that is applied to the skin.

The microorganisms may be delivered in effective amounts per unit dose, (or per $cm^2$), of at least about $10^2$ colony forming units (cfu) to about $10^{20}$ cfu per $cm^2$, in particular between about $10^2$ cfu to about $10^{20}$ cfu per $cm^2$. In embodiments where the compound of interest is for UV protection, UV elements are produced to at least about 0.1 mM to about 100 mM for $10^2$-$10^{20}$ cfu. Based thereon, the skilled person in the art can calculate the range of produced element at any other dose of cfu. In the particular case of the compositions that have to be administered topically, the concentration of each bacterial strain and/or corresponding fraction and/or metabolite can be adjusted so as to correspond to doses (expressed as bacterial equivalent) ranging from about $5\times10^5$ to about $10^{15}$ cfu/d, and in particular from about $10^7$ to about $10^{12}$ cfu/d.

A composition for topical application may generally comprise from about $10^2$ to about $10^{15}$ cfu/g, in particular from about $10^5$ to about $10^{12}$ cfu/g, and more particularly from about $10^6$ to about $10^{12}$ cfu/g of bacteria.

In one embodiment—the transformed bacteria is applied to an animal's skin, such as pets; including dogs and cats- to prevent UV damage, improve odor, and address veterinarian dermatological needs.

III. Methods of Treatment

In another aspect, methods of treating or preventing disorders or conditions associated with the skin are contemplated. The compositions described above comprising one or more populations of transformed bacteria expressing one or more compounds of interest are applied to the skin in an amount effective to provide a therapeutically effective amount of the compound(s) of interest. As used herein, a therapeutically effective amount is an amount of the topical composition that when administered to a patient or subject, ameliorates, eliminates and/or inhibits the skin disorder or condition in the local region or vicinity of the application of the topical composition.

In one embodiment, a method of protecting the skin from damage due to sun exposure is provided. Methods of treatment for relief of oxidative stress caused by UV, methods of providing an anti-oxidant, an anti-reactive oxygen species (Anti-ROS)), method for providing skin moisturizing, method for promoting anti-aging, and methods for treating psoriasis, eczema, active dermatitis, acne, wound healing (including diabetic wounds or ulcers), intertrigo/diaper rush, burns, insects bites, hives, dandruff (scales), and methods for providing odor control or removal are contemplated.

IV. Packaging of the Composition

After formulation, the composition is packaged in a manner suitable for delivery and use by an end user.

In one embodiment, the composition is placed into an appropriate dispenser and shipped to the end user. Examples of final container may include a pump bottle, squeeze bottle, jar, tube, capsule or vial.

In some embodiments, the packaging is mindful of the nature of the transformed bacteria in the composition. For example, Lactococci grown via respiration survive markedly better after long time storage than fermenting cells (Gaudu et al., Antonie van Leeuwenhoek, 82:263-269 (2002)). This long time survival is probably due to the induction of cytochromes which may protect the cells from oxidative stress. The presence of intracellular glutathione, which is also protecting against oxidative stress, can also result in an improved viability of *Lactococcus lactis* upon storage (Li et al., Appl. Environ. Microbiol, 69(10):5739 (2003)). Another approach to improve the viability of Lactococci upon storage lays in the adaptation of the spray-drying process, and in the use of process aids, such as microcrystalline cellulose, carboxymethylcellulose, hydroxypropylmethylcellu lose acetate succinate, or sodium alginate, which may be used to coat the bacterial particles (EP 1789529 A2). These examples for *Lactococcus* are intended to be illustrative of the types of packaging approaches that a skilled artisan can identify for any of the bacteria described herein.

In another embodiment, the bacteria in the composition are lyophilized or freeze dried, for reconstitution before or after application to the skin. In one embodiment, lyophilization or freeze drying is conducted with one or more excipients, such as glycerol or other sugar alcohols, to improve the shelf life of the transformed bacteria. In one embodiment, the lyophilized composition does not include trehalose (α-D-glucopyranosyl-1,1-α-D-glucopyranosyde).

The packaging for the composition may be in a kit form of one or more containers. For example, a single bottle, tube, container, or capsule may be divided to two equal or unequal parts wherein one part contains the bacteria, in their packing form (freeze dried/inactive, etc.), and the other part contains an activation material, which can be a liquid or a gel. The single bottle or container can be designed so that an end user can dispense with a single force applied to the container all or a portion of the contents in the two container parts, to dispense onto the skin or other surface the transformed bacteria and the activation material. The kit may also be of the form that comprises two or more containers, one container with the population(s) of transformed bacteria and the other with a formulation for admixture with the populations of transformed bacteria. In another example, two or more containers, one container with the population of transformed bacteria, the other container with natural non pathogenic skin bacteria that are not transformed, and a third container with a formulation for admixture with the populations of transformed bacteria. In another example, the two or more containers composing the single bottle had one pump connected to two separate tubes, each draining from a different chamber. The kit may also include one or more complementary products, such as soaps, body washes or moisturizing lotions with certain pH, lotions or creams containing active compounds, bacteria and limiting factors etc. In another embodiment, the complementary product is a limiting factor that will enhance the growth, activity and/or expression of the compound of interest to provide a lasting or continuous expression of the compound. The complementary product may include any compound beneficial to the activity of the original product, and enhance its activity for lasting efficacy.

Another contemplated packaging is one wherein the population of transformed bacteria is maintained as a layer on a bandage or film that is combined with a second layer of bandage/film that will allow activation of the bacteria, and that optionally may also limit reproduction/growth factors.

In another embodiment, the final product could be stored refrigerated, with the bacteria being in their active state.

In another embodiment, the bacteria is stored in a small bead of water soluble cellulose. The beads can be mixed in any solution such as sunscreen/moisturizing/body wash or soap.

V. Examples

The following example is illustrative in nature and is in no way intended to be limiting.

Example 1

*Lactococcus lactis* with the Element Shinorine Using Vector pBTOP1-Shinorine1

A. Bacteria

Bacteria of the *L. lactis* strain are used. A stock solution of the strain is stored in −20° C. in 50% glycerol in GM17/M17 broth with 0.5% sugar. Bacteria are cultured in GM17 medium//M17 broth with 0.5% sugar or in MRS medium. After 16 hours of incubation, bacteria are harvested by centrifugation and 10-fold concentrated in BM9 medium at $2\times10^9$ bacteria/100 µl. On plate or slant, the strain will survive 2-3 weeks.

A stock preparation of the bacteria is prepared by inoculating 5 mL broth with cells from the slant. The cells are grown overnight at 30° C. Then 3 mL fully grown culture is added to 1 ml 60% glycerol and stored at −80° C.

B. Genomic Integration into the Vector pBTOP_shinorine contains the complete operon for shinorine DNA sequence (SEQ ID NO: 1, 2, 3, 4, 5, 6, 7, 8, 9, 10, 11, 12, 13, 14,) and is used production of the compound of interest. Shinorine's operon was integrated in the vector using two exemplary procedures: molecular cloning procedures (Balskus et al., *Science,* 329:1653-1656 (2010)), and de-novo sequencing synthesizing of the plasmid sequences together with the shinorine operon.

B1: Molecular Cloning

The sequence of shinorine, can be obtained from several sources, such as amplification from genomic *Anabaena variabilis* ATCC 29413, de-novo sequencing according to the complete genome of *Anabaena variabilis* or *Nostoc* spp, or amplification from growth culture of *Anabaena variabilis*. In accordance with the method as described in Balskus, et al. (supra), the complete shinorine gene cluster is PCR amplified from genomic DNA of *Anabaena variabilis*, using the forward primer ava3858-start1 (with NdeI restriction site-5'-GAGATCCCATATGAGTATCG TCCAAGCAAAG-3'; SEQ ID NO: 16) and reverse primer ava3855-stop1 (with XhoI restriction site 5'-GTACCTCGAGTCATGAATT-ATTTTCCAGACAATCTTG-3' SEQ ID NO: 17). Primers are designed for ligation into pBTOP1 vector so as to encode untagged gene products. PCR reactions contained 25 µL of master mix, 2 ng of DNA template, and 17 µmoles of each primer in a total volume of 50 µL. Thermocycling is carried out in a PCR machine using the following parameters: denaturation for 1 min at 95° C., followed by 50 cycles of 30 sec at 95° C., 1 min at 50° C., 6 min at 70° C., and a final extension time of 10 min at 70° C.

Amplified fragments are digested with the restriction enzymes NdeI and XhoI for 2.5 hours at 37° C. Digests contain 2 µL water, 6 µL of NEB Buffer 4 (10×), 6 µL of BSA (10×), 40 µL of PCR product, 3 µL of NdeI (20 U/µL), and 3 µL of XhoI (20 U/µL). Restriction digests are purified directly using agarose gel electrophoresis; gel fragments are further purified using the Illustra GFX kit. The digests are ligated into linearized pBTOP1 expression vector using T4 DNA ligase. Ligations are incubated at room temperature for 2 h and contained 3 µL water, 1 µL T4 Ligase Buffer (10×), 1 µL digested vector, 3 µL digested insert DNA, and 2 µL T4 DNA Ligase (400 U/µL). 5 µL of each ligation is used to transform a single tube of the chosen bacterial strain. The identity of the resulting pBTOP1 constructs (shinorine sequence) is confirmed by sequencing of purified plasmid DNA.

B2: Sequencing

The full sequence of shinorine's operon was searched using known databases as the NCBI and identified, and set forth herein as SEQ ID NO:1, 2, 3, 4, 5, 6, 7, 8, 9, 10, 11, 12, 13, 18 which can be used as a template for de-novo sequencing, to be synthesized as an insert to the plasmid, or can be synthesized within the plasmid.

C. Transformation

A vector shinorine harboring shinorine sequence (e.g. SEQ ID NO 1), or any vector constructed for the purpose of blocking UV radiation to be applied on human skin is transformed into *L. lactis* strain, according to the following protocol, including the following steps: Preparation of the bacterial cells, transformation, plasmid extraction, growth of bacteria, Spectrophotometer measurements, and storage of transformed bacteria Preparation of the Cells:

briefly, 1-10 ml *L. lactis* strain from a −80° C. stock grown at 30° C. for 24 hours is inoculated. The culture is diluted by 10×, grown at 30° C., for 24 hours. The 50 mL culture is diluted by 10× and grow until OD600 is 0.2-0.3 (ca. 3 h.), Spin down cells for 20 min 6000×g, at 4° C., Wash cells with 400 µL 0.5M sucrose, 10% glycerol (4° C.) and spin down (6000×g), Resuspend the cells in 200 µL 0.5M sucrose, 10% glycerol, 50 mM EDTA (4° C.), keep the suspension on ice for 15 min and spin down. Wash cells with 100 mL 0.5M sucrose, 10% glycerol (4° C.) and spin down (6000×g). Resuspend the cells in 4 ml 0.5M sucrose, 10% glycerol (4° C.) Use 40 µL per sample (on ice), or keep the cells in small portions in −80° C., let them defreeze on ice before use.

A protocol to transform the cells via electroporation: place 10-100 µL cells in a pre-chilled electroporation cuvette with 1 µL DNA (reconstituted in TE buffer), and keep the cuvette on ice. Use a Biorad Genepulser with following adjustments: 2000 V, 25F, 200Ω. Pulse (normal reading is 4.5-5 msec), add 1 ml growth medium+20 mg $MgCl_2$+2 mM $CaCl_2$. Keep the cuvette for 5 min on ice and incubate 1-1.5 h at 30° C. Plate 10 µL, 100 µl, 900 µL on M17 agar with glucose or lactose and limiting element (depends on plasmid), Incubate 1-2 days at 30° C.; and grow the bacteria in liquid for spectrophotometer analysis, and plasmid extraction.

The cells can also be transformed via heat shock.

Three samples (transformed bacteria (*L. lactis* transformed with molecule of interest inserted into vector (e.g. SEQ ID NO 15), only bacterial cells (not transformed); and bacterial strain with a designed vector without the shinorine sequence inserted are checked in a regular spectrophotometer using UV wavelengths of 270 nm, 310 nm, 330 nm, and 360 nm, every 10 min for an hour up to 10 days, or 200-400 nm every 10 min for an hour up to 10 days.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A composition, comprising a population of non-pathogenic bacteria obtained from a non-pathogenic human skin microbiome genetically transformed to express a mycosporine-like amino acid (MAA) at a level of 0.1 mM to 100 mM for $10^2$-$10^{20}$ cfu of the genetically transformed bacteria, the composition formulated for topical application to a subject.

2. The composition of claim 1, wherein the population of said non-pathogenic bacteria is a population of live bacteria that chronically express the MAA of interest.

3. The composition of claim 1, wherein the population of genetically transformed non-pathogenic bacteria is attenuated bacteria or killed genetically transformed non-pathogenic bacteria that express the MAA of interest prior to or after attenuation or prior to killing.

4. The composition of claim 1, wherein the population of genetically transformed non-pathogenic bacteria is created from a bacteria selected from those in the group consisting of *Lactobacillus casei, Lactobacillus reuteri, Lactobacillus acidophilus, Lactobacillus jensenii, Bifidobacterium lognum, Bifidobacterium reuteri, Bifidobacterium lactis, Bifidobacterium breve, Bifidobacterium animalis, Propionibacterium acidipropionici, Propionibacterium freudenreichii, Propionibacterium thoenii,* and *Propionibacterium jensenii.*

* * * * *

SEQUENCE LISTING

<160> NUMBER OF SEQ ID NOS: 18

<210> SEQ ID NO 1
<211> LENGTH: 6459
<212> TYPE: DNA
<213> ORGANISM: Anabaena variabilis

<400> SEQUENCE: 1

```
atgaattatt ttccagacaa tcttgtaaac gctgtgctaa aacctgtaca tggggttcta      60
gaacaaacga ataatggttt ccagggacat caataatctt aatttcttga gccgccatta     120
cagaaaataa ttctacccaa actaaggtcg ggtcaggagc cataatatgt ttttccctgg     180
ctcgaaatac agtgactttt cctggatatg gttgtcttat ataggaataa gttgctttta     240
aagttcccac caaaacatca agaatacggc gattattttg acgttctaca ccaggcggga     300
atattctagc gctccgtgct ttatcaatga tgtaattaat tttttcttct acagttaaat     360
```

```
tttctatttc ttcaggtgtg actagattat cttgaccaaa cataccgcca aaaactctgg    420
agagaacacc aactaaataa acgtcatcaa tgggttttg tttatccagc agaatcggta     480
cgtaagaatc taatattgct agtaaagata cttcttgtcc ttgtctatgt aactgctgtg    540
ctacttcata agctacgact ccaccaaatg accaccccc gacacgataa ggcccttggg     600
gttgaaattc tctaatagtt ttgacgtaga gactagccat atcttcaact cgcgtcaagg    660
gtgcttcatc tccataaaat ccttgagctt gtaagccata aaatggttgg tcagttccta    720
tatattgtgc gagtttaaaa tagcataaaa catgaccacc agcaggatgt atacaaaaga    780
aaggctgctg cttaccttgt ggttgaattg gaactagggg tgaattatgg atttggttgt    840
ttgcttgaat aaccttggct aaatctgcaa ttactggatt tgttaaaagt gttgctaagg    900
atatctcttt agcaaataac tcttcaattt gagaaattaa atgtagagct ttgagggaat    960
taccaccaat agcgaaaaag ttttctgtca cacctacttt aggtaaatgc agaatattcg   1020
accagatttg tactaatttt tcttcaactt cattccgagg cgctacatag gaattatgtt   1080
cactataatt aaataaatca ggcttaggta atgccttacg gtctacttta ccactgggag   1140
ttaaaggaag atgctccagc atcacaaaag cggctggaat cataaaatca ggtagccttg   1200
cttttaggaa atcacgcaga ttatcaagct gaggtttgat ggagttatag gtaatataag   1260
cgatgatttg ttttcttga gcgttatcat cccgcgctat gactacagct tctctgactt    1320
gtgggtgtga agataaaaca ttttcaatct cgccaatttc aattctataa ccccgaattt   1380
ttacttgata atctgttcta ccaagatatt caatatttcc atcgggtaaa taacgagcta   1440
aatcacctgt tttataaagt cgcttaaact cagaattggg aaagggatta ataataaatt   1500
tttctttggt caattcttct ttattcaaat aaccacgagc aaccctaca ccaccaatat    1560
aaatttcacc agtgacacca atatttactg gttgtaaatc ggcatcaaga atataaattt   1620
gagtattagc aatgggacga ccaataggta cactcttaa attactatct tttctacatt    1680
gccaaaatgt gacatcaatt gctgcttctg tcgggccata gaggttatgt aattcacatt   1740
gcaaatgctg gaaaaatcta ttttgtaaat ctatagataa agcttcaccg ctacaaataa   1800
ctcttttag agagctgcat ttgcttacat ggcgattttg taaaaacact tgcagcattg     1860
agggacaaa atgcaacgta gtgatttgtt cttgagtaat taaatcgatg aggtaagcac     1920
tatctttatg tccgcctggt ttggctatta ccaaacgtgc gccagttaat aaagtccaaa   1980
agaactccca aacggaaaca tcaaaactaa aggggggtttt ttgtaaaatg ctatctgtgg   2040
aatcgatttg ataagcttcc tgcatccaca ataagcgatt acagatacct ttgtgggtgt   2100
tcattgcacc ttttggttta ccagtggaac cagaggtgta aattacataa gcaagattat   2160
ccgtttttat attactttg ggattggtat tagcttgtgt ggaaatttc tcccattccc      2220
tatctacaca gatagtttgt gcttgatggt ggggaatttg attgagtaat ttttcttgag   2280
ttagtagtac cttcacctga gaatcttcta gcatataagc tatgcgttct tgaggatatt   2340
cagggtcaat aggaacataa gcaccccag ctttgaggat tcctaaaaga cagataacca    2400
tttctaagga acgttctaaa caaacgccta ccagggtttc tggctggact cctaatgttt   2460
gtaaataatg tcctagctgg tttgctttat gatttagttc ttgataagtt agttgttgct   2520
tgtcaaaggt gacagcgatc gcctcaggtg ttcgttctac ttgagctaca attagttcat   2580
gtaaactctg ggaaagatca taatctctgt gggtcgcgtt ccactctaca agtaacttac   2640
gaatattaaa atctatagtc tgcatatctt ctaactttgc tcaataataa aaatttctc    2700
acgcagagac gcagagaaaa cacactccgc gtccctctct cttgaaaagt ttcctacgga   2760
```

```
gggaaaccct cctccagaac ttttcgctgc gctaacctca gcgtccctct gcgtttaaaa    2820
actaatctcc ccccaattcc accaacttcc caatattgaa atctatccgc gtccaacctt    2880
taagacgacg caaattattc aataacagta ggggaatttg ccaatgatgt accatcaaaa    2940
acggtaaggg gtcatctggc tgataaatcg catcagtccc gcgccaaata ttccccagcc    3000
atctttgcaa ctgggtgaaa gaacggatac cagttaaacg ccaaacttcg tgataagtcc    3060
aataggtagg cttgcttgtc gttagtggtt gtatggtttc agtcgtcggt gcttgactca    3120
agtacgcttc tgctacctgg gggtggtcgt aaaatgtggt aattgctgaa tgtgtgcggg    3180
ggttacactc gatggcgtaa actgttccgt cttcggcttg gataaagtca aaggaaatct    3240
gtcctgtcag tttcagttcc ttgacaaaat gctgtaccca ttcggtaatt tgcgggttat    3300
ttacattctc ataattaact tggaaggctg aagattcgca acagcaatgc agtctgagtt    3360
ccccattccg aacggtgcta tgggtgcaga attccttacc ggggataaat tcctgcataa    3420
tccacggttt ttcgggagta attggcaaac ttctgacgaa tgctgctgtt tcctctggag    3480
tagcacaggg gagtttggtt aagtccaacc gccgcactga gtcgtaggga atgcttttga    3540
ggatgtattt acgtgtctct ccagaaaaat cgaagttgat gacttgttct ggtgaggtaa    3600
ttttaaagga tttgggtact gataaaccaa gcgatcgcgc tttttgtgtc aacgcaaatt    3660
tatcatccaa catttgggta atatctgcgt caaagtgaaa cacttcgcaa taatgggata    3720
actctggttt ggctaatgag tcgtagtagc tacccactgg actggtgacg ggaatataaa    3780
catcgatgtt ttcttgtttg acgatatcta ccaaagcctg aatgtaagct tggggattgt    3840
cctggggtgc ggggactgtg taaaacttat ccactgcttg ggaaaaacga tgaccagtca    3900
accagtattt atgggtttcc accaagacaa ctctatgtcc agccgcgtgg aatgaccttg    3960
ctagttgtaa agctttggtc atcttaccgc cactgataag aatggtttgg gggtttgctg    4020
ctttgacctt ttgcggtcgg aagactaaca aggatataaa aacaatggtg gcattaatgg    4080
gcaatgctag taataacaaa gccaaagtgc agatattttg gataattgcg gctattttcg    4140
tctgggaagg aagagacggt gtagcaggtg cggaagaaag gggaagggat tgtgccatag    4200
tcgattggac aattaaggtt gtattctgcg gataattgtt aaaccatctc gcaacggcaa    4260
caaaacctgt tctacacggg ggtctatagc tactgtatga ttaaattgcg cgatcgcttc    4320
accattgacg ctacgttcct ctgctggtag ataaacttcc ccttgtaata aggtgttatc    4380
tacacaaata aagccatctg gtgctaacaa actgctacct agcaacttgt gaaaataggc    4440
tacatactct ttttatctg cgtcgataaa taccaagtca aaagactccc cagcttctgc    4500
taacttatca agagttgcta aggctgcatc caattccaca cgaatctttc caccgtgggg    4560
agattgttga aaggctttct gtccaatttc cgccgcgtaa gggtcaactt cacaagccac    4620
aagcagtcca tcctctggta atgcttccgc catcgccagc gccgaataac cggtaaacat    4680
cccaatttct aagactttt tagctttggt catgtgaaca acatctttta aggtttgtcc    4740
ttcgatatga ccagaaagca tctcttgttc tagaggacgg acggttgtac ctccgtggaa    4800
gtgttctccc caggcttcgg tggctgtggt ttttgccaat gcagcgagtt caggagattc    4860
tggagtggtg cattcttcca aataagggtc tatacctgcg gctaaacgcc aagcctgatg    4920
gatgtttgct atcaattccc caggtaaatc tggatgttgc ttaacctctt ggactatggc    4980
ttctaactgc ttggttaaaa ttcccaatgg tgtaacaggt ctagctgttg gttggacaat    5040
cacatttgtc aagtcgcttc gctccaattc aaaattcaaa attcaaaatt caaaattaaa    5100
```

```
gacaattagt gtccgattat ttgcgtagcc ttctcttccc ctacgggacg ctccgcgaac      5160
agaaatgcta ccgcgctcgc gcagtgtatc cgtggagtat tttgcatttt gaattcaaaa      5220
aagtcattat ttaacactcc cgattaattc ttttgataa  acgggataca catccacacc      5280
ttcaccacca cggggataac tggtacaaag ttctttgtgg tcagctaatg cggctgctaa      5340
ttcttctctt gtcaggtcat tgacgaagac acaatcacca atgggttttg gcatagcagc      5400
tcttaacaaa ccatcacgag ttaatgtgat agattcagta ccacgccaca aaatatctat      5460
atccaacatg ggatggtcga gggatagacc aacgcgactc attaatccta aaatacgatc      5520
gcgttctgca attgtaatat atcctctacg ggcggcgatc gttgccgaga aagccatatc      5580
tacattaacg gcgtgtccgt ggaacatggg tagacgaggc gcaagttcca aggtgggact      5640
ccaagtgtga ccgtaagcaa tcaccctatc taggtctaac tcatgcaggt tgggaacttc      5700
caattccaac atcttatgga tagctttgta agtcaaacga tgggctattt ctttaatctc      5760
tggagttgca tctatattgc caaaatgagt acgtagtaat tcttcgccgt acttctccaa      5820
caattcaaaa acttcttgat gcgctactac agcgatttt  accaattccg ccatcccgtt      5880
acgtacttgg tctgtaggga gagtacgcaa caaggagaaa tctaaaaata ctttgcgaga      5940
agcatgataa gcacccaaac ggttttcag  tttgcgatga ttaactgcta ccttaattgc      6000
tacactggca tcaattaatc caatcaatgt agtaggaatg cggatgtaat tgctgctgcg      6060
acgatatgta gaacaagcaa agccgacaac atctgtaatt aaaccgccac ccacgactaa      6120
tactggttct ttgcggacta atttgaaatc tgcaaagaca tctataactc tctcgaaagt      6180
ttgaatagtc ttatctggtt cagtaatggt aataggaaat agcctcagtt ctataccata      6240
atactggaaa tatgcctgaa tttgattacc atacaaccga ctgacgttag catctacaat      6300
cgccaagcat cgtccaaaac cttgatatac atctgctagt gcagaattct ggatttcaaa      6360
aataccatct acatacacca aatcatactc aatcttttcg taaccttcta catgaaaaga      6420
tgtttcctta gcttcaaact ttgcttggac gatactcat                             6459
```

<210> SEQ ID NO 2
<211> LENGTH: 7210
<212> TYPE: DNA
<213> ORGANISM: Nostoc sp.

<400> SEQUENCE: 2

```
cttttaaaca ttctgctaaa acctgtacat gaggttctaa acaaacgaa  taatgatttc       60 ctggcacatc aataatatta atttcctctg ctgccattac agaaaataac tccacccaaa      120
ctaaagtggg atcaggagcc ataatatgtt tctccctagc tctaaaaatt gttacttttc      180
caggatatgg ctgtctttta taggaataag ttgcttttaa agttcccacc aatacatcta      240
aaatgcggcg attattttga cgttccacac caggaggaaa aattttcgct ttctggctt      300 tgtcaatgat ataattaatt ttttcttcta aacttaaatg ctggatttct tctggtgtaa      360
ctaaattatc ttgaccaaac attcccccga agactctaga aagtacaccc acgagataaa      420
catcatcaat ttgttttgt  ttatctaata aaatgggtac gtaagaatca agtatggcta      480
acaaagatac ttcttgtcct tgctttatta gctgctgtgc tacctcataa gcaaccactc      540
ccccaaacga ccaacccct  aattgataag gcccttgggg ttgaaattct ctgatagttt      600
tcacatagag gctggccata tcttcaactt tagttaaagg ttcctctttc ccataaaaac      660
cctgagcttg caaccataa  aacgttgtt  cattgcccat gttatgggct aatttgaagt      720
aacataaaac atgaccaccg gcaggatgta tacaaaagaa aggttgcttc ttaccttgtg      780
```

```
gctgaatggg aactaaagga gaattctgaa tcagattact ggaatcttga ataactgctg    840
ctaaatctgt aattactggg ttctttaata gtgttgctag agggatttct tttccaaaat    900
cttgttcaat tttagagatt aaatgtagtg ctttaagtga atttccacct aacgcgaaaa    960
agttatcttt tactcctatt tgtggtaaat ttaggatgtc tgaccaaatt tttactaatt   1020
gtgcttctac ttgattacga ggagcgacaa aatcattaat ttcaatgaaa tgagaaatat   1080
caggttgtgt taaagcttta cggtctactt ttccactagg agttaaaggt agtgcttcca   1140
gcatgacaaa agcggctgga atcataaaat caggtagctt tgctttcaaa aaatcacgta   1200
ggctgttaag tgttggtttt tctgaatcgt aggtaatgta agcaacaagt tgttttttcta  1260 aattttgatg attacgcgca ataattacag cttctcgcac ttgcgaatgt aagcagagag   1320
tattttcaat ttcgccaatt tcaatccgat aacctcggat ttttacttga tagtctactc   1380
tgccaatata ttcaagattg ccatctggta aataacgagc taaatcacca gttttgtaga   1440
gacgttccga tactaatttt gatttttttaa aaggattggg aataaatttt tcattagtta  1500
attctggacg attccagtaa ccacgtgcta cgccgacacc accaatatac atttcaccga   1560
tgacaccgac atctacaggc tgcaagtgtt cattaaggat gtaaatttgg gtgttagcaa   1620
tgggacgacc aattggtaca gttttttaaat tactgtgctt ttgacactgc caaaaagtga   1680
catcaatagc tgcttctgta gggccgtaca ggttatataa ttcgcagtcc aaacgctcaa   1740
aaaatctatt ttgtaaatct acaggtaaag cttcaccact acaaattact ctttgaagag   1800
aagtacattt ttctatacca cgactagcta aaaacatttg cagcatggag gggacaaaat   1860
gcacagtagt gatttgctct tgaataatca gattaattaa ataattacta tctctatgtc   1920
cacccggttg agcaattact aggcgcgcgc ctgttaataa agtccaaaag aattcccaga   1980
cagagacatc aaagctaaaa ggtgtttttt gtaaaatgct atctgtagaa tttatttgat   2040
aagtttcttg catccacagc aagcgattac atataccttt gtgggtgttc attgcacccct  2100 tgggtttacc agtagaacca gaagtgtaga tgacataagc aagattatct gcttttactt   2160
cactttgggg attagtcttt ggttgtgtag aaattttgtt ccattctgta tctacacaaa   2220
tagtatgtgc ttgatggtgg ggaatttgat ttagtaattt ttcttgggtt agtaataccct  2280 gaatttggga atcttctagc atataagcta tgcgttcttg gggatattct gggtcaatgg   2340
gtacataagc accaccagct tgagaattc ccaataaaca cacaaccatt tctaaggaac    2400
gttctagaca aacaccaact aatgtttctt gttgaactcc tagtgtgtgt aaatgatgtg   2460
ctagttgatt ggctctatta tttaattctt gataggttat tgttgctgt tcaaacttta    2520 cagctatggc gttggggggtg cgttctactt gcgttgtaaa taactcatgt aaaccttgag   2580
aaaggtcgta atctctgtgt gtagcgtcgg gatttatttg tgtggtttgc attttttaaat  2640 cagggaaaaa tgtcggttaa tggctttgtg gaatgggggt gatttactca cccagagatg   2700
caaagacgca aaaaaaccta atctttttctt ctttgcgcct ttgcgccttt gcgtgagata   2760
aaaaaaatcc ttaatctccc ccgaattcga ctaatttacc gatgttgaaa tctatccgcg   2820
tccagccttt gagttgacgg agattattta acaacaacag aggaatttgc cagtgatgta   2880
ccatcaaaaa tggtagggga tcatgtagct gtaaaattgc atctgttccg cgccaaatgt   2940
ttttcagcca tgtcttcaac tgggtgaagg aacgaatacc agtcaagcgc caaatttcgt   3000
gataagtcca ataggttggt ttgctggttg ctaatggttg taaggtttcc gccattggtt   3060
gtttaccaat gtaagcttct gcaacttggg ggtggttgta gaaggtggta atagctgagt   3120
```

```
gtgtgcgggg gttacactcg atcgcgtata cttgtccgtc ttcagtttgg atgaagtcga    3180
aggatatctg tcctgtgagt ttgagttctt tgacaaagtg tctcacccat tccaagattt    3240
gcgggttttc tatgttctca tagttgactt ggaaggctga tgattcgcaa caacagtgta    3300 gtcgaattc tccgtccta actgtgctgt gggtgcagaa ttcttttcct gggatgaatt    3360
cttgcataat ccacggtttt tcgggactga tgggtagttt tctgacgaag gctgctgttt    3420 cctctgggt ggcgcagggg agtttggtta agtccaaacg ccgcactgag tcgtaagcaa    3480
tgcttttgag gatgtatttg cgagtctcac gggaaaagtc gaagttgatg acttgttcgc    3540
cagaggtgat tttaaaggat ttgggtactg ataaaccaag cgatcgcgct ttctctgcca    3600
ttgcaaattt atcatccaac atttgggtga tctctgcatc aaaatgaaac acttcgcaat    3660
ggtgagataa ctctggtttg gctaaggagt cgtaataact cccgacagga ctggtaacgg    3720
gaatgtatac atcaatgttt tcccgtttga ctatatctac taaagctttg atatagtctt    3780 ctggttttt ttgcggtgcg ggagttgtgt aaaatttatc gaccgcttgg gaaaatcgat    3840
gtcccgttaa ccaatattta tgtgtttcca gcaataccac ccgatgtcca tctgcgtgga    3900
atgaccttgc tagttgcaaa gctttggtca tttttccgcc actgatcagg atattttgg    3960 ggttgctggt ttttgtagtt tggggacgga agatagtacc caaaaccaaa gctatgcaaa    4020
caataatggc gttgatgggc aatgctaata gtagcaaagc caaagtcaga atattttga    4080 taattgcggc tattttgtc tctaaaccta gagacggtgt agcaggtgag gagtcaaagg    4140
aaatagattg tgccatagtt tacactcggc ggataatcgt caaaccgtcg cgcaggggaa    4200
gtaaaacctg ttctacacgg atatcaaggg ctacggtacg attgaagtca gcgatcgctt    4260
gaccgttagc actgcgtttt tggggaggta aatatacctc tccttgtagg agtgtgttat    4320
caacacaaat aaagccttgc ggtgctaaca aattagtatc tagcagcatt tgcaagtaag    4380
ctgtgtactc ttttttatcg gcatcaataa ataccaagtc aaaagtttct ccagccgttg    4440
ctaatttctc caaagttgct aaagctgcac ccaattccac acgtatcttt ccaccgtggg    4500
gagattggtt aaaagccttc tgtgcaactt ccgccgcata agggtctact tcacaagcca    4560 ccaataccc atcttctggt aaagcttccg ccatcgctaa ggctgaataa cccgtgaaca    4620
tcccaatttc cagaactctt ttcgctttag tcatgtgaac aaacatcttt aaagtttgtc    4680
cttcgatatg accagaaagc atttcctgtt ctagaggacg cacagttgca ccggctgtaa    4740
aatgctcacc ccaagcctct tttacagtta tcttagcgag tgctgctaaa gcctctgatt    4800
ctggggtagt acattcctct aaataagggt caatacctgc tgctaactcc caagcttggg    4860
taatctcagc taccaaatca gcaggtaaat cttggcgttg tttaacctct cgaacaacag    4920
cttccaactt cttagttaaa attcccaagg gtgtgacagg tctagctgtc ggtatgtcta    4980
tcaaattcgt catgatttaa aggtgtagcc acataaatta gaaaattgct gattgctcaa    5040
agcctgaaag caactgaatt aagactcagc actcatcact ttcctacagc actccctaca    5100
agttccttct gactgctgag aggatacata tctacaccct caccaccacg aggatattga    5160
ctacaaagtt ccttatgttc agctaaagct gcggctgatt cggcttttgt caggtcattg    5220
acgaagaaac attctccaat aggtcttggc atagcagctc tgagtaaacc atctctagtt    5280
agggtgatag actcagtagc acgccataat aactcctcat ccaacagagg atggtcgagg    5340
gctagaccta tacgactcat caatcctaaa atgcgatcgc gctcttgagt agtaatgtag    5400
cctctccgtg ctgcaatagt cgcagacaaa gccatatcaa tattgactgc gtgaccgtgg    5460
aacataggta tatgtggcgc aagttccaag gtcggactcc aagtatgacc gtaagcaatt    5520
```

-continued

```
acccuatccta ggtctaattc gtggaggttg ggtacttcca actccaacat cttttttaatc    5580
gctttgtagg tcacttcatg ggctacatct ttaatttctg gcatagcgtc aatattgcca    5640
aaatgcgtat gcagtaagtc ttccccgtac ttctccaaca actcaaatac ttctttgtga    5700
gcaactacgg cgattttgac taattccgcc ataccgttac gtacttggtc agttggtaga    5760
gtccgtaaaa aggagaaatc taagaaaact tgacgagaag catgatatgc acccaaacgg    5820
tttttcagct tcttgtggtt aactgcgacc ttgatggcaa cactagcatc aattaagcca    5880
attaatgtag taggaatacg gatataatta ctgctgcgac ggtatgcaga gcaagcaaaa    5940
ccgacaacat ctgtaatcaa gccaccacca actactaata ctggttcttt gcgaactaat    6000
ttgaaatctg caaagacatc taccactttc tcaaatgttt gaatggtctt gtttggctca    6060
gtaatagtaa tggggaaaag agtcaagtca atgccgtgat actggaaata ttttgaatt    6120
tgtgtactgt agaactgact cacattagca tctacaacag ccaagcaacg tccaaaattt    6180
ttgtagatat ctgctaattg gtgattttta atctcaaaaa ctccatctac ataaactaag    6240
tcgtactcaa ttttttcgta gccttcaatg tgaaaagctg ctgcttgcgc ttcaaacttt    6300
gcttggacga tgctcatatt ctttgacctt tagtgcagta aatgactgta tgtgttgact    6360
ggaatatttg actcaagcca aaattgaata attctagtcc tagaattaaa ccgattgatt    6420
ggcataccaa ataactctaa tttctcatca agaaatagag gtaatcgctg gcagaatttg    6480
aggtaatcaa aacttgattg taaaaagcag aacgttgatt atatataacg tacagctttt    6540
taaatatagt gaatgacttg tgagtcttgg ttgaactgta agactctgca aatacgagca    6600
aactacatta agtttctact gttttgcagt gatggtacta aatgaagtcc atcatgattg    6660
atctgattgt agacagatat agtatgccag aagttagtag aaatttgctc aaaaatctta    6720
agattttctt cacgatttta aagataacat tatttgcgaa atatttgtac ataattatga    6780
gattttttcta agaaatctca taactataag ctgcaactta gtttatataa gcatcataat    6840
ttttgatctg aactgcaaac caaagaaatt agaggagagt ttgatattaa ttttttatcat    6900
aagtatcagc actactaaaa accatgaatt ttaatcaaca cacagcaaat gtttcccccta    6960
attctgaatc aagaacagga gtatggaagg aaaatttaca gcagattgtt gttaattaga    7020
aatacaaaaa tggagtgcta agataaagc acatctactt ttatgagcgc agcagaaatg    7080
tcattggcat tggctaaaac ttaaggcttc taccaatact tgtaacaaaa cttaactaat    7140
ttgctctcat ttttaagtta gtgacactaa tgaaagtcct aagcaatagc ggacttttttg    7200
cagttgggca                                                           7210
```

<210> SEQ ID NO 3
<211> LENGTH: 888
<212> TYPE: PRT
<213> ORGANISM: Anabaena variabilis

<400> SEQUENCE: 3

Met Gln Thr Ile Asp Phe Asn Ile Arg Lys Leu Leu Val Glu Trp Asn
1               5                   10                  15

Ala Thr His Arg Asp Tyr Asp Leu Ser Gln Ser Leu His Glu Leu Ile
            20                  25                  30

Val Ala Gln Val Glu Arg Thr Pro Glu Ala Ile Ala Val Thr Phe Asp
        35                  40                  45

Lys Gln Gln Leu Thr Tyr Gln Glu Leu Asn His Lys Ala Asn Gln Leu
    50                  55                  60

```
Gly His Tyr Leu Gln Thr Leu Gly Val Gln Pro Glu Thr Leu Val Gly
 65                  70                  75                  80

Val Cys Leu Glu Arg Ser Leu Glu Met Val Ile Cys Leu Leu Gly Ile
                 85                  90                  95

Leu Lys Ala Gly Gly Ala Tyr Val Pro Ile Asp Pro Glu Tyr Pro Gln
            100                 105                 110

Glu Arg Ile Ala Tyr Met Leu Glu Asp Ser Gln Val Lys Val Leu Leu
            115                 120                 125

Thr Gln Glu Lys Leu Leu Asn Gln Ile Pro His His Gln Ala Gln Thr
130                 135                 140

Ile Cys Val Asp Arg Glu Trp Glu Lys Ile Ser Thr Gln Ala Asn Thr
145                 150                 155                 160

Asn Pro Lys Ser Asn Ile Lys Thr Asp Asn Leu Ala Tyr Val Ile Tyr
                165                 170                 175

Thr Ser Gly Ser Thr Gly Lys Pro Lys Gly Ala Met Asn Thr His Lys
                180                 185                 190

Gly Ile Cys Asn Arg Leu Leu Trp Met Gln Glu Ala Tyr Gln Ile Asp
            195                 200                 205

Ser Thr Asp Ser Ile Leu Gln Lys Thr Pro Phe Ser Phe Asp Val Ser
210                 215                 220

Val Trp Glu Phe Phe Trp Thr Leu Leu Thr Gly Ala Arg Leu Val Ile
225                 230                 235                 240

Ala Lys Pro Gly Gly His Lys Asp Ser Ala Tyr Leu Ile Asp Leu Ile
                245                 250                 255

Thr Gln Glu Gln Ile Thr Thr Leu His Phe Val Pro Ser Met Leu Gln
            260                 265                 270

Val Phe Leu Gln Asn Arg His Val Ser Lys Cys Ser Ser Leu Lys Arg
            275                 280                 285

Val Ile Cys Ser Gly Glu Ala Leu Ser Ile Asp Leu Gln Asn Arg Phe
            290                 295                 300

Phe Gln His Leu Gln Cys Glu Leu His Asn Leu Tyr Gly Pro Thr Glu
305                 310                 315                 320

Ala Ala Ile Asp Val Thr Phe Trp Gln Cys Arg Lys Asp Ser Asn Leu
                325                 330                 335

Lys Ser Val Pro Ile Gly Arg Pro Ile Ala Asn Thr Gln Ile Tyr Ile
            340                 345                 350

Leu Asp Ala Asp Leu Gln Pro Val Asn Ile Gly Val Thr Gly Glu Ile
            355                 360                 365

Tyr Ile Gly Gly Val Gly Val Ala Arg Gly Tyr Leu Asn Lys Glu Glu
370                 375                 380

Leu Thr Lys Glu Lys Phe Ile Ile Asn Pro Phe Pro Asn Ser Glu Phe
385                 390                 395                 400

Lys Arg Leu Tyr Lys Thr Gly Asp Leu Ala Arg Tyr Leu Pro Asp Gly
                405                 410                 415

Asn Ile Glu Tyr Leu Gly Arg Thr Asp Tyr Gln Val Lys Ile Arg Gly
            420                 425                 430

Tyr Arg Ile Glu Ile Gly Glu Ile Glu Asn Val Leu Ser Ser His Pro
            435                 440                 445

Gln Val Arg Glu Ala Val Ile Ala Arg Asp Asn Ala Gln Glu
            450                 455                 460

Lys Gln Ile Ile Ala Tyr Ile Thr Tyr Asn Ser Ile Lys Pro Gln Leu
465                 470                 475                 480

Asp Asn Leu Arg Asp Phe Leu Lys Ala Arg Leu Pro Asp Phe Met Ile
```

```
                   485                 490                 495
Pro Ala Ala Phe Val Met Leu Glu His Leu Pro Leu Thr Pro Ser Gly
                500                 505                 510

Lys Val Asp Arg Lys Ala Leu Pro Lys Pro Asp Leu Phe Asn Tyr Ser
            515                 520                 525

Glu His Asn Ser Tyr Val Ala Pro Arg Asn Glu Val Glu Glu Lys Leu
        530                 535                 540

Val Gln Ile Trp Ser Asn Ile Leu His Leu Pro Lys Val Gly Val Thr
545                 550                 555                 560

Glu Asn Phe Phe Ala Ile Gly Gly Asn Ser Leu Lys Ala Leu His Leu
                565                 570                 575

Ile Ser Gln Ile Glu Glu Leu Phe Ala Lys Glu Ile Ser Leu Ala Thr
                580                 585                 590

Leu Leu Thr Asn Pro Val Ile Ala Asp Leu Ala Lys Val Ile Gln Ala
            595                 600                 605

Asn Asn Gln Ile His Asn Ser Pro Leu Val Pro Ile Gln Pro Gln Gly
        610                 615                 620

Lys Gln Gln Pro Phe Phe Cys Ile His Pro Ala Gly Gly His Val Leu
625                 630                 635                 640

Cys Tyr Phe Lys Leu Ala Gln Tyr Ile Gly Thr Asp Gln Pro Phe Tyr
                645                 650                 655

Gly Leu Gln Ala Gln Gly Phe Tyr Gly Asp Glu Ala Pro Leu Thr Arg
            660                 665                 670

Val Glu Asp Met Ala Ser Leu Tyr Val Lys Thr Ile Arg Glu Phe Gln
        675                 680                 685

Pro Gln Gly Pro Tyr Arg Val Gly Gly Trp Ser Phe Gly Gly Val Val
    690                 695                 700

Ala Tyr Glu Val Ala Gln Gln Leu His Arg Gln Gly Gln Glu Val Ser
705                 710                 715                 720

Leu Leu Ala Ile Leu Asp Ser Tyr Val Pro Ile Leu Leu Asp Lys Gln
                725                 730                 735

Lys Pro Ile Asp Asp Val Tyr Leu Val Gly Val Leu Ser Arg Val Phe
            740                 745                 750

Gly Gly Met Phe Gly Gln Asp Asn Leu Val Thr Pro Glu Glu Ile Glu
        755                 760                 765

Asn Leu Thr Val Glu Glu Lys Ile Asn Tyr Ile Ile Asp Lys Ala Arg
    770                 775                 780

Ser Ala Arg Ile Phe Pro Pro Gly Val Glu Arg Gln Asn Asn Arg Arg
785                 790                 795                 800

Ile Leu Asp Val Leu Val Gly Thr Leu Lys Ala Thr Tyr Ser Tyr Ile
                805                 810                 815

Arg Gln Pro Tyr Pro Gly Lys Val Thr Val Phe Arg Ala Arg Glu Lys
            820                 825                 830

His Ile Met Ala Pro Asp Pro Thr Leu Val Trp Val Glu Leu Phe Ser
        835                 840                 845

Val Met Ala Ala Gln Glu Ile Lys Ile Ile Asp Val Pro Gly Asn His
    850                 855                 860

Tyr Ser Phe Val Leu Glu Pro His Val Gln Val Leu Ala Gln Arg Leu
865                 870                 875                 880

Gln Asp Cys Leu Glu Asn Asn Ser
                885

<210> SEQ ID NO 4
```

<211> LENGTH: 458
<212> TYPE: PRT
<213> ORGANISM: Anabaena variabilis

<400> SEQUENCE: 4

Met Ala Gln Ser Leu Pro Leu Ser Ser Ala Pro Ala Thr Pro Ser Leu
1               5                   10                  15

Pro Ser Gln Thr Lys Ile Ala Ala Ile Ile Gln Asn Ile Cys Thr Leu
            20                  25                  30

Ala Leu Leu Leu Leu Ala Leu Pro Ile Asn Ala Thr Ile Val Phe Ile
        35                  40                  45

Ser Leu Leu Val Phe Arg Pro Gln Lys Val Lys Ala Ala Asn Pro Gln
50                  55                  60

Thr Ile Leu Ile Ser Gly Gly Lys Met Thr Lys Ala Leu Gln Leu Ala
65                  70                  75                  80

Arg Ser Phe His Ala Ala Gly His Arg Val Leu Val Glu Thr His His
                85                  90                  95

Lys Tyr Trp Leu Thr Gly His Arg Phe Ser Gln Ala Val Asp Lys Phe
            100                 105                 110

Tyr Thr Val Pro Ala Pro Gln Asp Asn Pro Gln Ala Tyr Ile Gln Ala
        115                 120                 125

Leu Val Asp Ile Val Lys Gln Glu Asn Ile Asp Val Tyr Ile Pro Val
130                 135                 140

Thr Ser Pro Val Gly Ser Tyr Tyr Asp Ser Leu Ala Lys Pro Glu Leu
145                 150                 155                 160

Ser His Tyr Cys Glu Val Phe His Phe Asp Ala Asp Ile Thr Gln Met
                165                 170                 175

Leu Asp Asp Lys Phe Ala Leu Thr Gln Lys Ala Arg Ser Leu Gly Leu
            180                 185                 190

Ser Val Pro Lys Ser Phe Lys Ile Thr Ser Pro Glu Gln Val Ile Asn
        195                 200                 205

Phe Asp Phe Ser Gly Glu Thr Arg Lys Tyr Ile Leu Lys Ser Ile Pro
210                 215                 220

Tyr Asp Ser Val Arg Arg Leu Asp Leu Thr Lys Leu Pro Cys Ala Thr
225                 230                 235                 240

Pro Glu Glu Thr Ala Ala Phe Val Arg Ser Leu Pro Ile Thr Pro Glu
                245                 250                 255

Lys Pro Trp Ile Met Gln Glu Phe Ile Pro Gly Lys Glu Phe Cys Thr
            260                 265                 270

His Ser Thr Val Arg Asn Gly Glu Leu Arg Leu His Cys Cys Cys Glu
        275                 280                 285

Ser Ser Ala Phe Gln Val Asn Tyr Glu Asn Val Asn Asn Pro Gln Ile
290                 295                 300

Thr Glu Trp Val Gln His Phe Val Lys Glu Leu Lys Leu Thr Gly Gln
305                 310                 315                 320

Ile Ser Phe Asp Phe Ile Gln Ala Glu Asp Gly Thr Val Tyr Ala Ile
                325                 330                 335

Glu Cys Asn Pro Arg Thr His Ser Ala Ile Thr Thr Phe Tyr Asp His
            340                 345                 350

Pro Gln Val Ala Glu Ala Tyr Leu Ser Gln Ala Pro Thr Thr Glu Thr
        355                 360                 365

Ile Gln Pro Leu Thr Thr Ser Lys Pro Thr Tyr Trp Thr Tyr His Glu
370                 375                 380

Val Trp Arg Leu Thr Gly Ile Arg Ser Phe Thr Gln Leu Gln Arg Trp

-continued

```
            385                 390                 395                 400
Leu Gly Asn Ile Trp Arg Gly Thr Asp Ala Ile Tyr Gln Pro Asp Asp
                    405                 410                 415

Pro Leu Pro Phe Leu Met Val His His Trp Gln Ile Pro Leu Leu Leu
                420                 425                 430

Leu Asn Asn Leu Arg Arg Leu Lys Gly Trp Thr Arg Ile Asp Phe Asn
            435                 440                 445

Ile Gly Lys Leu Val Glu Leu Gly Gly Asp
        450                 455

<210> SEQ ID NO 5
<211> LENGTH: 279
<212> TYPE: PRT
<213> ORGANISM: Anabaena variabilis

<400> SEQUENCE: 5

Met Thr Asn Val Ile Val Gln Pro Thr Ala Arg Pro Val Thr Pro Leu
1               5                   10                  15

Gly Ile Leu Thr Lys Gln Leu Glu Ala Ile Val Gln Glu Val Lys Gln
            20                  25                  30

His Pro Asp Leu Pro Gly Glu Leu Ile Ala Asn Ile His Gln Ala Trp
        35                  40                  45

Arg Leu Ala Ala Gly Ile Asp Pro Tyr Leu Glu Glu Cys Thr Thr Pro
    50                  55                  60

Glu Ser Pro Glu Leu Ala Ala Leu Ala Lys Thr Thr Ala Thr Glu Ala
65                  70                  75                  80

Trp Gly Glu His Phe His Gly Thr Thr Val Arg Pro Leu Glu Gln
                85                  90                  95

Glu Met Leu Ser Gly His Ile Glu Gly Gln Thr Leu Lys Met Phe Val
            100                 105                 110

His Met Thr Lys Ala Lys Lys Val Leu Glu Ile Gly Met Phe Thr Gly
        115                 120                 125

Tyr Ser Ala Leu Ala Met Ala Glu Ala Leu Pro Glu Asp Gly Leu Leu
    130                 135                 140

Val Ala Cys Glu Val Asp Pro Tyr Ala Ala Glu Ile Gly Gln Lys Ala
145                 150                 155                 160

Phe Gln Gln Ser Pro His Gly Gly Lys Ile Arg Val Glu Leu Asp Ala
                165                 170                 175

Ala Leu Ala Thr Leu Asp Lys Leu Ala Glu Ala Gly Glu Ser Phe Asp
            180                 185                 190

Leu Val Phe Ile Asp Ala Asp Lys Lys Glu Tyr Val Ala Tyr Phe His
        195                 200                 205

Lys Leu Leu Gly Ser Ser Leu Leu Ala Pro Asp Gly Phe Ile Cys Val
    210                 215                 220

Asp Asn Thr Leu Leu Gln Gly Glu Val Tyr Leu Pro Ala Glu Glu Arg
225                 230                 235                 240

Ser Val Asn Gly Glu Ala Ile Ala Gln Phe Asn His Thr Val Ala Ile
                245                 250                 255

Asp Pro Arg Val Glu Gln Val Leu Leu Pro Leu Arg Asp Gly Leu Thr
            260                 265                 270

Ile Ile Arg Arg Ile Gln Pro
        275

<210> SEQ ID NO 6
<211> LENGTH: 410
```

<212> TYPE: PRT
<213> ORGANISM: Anabaena variabilis

<400> SEQUENCE: 6

```
Met Ser Ile Val Gln Ala Lys Phe Glu Ala Lys Glu Thr Ser Phe His
1               5                   10                  15

Val Glu Gly Tyr Glu Lys Ile Glu Tyr Asp Leu Val Tyr Val Asp Gly
            20                  25                  30

Ile Phe Glu Ile Gln Asn Ser Ala Leu Ala Asp Val Tyr Gln Gly Phe
        35                  40                  45

Gly Arg Cys Leu Ala Ile Val Asp Ala Asn Val Ser Arg Leu Tyr Gly
50                  55                  60

Asn Gln Ile Gln Ala Tyr Phe Gln Tyr Tyr Gly Ile Glu Leu Arg Leu
65                  70                  75                  80

Phe Pro Ile Thr Ile Thr Glu Pro Asp Lys Thr Ile Gln Thr Phe Glu
                85                  90                  95

Arg Val Ile Asp Val Phe Ala Asp Phe Lys Leu Val Arg Lys Glu Pro
            100                 105                 110

Val Leu Val Val Gly Gly Gly Leu Ile Thr Asp Val Val Gly Phe Ala
        115                 120                 125

Cys Ser Thr Tyr Arg Arg Ser Ser Asn Tyr Ile Arg Ile Pro Thr Thr
130                 135                 140

Leu Ile Gly Leu Ile Asp Ala Ser Val Ala Ile Lys Val Ala Val Asn
145                 150                 155                 160

His Arg Lys Leu Lys Asn Arg Leu Gly Ala Tyr His Ala Ser Arg Lys
                165                 170                 175

Val Phe Leu Asp Phe Ser Leu Leu Arg Thr Leu Pro Thr Asp Gln Val
            180                 185                 190

Arg Asn Gly Met Ala Glu Leu Val Lys Ile Ala Val Val Ala His Gln
        195                 200                 205

Glu Val Phe Glu Leu Leu Glu Lys Tyr Gly Glu Glu Leu Leu Arg Thr
210                 215                 220

His Phe Gly Asn Ile Asp Ala Thr Pro Glu Ile Lys Glu Ile Ala His
225                 230                 235                 240

Arg Leu Thr Tyr Lys Ala Ile His Lys Met Leu Glu Leu Glu Val Pro
                245                 250                 255

Asn Leu His Glu Leu Asp Leu Asp Arg Val Ile Ala Tyr Gly His Thr
            260                 265                 270

Trp Ser Pro Thr Leu Glu Leu Ala Pro Arg Leu Pro Met Phe His Gly
        275                 280                 285

His Ala Val Asn Val Asp Met Ala Phe Ser Ala Thr Ile Ala Ala Arg
290                 295                 300

Arg Gly Tyr Ile Thr Ile Ala Glu Arg Asp Arg Ile Leu Gly Leu Met
305                 310                 315                 320

Ser Arg Val Gly Leu Ser Leu Asp His Pro Met Leu Asp Ile Asp Ile
                325                 330                 335

Leu Trp Arg Gly Thr Glu Ser Ile Thr Leu Thr Arg Asp Gly Leu Leu
            340                 345                 350

Arg Ala Ala Met Pro Lys Pro Ile Gly Asp Cys Val Phe Val Asn Asp
        355                 360                 365

Leu Thr Arg Glu Glu Leu Ala Ala Ala Leu Ala Asp His Lys Glu Leu
370                 375                 380

Cys Thr Ser Tyr Pro Arg Gly Gly Glu Gly Val Asp Val Tyr Pro Val
385                 390                 395                 400
```

Tyr Gln Lys Glu Leu Ile Gly Ser Val Lys
            405                 410

<210> SEQ ID NO 7
<211> LENGTH: 1233
<212> TYPE: DNA
<213> ORGANISM: Anabaena variabilis

<400> SEQUENCE: 7

| | | |
|---|---|---|
| atgagtatcg tccaagcaaa gtttgaagct aaggaaacat cttttcatgt agaaggttac | 60 |
| gaaaagattg agtatgattt ggtgtatgta gatggtattt ttgaaatcca gaattctgca | 120 |
| ctagcagatg tatatcaagg ttttggacga tgcttggcga ttgtagatgc taacgtcagt | 180 |
| cggttgtatg gtaatcaaat tcaggcatat ttccagtatt atggtataga actgaggcta | 240 |
| tttcctatta ccattactga accagataag actattcaaa ctttcgagag agttatagat | 300 |
| gtctttgcag atttcaaatt agtccgcaaa gaaccagtat tagtcgtggg tggcggttta | 360 |
| attacagatg ttgtcggctt tgcttgttct acatatcgtc gcagcagcaa ttacatccgc | 420 |
| attcctacta cattgattgg attaattgat gccagtgtag caattaaggt agcagttaat | 480 |
| catcgcaaac tgaaaaaccg tttgggtgct tatcatgctt ctcgcaaagt attttttagat | 540 |
| ttctccttgt tgcgtactct ccctacagac caagtacgta acgggatggc ggaattggta | 600 |
| aaaatcgctg tagtagcgca tcaagaagtt tttgaattgt tggagaagta cggcgaagaa | 660 |
| ttactacgta ctcattttgg caatatagat gcaactccag agattaaaga aatagcccat | 720 |
| cgttttgactt acaaagctat ccataagatg ttggaattgg aagttcccaa cctgcatgag | 780 |
| ttagacctag atagggtgat tgcttacggt cacacttgga gtcccacctt ggaacttgcg | 840 |
| cctcgtctac ccatgttcca cggacacgcc gttaatgtag atatggcttt ctcggcaacg | 900 |
| atcgccgccc gtagaggata tattacaatt gcagaacgcg atcgtatttt aggattaatg | 960 |
| agtcgcgttg gtctatccct cgaccatccc atgttggata tagatatttt gtggcgtggt | 1020 |
| actgaatcta tcacattaac tcgtgatggt ttgttaagag ctgctatgcc aaaacccatt | 1080 |
| ggtgattgtg tcttcgtcaa tgacctgaca agagaagaat tagcagccgc attagctgac | 1140 |
| cacaaagaac tttgtaccag ttatccccgt ggtggtgaag tgtggatgt gtatcccgtt | 1200 |
| tatcaaaaag aattaatcgg gagtgttaaa taa | 1233 |

<210> SEQ ID NO 8
<211> LENGTH: 174
<212> TYPE: DNA
<213> ORGANISM: Anabaena variabili

<400> SEQUENCE: 8

| | | |
|---|---|---|
| tgacttttt gaattcaaaa tgcaaaatac tccacggata cactgcgcga gcgcggtagc | 60 |
| atttctgttc gcggagcgtc ccgtagggaa agagaaggct acgcaaataa tcggacacta | 120 |
| attgtcttta attttgaatt ttgaattttg aattttgaat tggagcgaag cgac | 174 |

<210> SEQ ID NO 9
<211> LENGTH: 840
<212> TYPE: DNA
<213> ORGANISM: Anabaena variabilis

<400> SEQUENCE: 9

| | | |
|---|---|---|
| ttgacaaatg tgattgtcca accaacagct agacctgtta caccattggg aattttaacc | 60 |
| aagcagttag aagccatagt ccaagaggtt aagcaacatc cagatttacc tggggaattg | 120 |

| | |
|---|---|
| atagcaaaca tccatcaggc ttggcgttta gccgcaggta tagacccetta tttggaagaa | 180 |
| tgcaccactc cagaatctcc tgaactcgct gcattggcaa aaccacagc caccgaagcc | 240 |
| tggggagaac acttccacgg aggtacaacc gtccgtcctc tagaacaaga gatgctttct | 300 |
| ggtcatatcg aaggacaaac cttaaagatg tttgttcaca tgaccaaagc taaaaaagtc | 360 |
| ttagaaattg ggatgtttac cggttattcg gcgctggcga tggcggaagc attaccagag | 420 |
| gatggactgc ttgtggcttg tgaagttgac ccttacgcgg cggaaattgg acagaaagcc | 480 |
| tttcaacaat ctccccacgg tggaaagatt cgtgtggaat tggatgcagc cttagcaact | 540 |
| cttgataagt tagcagaagc tggggagtct tttgacttgg tatttatcga cgcagataaa | 600 |
| aaagagtatg tagcctattt tcacaagttg ctaggtagca gtttgttagc accagatggc | 660 |
| tttatttgtg tagataacac cttattacaa ggggaagttt atctaccagc agaggaacgt | 720 |
| agcgtcaatg gtgaagcgat cgcgcaattt aatcatacag tagctataga cccccgtgta | 780 |
| gaacaggttt tgttgccgtt gcgagatggt ttaacaatta ccgcagaat acaaccttaa | 840 |

<210> SEQ ID NO 10
<211> LENGTH: 14
<212> TYPE: DNA
<213> ORGANISM: Anabaena variabili

<400> SEQUENCE: 10

| | |
|---|---|
| ttgtccaatc gact | 14 |

<210> SEQ ID NO 11
<211> LENGTH: 1377
<212> TYPE: DNA
<213> ORGANISM: Anabaena variabilis

<400> SEQUENCE: 11

| | |
|---|---|
| atggcacaat cccttcccct ttcttccgca cctgctacac cgtctcttcc ttcccagacg | 60 |
| aaaatagccg caattatcca aaatatctgc actttggctt tgttattact agcattgccc | 120 |
| attaatgcca ccattgtttt tatatccttg ttagtcttcc gaccgcaaaa ggtcaaagca | 180 |
| gcaaaccccc aaaccattct tatcagtggc ggtaagatga ccaaagcttt acaactagca | 240 |
| aggtcattcc acgcggctgg acatagagtt gtcttggtgg aaacccataa atactggttg | 300 |
| actggtcatc gttttttccca agcagtggat aagtttttaca cagtccccgc accccaggac | 360 |
| aatccccaag cttacattca ggctttggta gatatcgtca acaagaaaa catcgatgtt | 420 |
| tatattcccg tcaccagtcc agtgggtagc tactacgact cattagccaa accagagtta | 480 |
| tcccattatt gcgaagtgtt tcactttgac gcagatatta cccaaatgtt ggatgataaa | 540 |
| tttgcgttga cacaaaaagc gcgatcgctt ggtttatcag taccaaaatc ctttaaaatt | 600 |
| acctcaccag aacaagtcat caacttcgat ttttctggag agacacgtaa atacatcctc | 660 |
| aaaagcattc cctacgactc agtgcggcgg ttggacttaa ccaaactccc ctgtgctact | 720 |
| ccagaggaaa cagcagcatt cgtcagaagt ttgccaatta ctcccgaaaa accgtggatt | 780 |
| atgcaggaat ttatccccgg taaggaattc tgcaccccata gcaccgttcg gaatggggaa | 840 |
| ctcagactgc attgctgttg cgaatcttca gccttccaag ttaattatga gaatgtaaat | 900 |
| aacccgcaaa ttaccgaatg ggtacagcat tttgtcaagg aactgaaact gacaggacag | 960 |
| atttcctttg actttatcca agccgaagac ggaacagttt acgccatcga gtgtaacccc | 1020 |
| cgcacacatt cagcaattac cacattttac gaccaccccc aggtagcaga agcgtacttg | 1080 |

```
agtcaagcac cgacgactga aaccatacaa ccactaacga caagcaagcc tacctattgg    1140
acttatcacg aagtttggcg tttaactggt atccgttctt tcacccagtt gcaaagatgg    1200
ctggggaata tttggcgcgg gactgatgcg atttatcagc cagatgaccc cttaccgttt    1260
ttgatggtac atcattggca aattccccta ctgttattga ataatttgcg tcgtcttaaa    1320
ggttggacgc ggatagattt caatattggg aagttggtgg aattgggggg agattag      1377

<210> SEQ ID NO 12
<211> LENGTH: 156
<212> TYPE: DNA
<213> ORGANISM: Anabaena variabilis

<400> SEQUENCE: 12
tttttaaacg cagagggacg ctgaggttag cgcagcgaaa agttctggag gagggtttcc     60
ctccgtagga aacttttcaa gagagaggga cgcggagtgt gttttctctg cgtctctgcg    120
tgagaaattt tttattattg agcaaagtta gaagat                              156

<210> SEQ ID NO 13
<211> LENGTH: 2667
<212> TYPE: DNA
<213> ORGANISM: Anabaena variabilis

<400> SEQUENCE: 13
atgcagacta tagattttaa tattcgtaag ttacttgtag agtggaacgc gacccacaga     60
gattatgatc tttcccagag tttacatgaa ctaattgtag ctcaagtaga acgaacacct    120
gaggcgatcg ctgtcacctt tgacaagcaa caactaactt atcaagaact aaatcataaa    180
gcaaaccagc taggacatta tttacaaaca ttaggagtcc agccagaaac cctggtaggc    240
gtttgtttag aacgttcctt agaaatggtt atctgtcttt taggaatcct caaagctggg    300
ggtgcttatg ttcctattga ccctgaatat cctcaagaac gcatagctta tgctagaa      360 gattctcagg tgaaggtact actaactcaa gaaaaattac tcaatcaaat tccccaccat    420
caagcacaaa ctatctgtgt agatagggaa tgggagaaaa tttccacaca agctaatacc    480
aatcccaaaa gtaatataaa aacggataat cttgcttatg taatttacac ctctggttcc    540
actggtaaac caaaaggtgc aatgaacacc cacaaaggta tctgtaatcg cttattgtgg    600
atgcaggaag cttatcaaat cgattccaca gatagcattt tacaaaaaac cccctttagt    660
tttgatgttt ccgtttggga gttcttttgg acttattaa ctggcgcacg tttggtaata    720
gccaaaccag gcggacataa agatagtgct tacctcatcg atttaattac tcaagaacaa    780
atcactacgt tgcattttgt cccctcaatg ctgcaagtgt tttacaaaa tcgccatgta    840 agcaaatgca gctctctaaa aagagttatt tgtagcggtg aagctttatc tatagattta    900
caaaatagat ttttccagca tttgcaatgt gaattacata acctctatgg cccgacagaa    960
gcagcaattg atgtcacatt ttggcaatgt agaaagata gtaatttaaa gagtgtacct    1020
attggtcgtc ccattgctaa tactcaaatt tatattcttg atgccgattt acaaccagta    1080
aatattggtg tcactggtga aatttatatt ggtggtgtag gggttgctcg tggttatttg    1140
aataaagaag aattgaccaa agaaaaattt attattaatc cctttcccaa ttctgagttt    1200
aagcgacttt ataaaacagg tgatttagct cgttatttac ccgatggaaa tattgaatat    1260
cttggtagaa cagattatca agtaaaaatt cggggttata gaattgaaat tggcgagatt    1320
gaaaatgttt tatcttcaca cccacaagtc agagaagctg tagtcatagc gcgggatgat    1380
aacgctcaag aaaaacaaat catcgcttat attacctata actccatcaa acctcagctt    1440
```

```
gataatctgc gtgatttcct aaaagcaagg ctacctgatt ttatgattcc agccgctttt      1500
gtgatgctgg agcatcttcc tttaactccc agtggtaaag tagaccgtaa ggcattacct      1560
aagcctgatt tatttaatta tagtgaacat aattcctatg tagcgcctcg gaatgaagtt      1620
gaagaaaaat tagtacaaat ctggtcgaat attctgcatt tacctaaagt aggtgtgaca      1680
gaaaactttt tcgctattgg tggtaattcc ctcaaagctc tacatttaat ttctcaaatt      1740
gaagagttat ttgctaaaga gatatcctta gcaacacttt taacaaatcc agtaattgca      1800
gatttagcca aggttattca agcaaacaac caaatccata attcaccect agttccaatt      1860 caaccacaag gtaagcagca gccttttcttt tgtatacatc ctgctggtgg tcatgtttta      1920
tgctatttta aactcgcaca atatatagga actgaccaac cattttatgg cttacaagct      1980
caaggatttt atggagatga agcacccttg acgcgagttg aagatatggc tagtctctac      2040
gtcaaaacta ttagagaatt caaccccaa gggccttatc gtgtcggggg gtggtcattt      2100
ggtggagtcg tagcttatga agtagcacag cagttacata gacaaggaca agaagtatct      2160
ttactagcaa tattagattc ttacgtaccg attctgctgg ataaacaaaa acccattgat      2220
gacgtttatt tagttggtgt tctctccaga gttttttggcg gtatgtttgg tcaagataat      2280
ctagtcacac ctgaagaaat agaaaattta actgtagaag aaaaaattaa ttacatcatt      2340
gataaagcac ggagcgctag aatattcccg cctggtgtag aacgtcaaaa taatcgccgt      2400
attcttgatg ttttggtggg aactttaaaa gcaacttatt cctatataag acaaccatat      2460
ccaggaaaag tcactgtatt tcgagccagg gaaaaacata ttatggctcc tgacccgacc      2520
ttagtttggg tagaattatt ttctgtaatg gcggctcaag aaattaagat tattgatgtc      2580
cctggaaacc attattcgtt tgttctagaa ccccatgtac aggttttagc acagcgttta      2640
caagattgtc tggaaaataa ttcataa                                          2667

<210> SEQ ID NO 14
<211> LENGTH: 6469
<212> TYPE: DNA
<213> ORGANISM: Artificial Sequence
<220> FEATURE:
<223> OTHER INFORMATION: synthetic sequence

<400> SEQUENCE: 14
tcgagatgaa ttattttcca gacaatcttg taaacgctgt gctaaaacct gtacatgggg        60
ttctagaaca aacgaataat ggtttccagg gacatcaata atcttaattt cttgagccgc       120
cattacagaa aataattcta cccaaactaa ggtcgggtca ggagccataa tatgtttttc       180
cctggctcga aatacagtga cttttcctgg atatggttgt cttatatagg aataagttgc       240
ttttaaagtt cccaccaaaa catcaagaat acggcgatta ttttgacgtt ctacaccagg       300
cgggaatatt ctagcgctcc gtgctttatc aatgatgtaa ttaattttttt cttctacagt      360 taaattttct atttcttcag gtgtgactag attatcttga ccaaacatac cgccaaaaac       420
tctggagaga acaccaacta aataaacgtc atcaatgggt ttttgtttat ccagcagaat       480
cggtacgtaa gaatctaata ttgctagtaa agatacttct tgtccttgtc tatgtaactg       540
ctgtgctact tcataagcta cgactccacc aaatgaccac ccccgacac gataaggccc       600 ttggggttga attctctaa tagttttgac gtagagacta gccatatctt caactcgcgt       660
caagggtgct tcatctccat aaaatccttg agcttgtaag ccataaaatg gttggtcagt       720
tcctatatat tgtgcgagtt taaatagca taaaacatga ccaccagcag gatgtataca       780
```

```
aaagaaaggc tgctgcttac cttgtggttg aattggaact aggggtgaat tatggatttg    840
gttgtttgct tgaataacct tggctaaatc tgcaattact ggatttgtta aaagtgttgc    900
taaggatatc tctttagcaa ataactcttc aatttgagaa attaaatgta gagctttgag    960
ggaattacca ccaatagcga aaaagttttc tgtcacacct actttaggta aatgcagaat   1020
attcgaccag atttgtacta attttcttc aacttcattc cgaggcgcta cataggaatt   1080
atgttcacta taattaaata aatcaggctt aggtaatgcc ttacggtcta ctttaccact   1140
gggagttaaa ggaagatgct ccagcatcac aaaagcggct ggaatcataa aatcaggtag   1200
ccttgctttt aggaaatcac gcagattatc aagctgaggt ttgatggagt tataggtaat   1260
ataagcgatg atttgttttt cttgagcgtt atcatcccgc gctatgacta cagcttctct   1320
gacttgtggg tgtgaagata aaacattttc aatctcgcca atttcaattc tataaccccg   1380
aatttttact tgataatctg ttctaccaag atattcaata tttccatcgg gtaaataacg   1440
agctaaatca cctgtttat aaagtcgctt aaactcagaa ttgggaaagg gattaataat   1500
aaattttct ttggtcaatt cttctttatt caaataacca cgagcaaccc ctacaccacc   1560
aatataaatt tcaccagtga caccaatatt tactggttgt aaatcggcat caagaatata   1620
aatttgagta ttagcaatgg gacgaccaat aggtacactc tttaaattac tatcttttct   1680
acattgccaa aatgtgacat caattgctgc ttctgtcggg ccatagaggt tatgtaattc   1740
acattgcaaa tgctggaaaa atctattttg taaatctata gataaagctt caccgctaca   1800
aataactctt tttagagagc tgcatttgct tacatggcga ttttgtaaaa acacttgcag   1860
cattgagggg acaaaatgca acgtagtgat tgttcttga gtaattaaat cgatgaggta   1920
agcactatct ttatgtccgc ctggtttggc tattaccaaa cgtgcgccag ttaataaagt   1980
ccaaaagaac tcccaaacgg aaacatcaaa actaaagggg gttttttgta aaatgctatc   2040
tgtggaatcg atttgataag cttcctgcat ccacaataag cgattacaga tacctttgtg   2100
ggtgttcatt gcacctttg gtttaccagt ggaaccagag gtgtaaatta cataagcaag   2160
attatccgtt tttatattac ttttgggatt ggtattagct tgtgtggaaa ttttctccca   2220
ttccctatct acacagatag tttgtgcttg atggtgggga atttgattga gtaattttc   2280
ttgagttagt agtaccttca cctgagaatc ttctagcata taagctatgc gttcttgagg   2340
atattcaggg tcaataggaa cataagcacc cccagctttg aggattccta aaagacagat   2400
aaccatttct aaggaacgtt ctaaacaaac gcctaccagg gtttctggct ggactcctaa   2460
tgtttgtaaa taatgtccta gctggttgc tttatgattt agttcttgat aagttagttg   2520
ttgcttgtca aaggtgacag cgatcgcctc aggtgttcgt tctacttgag ctacaattag   2580
ttcatgtaaa ctctgggaaa gatcataatc tctgtgggtc gcgttccact ctacaagtaa   2640
cttacgaata ttaaaatcta tagtctgcat atcttctaac tttgctcaat aataaaaaat   2700
ttctcacgca gagacgcaga gaaaacacac tccgcgtccc tctctcttga aaagtttcct   2760
acggagggaa accctcctcc agaacttttc gctgcgctaa cctcagcgtc cctctgcgtt   2820
taaaaactaa tctcccccca attccaccaa cttcccaata ttgaaatcta tccgcgtcca   2880
accttaagaa cgacgcaaat tattcaataa cagtagggga atttgccaat gatgtaccat   2940
caaaaacggt aagggtcat ctggctgata aatcgcatca gtcccgcgcc aaatattccc   3000
cagccatctt tgcaactggg tgaaagaacg gataccagtt aaacgccaaa cttcgtgata   3060
agtccaatag gtaggcttgc ttgtcgttag tggttgtatg gttcagtcg tcggtgcttg   3120
actcaagtac gcttctgcta cctggggtg gtcgtaaaat gtggtaattg ctgaatgtgt   3180
```

-continued

| | |
|---|---|
| gcggggggtta cactcgatgg cgtaaactgt tccgtcttcg gcttggataa agtcaaagga | 3240 |
| aatctgtcct gtcagtttca gttccttgac aaaatgctgt acccattcgg taatttgcgg | 3300 |
| gttatttaca ttctcataat taacttggaa ggctgaagat tcgcaacagc aatgcagtct | 3360 |
| gagttcccca ttccgaacgg tgctatgggt gcagaattcc ttaccgggga taaattcctg | 3420 |
| cataatccac ggttttcgg gagtaattgg caaacttctg acgaatgctg ctgtttcctc | 3480 |
| tggagtagca caggggagtt tggttaagtc caaccgccgc actgagtcgt agggaatgct | 3540 |
| tttgaggatg tatttacgtg tctctccaga aaaatcgaag ttgatgactt gttctggtga | 3600 |
| ggtaatttta aaggatttgg gtactgataa accaagcgat cgcgcttttt gtgtcaacgc | 3660 |
| aaatttatca tccaacattt gggtaatatc tgcgtcaaag tgaaacactt cgcaataatg | 3720 |
| ggataactct ggtttggcta atgagtcgta gtagctaccc actggactgg tgacgggaat | 3780 |
| ataaacatcg atgttttctt gtttgacgat atctaccaaa gcctgaatgt aagcttgggg | 3840 |
| attgtcctgg ggtgcgggga ctgtgtaaaa cttatccact gcttgggaaa aacgatgacc | 3900 |
| agtcaaccag tatttatggg tttccaccaa gacaactcta tgtccagccg cgtggaatga | 3960 |
| ccttgctagt tgtaaagctt tggtcatctt accgccactg ataagaatgg tttgggggtt | 4020 |
| tgctgctttg accttttgcg gtcggaagac taacaaggat ataaaacaa tggtggcatt | 4080 |
| aatgggcaat gctagtaata acaaagccaa agtgcagata ttttggataa ttgcggctat | 4140 |
| tttcgtctgg gaaggaagag acggtgtagc aggtgcggaa gaaggggaa gggattgtgc | 4200 |
| catagtcgat tggacaatta aggttgtatt ctgcggataa ttgttaaacc atctcgcaac | 4260 |
| ggcaacaaaa cctgttctac acgggggtct atagctactg tatgattaaa ttgcgcgatc | 4320 |
| gcttcaccat tgacgctacg ttcctctgct ggtagataaa cttcccccttg taataaggtg | 4380 |
| ttatctacac aaataaagcc atctggtgct aacaaactgc tacctagcaa cttgtgaaaa | 4440 |
| taggctacat actctttttt atctgcgtcg ataaataccca agtcaaaaga ctccccagct | 4500 |
| tctgctaact tatcaagagt tgctaaggct gcatccaatt ccacacgaat cttcaccg | 4560 |
| tggggagatt gttgaaaggc tttctgtcca atttccgccg cgtaagggtc aacttcacaa | 4620 |
| gccacaagca gtccatcctc tggtaatgct tccgccatcg ccagcgccga ataaccggta | 4680 |
| aacatcccaa tttctaagac ttttttagct ttggtcatgt gaacaaacat ctttaaggtt | 4740 |
| tgtccttcga tatgaccaga aagcatctct tgttctagag gacggacggt tgtacctccg | 4800 |
| tggaagtgtt ctccccaggc ttcggtggct gtggtttttg ccaatgcagc gagttcagga | 4860 |
| gattctggag tggtgcattc ttccaaataa gggtctatac ctgcggctaa acgccaagcc | 4920 |
| tgatggatgt ttgctatcaa ttccccaggt aaatctggat gttgcttaac ctcttggact | 4980 |
| atggcttcta actgcttggt taaaattccc aatggtgtaa caggtctagc tgttggttgg | 5040 |
| acaatcacat ttgtcaagtc gcttcgctcc aattcaaaat tcaaaattca aaattcaaaa | 5100 |
| ttaaagacaa ttagtgtccg attatttgcg tagccttctc tttccctacg ggacgctccg | 5160 |
| cgaacagaaa tgctaccgcg ctcgcgcagt gtatccgtgg agtattttgc attttgaatt | 5220 |
| caaaaaagtc attatttaac actcccgatt aattcttttt gataaacggg atacacatcc | 5280 |
| acaccttcac caccacgggg ataactggta caaagttctt tgtggtcagc taatgcggct | 5340 |
| gctaattctt ctcttgtcag gtcattgacg aagacacaat caccaatggg ttttggcata | 5400 |
| gcagctctta acaaaccatc acgagttaat gtgatagatt cagtaccacg ccacaaaata | 5460 |
| tctatatcca acatgggatg gtcgagggat agaccaacgc gactcattaa tcctaaaata | 5520 |

```
cgatcgcgtt ctgcaattgt aatatatcct ctacggcgg cgatcgttgc cgagaaagcc    5580
atatctacat taacggcgtg tccgtggaac atgggtagac gaggcgcaag ttccaaggtg    5640
ggactccaag tgtgaccgta agcaatcacc ctatctaggt ctaactcatg caggttggga    5700
acttccaatt ccaacatctt atggatagct ttgtaagtca aacgatgggc tatttctta    5760 atctctggag ttgcatctat attgccaaaa tgagtacgta gtaattcttc gccgtacttc    5820
tccaacaatt caaaaacttc ttgatgcgct actacagcga ttttaccaa ttccgccatc     5880 ccgttacgta cttggtctgt agggagagta cgcaacaagg agaaatctaa aaatactttg    5940
cgagaagcat gataagcacc caaacggttt ttcagtttgc gatgattaac tgctaccta    6000 attgctacac tggcatcaat taatccaatc aatgtagtag gaatgcggat gtaattgctg    6060
ctgcgacgat atgtagaaca agcaaagccg acaacatctg taattaaacc gccacccacg    6120
actaatactg gttctttgcg gactaatttg aaatctgcaa agacatctat aactctctcg    6180
aaagtttgaa tagtcttatc tggttcagta atggtaatag gaaatagcct cagttctata    6240
ccataatact ggaaatatgc ctgaatttga ttaccataca accgactgac gttagcatct    6300
acaatcgcca agcatcgtcc aaaaccttga tatacatctg ctagtgcaga attctggatt    6360
tcaaaaatac catctacata caccaaatca tactcaatct tttcgtaacc ttctacatga    6420
aaagatgttt ccttagcttc aaactttgct tggacgatac tcatagctc                6469
```

<210> SEQ ID NO 15
<211> LENGTH: 11078
<212> TYPE: DNA
<213> ORGANISM: Artificial Sequence
<220> FEATURE:
<223> OTHER INFORMATION: synthetic vector sequence
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (3343)..(3343)
<223> OTHER INFORMATION: n is a, c, g, or t
<220> FEATURE:
<221> NAME/KEY: misc_feature
<222> LOCATION: (3345)..(3345)
<223> OTHER INFORMATION: n is a, c, g, or t
<220> FEATURE:
<221> NAME/KEY: misc_feature
<222> LOCATION: (3347)..(3347)
<223> OTHER INFORMATION: n is a, c, g, or t
<220> FEATURE:
<221> NAME/KEY: misc_feature
<222> LOCATION: (9883)..(9883)
<223> OTHER INFORMATION: n is a, c, g, or t

<400> SEQUENCE: 15

```
actbactsan tartmasmdm ccgctcattt ttggggtcca gctggttcag ctggtcagta     60
tggctgaaag ccatggtctt aaaaagcagt tcggcgattt ttgctgatct gcttttggg    120 ggttgaaacc gtcgtttttt cgacggtttc ttcttatctt gatactatta gaaacaacgt    180 catttttaaaa aaccgggata aacccttgac acaactgggc ttaggcgtat tatgagttta    240
taaaatgaat aaagaaaaaa cccacgtgag aattcctagt ttggcgaccc ggaacacgtg    300
agttaatctt gaatattcgt atttactaga catagtttaa agcttgagtt agcaagcgtc    360
aagcccttgg ctttagtaaa tacataaaag attagctctt ctcacgtggc tgaatgaggg    420
gagcttttta gtttggctga tagaaaagtt ttagttgatc gatcgcagtc gggcaaagta    480
cgaccatggc gagaacataa gttagaaaat ttacagtatg gtgattattt acaaatgttg    540
```

-continued

```
cactacaaga aagcccatcg agttaaagag tgtggtgaag tattacgttt tgtggaagat      600
aaaaatggtc acaaaaaact ggctcagact tggttttgcc attcccgttt gtgtccgtta      660
tgtaattggc ggcggtcaat gaaacaatct aaccagttaa ctcaaatttt gacagaagca      720
gttaaacagc gaaaaacggg tcggttcttg tttttaacat tgacggtaga gaatactaca      780
ggggatttgt tgaagagtga attacggcag atgggacgag ccattgcaaa gatctttcag      840
tataaaaaag tggctaaaaa tttgttgggc tatgtacgtt caactgaggt taccattaat      900
cacgaagcgg atcagccgat gtatcaccac catatgcatg ttttgctttt tatgaaatct      960
agttatttta caggaactga taattatatt tcacaaacag aatggactag atattggcaa     1020
cgagcgatga aattagctta tgtgccggtt gtgaatgttg aagcggttaa accgaatgtg     1080
aaacgccaga aaaattcctt actggctagt gcccaagaaa cggctaagta tcaggtgaag     1140
tccaaagata ttttaactaa taatcaagaa caagatttac aagtaattga tgatttggaa     1200
caagctttgg ctggttcccg gcaaattagc tatgggggtt tgttaaaaga aattcgtaag     1260
caattgcaac tagaagatgt tgaaaatggt gatttaatta atacggatag tgatgatcaa     1320
aaagttgacc aagtggtacg cgagattgtt gctaagtggg actatcagcg aaaaaattac     1380
tttatttgaa tgagtgctat attatatata aagacaggaa atcatttgtc tagcgggggg     1440 aactcttttta tgatttatgc tactgctgtt aaatttgaag atgaaaattc tgatagaaca     1500
cctaaagcga ttgattctat ttatttagat tctacttcgg atgaaacttg gcattttgga     1560
gagggagaaa acactactcc tattaagggt tggtatgata acatgatgt ttatcgttgg      1620 ttatttttga attttgataa aggccttgtg atgaaggttg ttactggtga aaaaccggat     1680
ataaagcctg ttggtaaaga taaagatgac ccggatggat atgttagatc tgaaaagaat     1740
ggtattgttg ttgataatct tgaaatgctt ccagattcgc cttctccttt gtgatattaa     1800
agaatggaga acgtttattt tgattttgaa tttgtttttt attaataatc attgggagcg     1860
aaagcgacct ttgattattt ttttgccaac ggcaaaaatc gcctcgcaga gcccaaactt     1920
tacaaggtaa agtatattgg gctataccctt gcatggaggt ttgccgaatt ctgtgctatg     1980
ctctaaccaa atttagctgt ttggaaatgg agtggtgaaa tgagttattt agtggctaat     2040
atgcagaaat taaagctga taatttagtt ggcttgggta atcatgatca acgccgaacg      2100
caacatcaca aaaatactga tattgacgtt gaccgttctg gcttaaatta tgatttagtt     2160
gctggtcgga ctaaccattt caaaacggat attgcggctt atattaacga gcataaaacc     2220
agtcagcgag cggtcagaaa agatgccgtt ttagtcaatg aatggattat ttcgagcgat     2280
agcaatttct ttgctaattt aacggcggct gatacgcgca atatttga aacagctaaa       2340 gcttactttg ctgaaaaatt tggtgaagaa atattcgct atgcaattgt tcaccttgat      2400
gagagtacgc cacatatgca tatgggaatt gtgcccttttg atgatgaata aagttgtct    2460 gctaaacggg tgtttaatcg tgcggctttg caaaacgttc aagatcaatt gccgacttat     2520
ttgcaacagc atggttttaa tattcaacgt ggggttcaag aatcggaacg caaaagttta    2580
acggtgccag aatataaagc tatgcgggaa gatttgaaaa aggcgacgct tcaaaaacaa     2640
gaaatacaag ctgaacttga agatgccaga aaacgccttg ctgaacttaa acctcgtgat     2700
cagcaggaaa ttgagagcaa acctactttt ttaagcaagg ataaagtggt tgttagaaaa     2760
agtgatcttc atgacttaga atctcgagca gctgtcagtg atatttataa tcaacaacag     2820
aaccgtttaa aacttgataa tcaaagccta aattatcaac tgcttgaagt taaagacaat     2880
```

```
aattatgagt taagcaagaa aaatgagaag ctccaaaaat tagtggatac gttacaagga    2940
attgttcgga gcgttgaccg gttcttacag cgcaaattag gtgttggctt accaagtgag    3000
tggctagaac gagctggact aaaagaaccg tctaaaaacg cccctcagag gccgcaggaa    3060
cgttcggagg gacagcatga tgaattagat ggtccaagtc tttgaatttg tcctatggct    3120
ttaaattacc cgctgatgag cattgaagct ggttaatggc cgtcagtcaa cggtaaatcg    3180
aattaaaggg acttactgct ttagcagtta gtcccttttt gaggctttaa ggagttgact    3240
gactcactag accaagacac ttttgcgcat gcaaagaaaa gcacacctgc tttttttgcc    3300
tgcctcacgg cgagtgcggg gtgagtttga gcgggagctc shnrnrnwth rmtragatct    3360
agcgctatag ttgttgacag aatggacata ctatgatata ttttgctata gcgatgaatt    3420
attttccaga caatcttgta aacgctgtgc taaaacctgt acatggggtt ctagaacaaa    3480
cgaataatgg tttccaggga catcaataat cttaatttct tgagccgcca ttacagaaaa    3540
taattctacc caaactaagg tcgggtcagg agccataata tgttttttccc tggctcgaaa    3600 tacagtgact tttcctggat atggttgtct tatataggaa taagttgctt ttaaagttcc    3660
caccaaaaca tcaagaatac ggcgattatt ttgacgttct acaccaggcg ggaatattct    3720
agcgctccgt gctttatcaa tgatgtaatt aattttttct tctacagtta aattttctat    3780
ttcttcaggt gtgactagat tatcttgacc aaacataccg ccaaaaactc tggagagaac    3840
accaactaaa taaacgtcat caatgggttt ttgtttatcc agcagaatcg gtacgtaaga    3900
atctaatatt gctagtaaag atacttcttg tccttgtcta tgtaactgct gtgctacttc    3960
ataagctacg actccaccaa atgaccaccc cccgacacga taaggccctt ggggttgaaa    4020
ttctctaata gttttgacgt agagactagc catatcttca actcgcgtca agggtgcttc    4080
atctccataa aatccttgag cttgtaagcc ataaatggt tggtcagttc ctatatattg    4140
tgcgagttta aaatagcata aacatgacc accagcagga tgtatacaaa agaaaggctg    4200
ctgcttacct tgtggttgaa ttggaactag gggtgaatta tggatttggt tgtttgcttg    4260
aataaccttg gctaaatctg caattactgg atttgttaaa agtgttgcta aggatatctc    4320
tttagcaaat aactcttcaa tttgagaaat taaatgtaga gctttgaggg aattaccacc    4380
aatagcgaaa aagttttctg tcacacctac tttaggtaaa tgcagaatat tcgaccagat    4440
ttgtactaat ttttcttcaa cttcattccg aggcgctaca taggaattat gttcactata    4500
attaaataaa tcaggcttag gtaatgcctt acggtctact ttaccactgg gagttaaagg    4560
aagatgctcc agcatcacaa aagcggctgg aatcataaaa tcaggtagcc ttgcttttag    4620
gaaatcacgc agattatcaa gctgaggttt gatggagtta taggtaatat aagcgatgat    4680 ttgttttttct tgagcgttat catcccgcgc tatgactaca gcttctctga cttgtgggtg    4740
tgaagataaa acattttcaa tctcgccaat ttcaattcta taaccccgaa ttttacttg    4800 ataatctgtt ctaccaagat attcaatatt tccatcgggt aaataacgag ctaaatcacc    4860
tgttttataa agtcgcttaa actcagaatt gggaaaggga ttaataataa attttctttt    4920
ggtcaattct tctttattca ataaccacg agcaacccct acaccaccaa tataaatttc    4980
accagtgaca ccaatattta ctggttgtaa atcggcatca agaatataaa tttgagtatt    5040
agcaatggga cgaccaatag gtacactctt taaattacta tcttttctac attgccaaaa    5100
tgtgacatca attgctgctt ctgtcgggcc atagaggtta tgtaattcac attgcaaatg    5160
ctggaaaaat ctatttttgta aatctataga taaagcttca ccgctacaaa taactctttt    5220
tagagagctg catttgctta catggcgatt ttgtaaaaac acttgcagca ttgaggggac    5280
```

| | |
|---|---|
| aaaatgcaac gtagtgattt gttcttgagt aattaaatcg atgaggtaag cactatcttt | 5340 |
| atgtccgcct ggtttggcta ttaccaaacg tgcgccagtt aataaagtcc aaaagaactc | 5400 |
| ccaaacggaa acatcaaaac taaagggggt tttttgtaaa atgctatctg tggaatcgat | 5460 |
| ttgataagct tcctgcatcc acaataagcg attacagata cctttgtggg tgttcattgc | 5520 |
| acctttggt ttaccagtgg aaccagaggt gtaaattaca taagcaagat tatccgtttt | 5580 |
| tatattactt ttgggattgg tattagcttg tgtggaaatt ttctcccatt ccctatctac | 5640 |
| acagatagtt tgtgcttgat ggtggggaat tgattgagt aattttctt gagttagtag | 5700 |
| taccttcacc tgagaatctt ctagcatata agctatgcgt tcttgaggat attcagggtc | 5760 |
| aataggaaca taagcacccc cagctttgag gattcctaaa agacagataa ccatttctaa | 5820 |
| ggaacgttct aaacaaacgc ctaccagggt ttctggctgg actcctaatg tttgtaaata | 5880 |
| atgtcctagc tggtttgctt tatgatttag ttcttgataa gttagttgtt gcttgtcaaa | 5940 |
| ggtgacagcg atcgcctcag gtgttcgttc tacttgagct acaattagtt catgtaaact | 6000 |
| ctgggaaaga tcataatctc tgtgggtcgc gttccactct acaagtaact tacgaatatt | 6060 |
| aaaatctata gtctgcatat cttctaactt tgctcaataa taaaaatttt ctcacgcaga | 6120 |
| gacgcagaga aaacacactc cgcgtccctc tctcttgaaa agtttcctac ggagggaaac | 6180 |
| cctcctccag aacttttcgc tgcgctaacc tcagcgtccc tctgcgttta aaaactaatc | 6240 |
| tcccccaat tccaccaact tcccaatatt gaaatctatc cgcgtccaac ctttaagacg | 6300 |
| acgcaaatta ttcaataaca gtaggggaat ttgccaatga tgtaccatca aaaacggtaa | 6360 |
| ggggtcatct ggctgataaa tcgcatcagt cccgcgccaa atattcccca gccatctttg | 6420 |
| caactgggtg aaagaacgga taccagttaa acgccaaact tcgtgataag tccaataggt | 6480 |
| aggcttgctt gtcgttagtg gttgtatggt ttcagtcgtc ggtgcttgac tcaagtacgc | 6540 |
| ttctgctacc tggggtggt cgtaaaatgt ggtaattgct gaatgtgtgc gggggttaca | 6600 |
| ctcgatggcg taaactgttc cgtcttcggc ttggataaag tcaaaggaaa tctgtcctgt | 6660 |
| cagtttcagt tccttgacaa aatgctgtac ccattcggta atttgcgggt tatttacatt | 6720 |
| ctcataatta acttggaagg ctgaagattc gcaacagcaa tgcagtctga gttccccatt | 6780 |
| ccgaacggtg ctatgggtgc agaattcctt accggggata aattcctgca taatccacgg | 6840 |
| tttttcggga gtaattggca aacttctgac gaatgctgct gtttcctctg gagtagcaca | 6900 |
| ggggagtttg gttaagtcca accgccgcac tgagtcgtag ggaatgcttt tgaggatgta | 6960 |
| tttacgtgtc tctccagaaa aatcgaagtt gatgacttgt tctggtgagg taattttaaa | 7020 |
| ggatttgggt actgataaac caagcgatcg cgcttttgt gtcaacgcaa atttatcatc | 7080 |
| caacatttgg gtaatatctg cgtcaaagtg aaacacttcg caataatggg ataactctgg | 7140 |
| tttggctaat gagtcgtagt agctacccac tggactggtg acgggaatat aaacatcgat | 7200 |
| gttttcttgt ttgacgatat ctaccaaagc ctgaatgtaa gcttgggat tgtcctgggg | 7260 |
| tgcggggact gtgtaaaact tatccactgc ttgggaaaaa cgatgaccag tcaaccagta | 7320 |
| tttatgggtt tccaccaaga caactctatg tccagccgcg tggaatgacc ttgctagttg | 7380 |
| taaagctttg gtcatcttac cgccactgat aagaatggtt tggggttttg ctgctttgac | 7440 |
| cttttgcggt cggaagacta acaaggatat aaaaacaatg gtggcattaa tgggcaatgc | 7500 |
| tagtaataac aaagccaaag tgcagatatt ttggataatt gcggctattt tcgtctggga | 7560 |
| aggaagagac ggtgtagcag gtgcggaaga aaggggaagg gattgtgcca tagtcgattg | 7620 |

-continued

```
gacaattaag gttgtattct gcggataatt gttaaaccat ctcgcaacgg caacaaaacc    7680
tgttctacac gggggtctat agctactgta tgattaaatt gcgcgatcgc ttcaccattg    7740
acgctacgtt cctctgctgg tagataaact tccccttgta ataaggtgtt atctacacaa    7800
ataaagccat ctggtgctaa caaactgcta cctagcaact tgtgaaaata ggctacatac    7860
tcttttttat ctgcgtcgat aaataccaag tcaaaagact ccccagcttc tgctaactta    7920
tcaagagttg ctaaggctgc atccaattcc acacgaatct ttccaccgtg gggagattgt    7980
tgaaaggctt tctgtccaat ttccgccgcg taagggtcaa cttcacaagc cacaagcagt    8040
ccatcctctg gtaatgcttc cgccatcgcc agcgccgaat aaccggtaaa catcccaatt    8100
tctaagactt ttttagcttt ggtcatgtga acaaacatct ttaaggtttg tccttcgata    8160
tgaccagaaa gcatctcttg ttctagagga cggacggttg tacctccgtg gaagtgttct    8220
ccccaggctt cggtggctgt ggttttttgcc aatgcagcga gttcaggaga ttctggagtg    8280
gtgcattctt ccaaataagg gtctatacct gcggctaaac gccaagcctg atggatgttt    8340
gctatcaatt ccccaggtaa atctggatgt tgcttaacct cttggactat ggcttctaac    8400
tgcttggtta aaattcccaa tggtgtaaca ggtctagctg ttggttggac aatcacattt    8460
gtcaagtcgc ttcgctccaa ttcaaaattc aaaattcaaa attcaaaatt aaagacaatt    8520
agtgtccgat tatttgcgta gccttctctt tccctacggg acgctccgcg aacagaaatg    8580
ctaccgcgct cgcgcagtgt atccgtggag tattttgcat tttgaattca aaaagtcat    8640
tatttaacac tcccgattaa ttcttttga taaacgggat acacatccac accttcacca    8700
ccacggggat aactggtaca aagttctttg tggtcagcta atgcggctgc taattcttct    8760
cttgtcaggt cattgacgaa gacacaatca ccaatgggtt ttggcatagc agctcttaac    8820
aaaccatcac gagttaatgt gatagattca gtaccacgcc acaaaatatc tatatccaac    8880
atgggatggt cgagggatag accaacgcga ctcattaatc ctaaaatacg atcgcgttct    8940
gcaattgtaa tatatcctct acgggcggcg atcgttgccg agaaagccat atctacatta    9000
acggcgtgtc cgtggaacat gggtagacga ggcgcaagtt ccaaggtggg actccaagtg    9060
tgaccgtaag caatcaccct atctaggtct aactcatgca ggttgggaac ttccaattcc    9120
aacatcttat ggatagcttt gtaagtcaaa cgatgggcta tttctttaat ctctggagtt    9180
gcatctatat tgccaaaatg agtacgtagt aattcttcgc cgtacttctc caacaattca    9240
aaaacttctt gatgcgctac tacagcgatt tttaccaatt ccgccatccc gttacgtact    9300
tggtctgtag ggagagtacg caacaaggag aaatctaaaa atactttgcg agaagcatga    9360
taagcaccca aacggttttt cagtttgcga tgattaactg ctaccttaat tgctacactg    9420
gcatcaatta atccaatcaa tgtagtagga atgcggatgt aattgctgct gcgacgatat    9480
gtagaacaag caaagccgac aacatctgta attaaaccgc cacccacgac taatactggt    9540
tctttgcgga ctaatttgaa atctgcaaag acatctataa ctctctcgaa gtttgaata    9600
gtcttatctg gttcagtaat ggtaatagga atagcctca gttctatacc ataatactgg    9660
aaatatgcct gaatttgatt accatacaac cgactgacgt tagcatctac aatcgccaag    9720
catcgtccaa aaccttgata tacatctgct agtgcagaat tctggatttc aaaaatacca    9780
tctacataca ccaaatcata ctcaatcttt tcgtaacctt ctacatgaaa agatgtttcc    9840
ttagcttcaa actttgcttg gacgatactc atgactbact santartmwc sagatctagc    9900
gctatagttg ttgacagaat ggacatacta tgatatattt tgctatagcg atggttgtaa    9960
ttggggagca ccgccacaca caagtcacag tcgacttgca ggcaattaag acaaatatta   10020
```

```
gtaatgaaat ggcgcaaaag gatgagttga ccgagttatg ggcagtcgtt aaagcgaatg    10080
gttatggaca tggaattatc caagttgctc aggccgccaa agaagccggg gcgaccggct    10140
tttgtgttgc aatcctggat gaggccttag cgttgcgggc cgctggcttt gcggaaccca    10200
tcctagtact tggaattacg gaaccggaat acgccccact ggtagctgaa aaggatattt    10260
cactagctgt tggaacgcaa gattggctga ctacggccgc agcaatttta gcggctaatc    10320
aagtgacgac accacttcac gttcatcttg cattagatac gggtatggga cgaatcgggt    10380
ttcagacgcc cgaagaattg gcaacggcgg ttacgacttt gcgtcaaccg cagtcaccat    10440
ttgactttga agggattttt acgcattttg caacggctga ccaggcagat gatacgtatt    10500
ttactcatca attaaataat tggaaacact tgattgcagt ggtggatgag ctaccacgct    10560
atgtccacgt gtccaattcg gccaccagtc tctggcatca agcttgcaat ggcaacatgg    10620
tgcgctttgg ggttgcactc tatggtctaa atccttctgg tcgcgaactc agcgcaccat    10680
accccttgca acccgcgttg tcgctaacgg cacgcttgac gtttgttaaa cgcttggctc    10740
ggggcaaatc ggtcagctat ggtgccacgt atacggccgc acaggatgaa tggattggca    10800
cggtgccgat tgggtatgcg gacggctatg aacgccgatt acaaggcttc catgtacttg    10860
ttgatggtga gttttgcgaa atcgtcggac gggtctgcat ggaccagctg atggttcgtc    10920
tgccacatga agtaccggtt ggagctaagg taactttggt tggcacggac ggtgctcgta    10980
ccatttcgtt gcaagatatt gctgactatt gtgggacaat tcattatgag attgcttgtg    11040
ggttagcacc acgagtgccg agagtttata tagattaa                           11078

<210> SEQ ID NO 16
<211> LENGTH: 31
<212> TYPE: DNA
<213> ORGANISM: Artificial Sequence
<220> FEATURE:
<223> OTHER INFORMATION: synthetic primer

<400> SEQUENCE: 16
gagatcccat atgagtatcg tccaagcaaa g                                   31

<210> SEQ ID NO 17
<211> LENGTH: 37
<212> TYPE: DNA
<213> ORGANISM: Artificial Sequence
<220> FEATURE:
<223> OTHER INFORMATION: synthetic primer

<400> SEQUENCE: 17
gtacctcgag tcatgaatta ttttccagac aatcttg                             37

<210> SEQ ID NO 18
<211> LENGTH: 982
<212> TYPE: DNA
<213> ORGANISM: Streptomyces glaucescens

<400> SEQUENCE: 18
ggtccccacc ccgcgggccg ccgcccgggc ggcgtcgacg aactccaggg cgcgcggctg     60
ctgccgttcc ccgccaactg acccgccccg cgctctcttg gagcactcgc acatgaccgt    120
ccggaagaac caggccaccc tgaccgccga cgagaagcgg cgcttcgtcg ccgccgtcct    180
ggaactcaag cgcagcggcc gctacgacga gttcgtcacc acccacaacg ccttcatcat    240
cggcgacacc gacgcgggtg agcgcaccgg ccaccgctcg ccctcgttcc tgccctggca    300
```

-continued

```
ccgcagatac ctgctggagt tcgagcgggc cctgcagagc gtggacgcct cggtcgccct    360
cccctactgg gactggtccg ccgaccgcac cgcacgggcc tcgctgtggg cgcccgactt    420
cctcggcggc accgggcgca gcctggacgg ccgggtcatg gacggaccgt tcgccgcctc    480
ggccggcaac tggccgatca acgtgcgcgt ggacgggcgc gcgtacctgc ggcggtcgct    540
cggcaccgcg gtgcgggaac tgccgacgcg ggcggaggtg gagtcggtgc tcggcatggc    600
cacgtacgac acggccccct ggaacagcgc ctcggacggc ttccgcaacc acctggaggg    660
ctggcgcggc gtcaacctgc acaaccgcgt ccacgtctgg gtgggcgggc agatggccac    720
cgggatgtcg cccaacgacc cggtgttctg gctgcacaac gcctacgtcg acaagctgtg    780
ggccgagtgg cagcgccgcc acccgggatc cggctacctc cccgccgccg ggacgcccga    840
cgtggtggac ctgaacgaca ggatgaagcc ctggaacgac acctcccggg ccgaccttt     900 ggaccacacc gcccactaca ccttcgacac cgactgaccc ggccggccgt cggcaggcat    960
cctcccgcag gtcagggta cc                                              982
```